(12) United States Patent
Arnone et al.

(10) Patent No.: US 6,957,099 B1
(45) Date of Patent: Oct. 18, 2005

(54) METHOD AND APPARATUS FOR TERAHERTZ IMAGING

(75) Inventors: Donald Dominic Arnone, Cambridge (GB); Craig Michael Ciesla, Cambridge (GB)

(73) Assignee: Teraview Limited, (GB)

(*) Notice: Subject to any disclaimer, the term of this patent is extended or adjusted under 35 U.S.C. 154(b) by 0 days.

(21) Appl. No.: 09/914,081

(22) PCT Filed: Feb. 23, 2000

(86) PCT No.: PCT/GB00/00632

§ 371 (c)(1),
(2), (4) Date: Apr. 23, 2002

(87) PCT Pub. No.: WO00/50859

PCT Pub. Date: Aug. 31, 2000

(30) Foreign Application Priority Data

Feb. 23, 1999 (GB) .................................. 9904166
Jun. 4, 1999 (GB) .................................. 9913087

(51) Int. Cl.[7] .......................... A61B 6/00; H01L 31/00
(52) U.S. Cl. ...................................... 600/473; 250/330
(58) Field of Search ............................ 600/473, 407, 600/310, 476, 322, 316; A61B 6/00; 250/330, 250/338.1, 358.1; H01L 31/00

(56) References Cited

U.S. PATENT DOCUMENTS

| 5,213,105 | A | * | 5/1993 | Gratton et al. ............... 600/473 |
| 5,623,145 | A | | 4/1997 | Nuss ........................... 250/330 |
| 5,692,504 | A | * | 12/1997 | Essenpreis et al. ........... 600/316 |
| 5,710,430 | A | | 1/1998 | Nuss ........................ 250/358.1 |
| 5,782,755 | A | * | 7/1998 | Chance et al. ............... 600/322 |
| 5,789,750 | A | | 8/1998 | Nuss ........................ 250/338.1 |
| 5,807,263 | A | * | 9/1998 | Chance ....................... 600/476 |
| 5,983,121 | A | * | 11/1999 | Tsuchiya .................... 600/310 |
| 6,058,624 | A | * | 5/2000 | Bach et al. ................... 34/374 |

FOREIGN PATENT DOCUMENTS

| EP | 0727671 | 8/1996 |
| EP | 0 828 162 A2 | 3/1998 |
| EP | 0828143 | 3/1998 |
| EP | 0 841 548 A2 | 5/1998 |
| EP | 0841548 | 5/1998 |

(Continued)

OTHER PUBLICATIONS

Wu Q et al: "Two-Dimensional Electro-Optic Imaging of the ThZ Beams" Applied Physics Letters, US, American Institute of Physics. New York vol. 69, No. 8, Aug. 19, 1996, pp. 1026-1028, XP000626128 ISSN: 0003-6951.

(Continued)

*Primary Examiner*—Daniel Robinson
(74) *Attorney, Agent, or Firm*—Ostrolenk, Faber, Gerb & Soffen, LLP

(57) ABSTRACT

In an apparatus and method for imaging a sample: a) the sample to be imaged is irradiated with pulsed electromagnetic radiation with a plurality of frequencies in the range from 50 GHz to 84 THz; b) an area of the sample is subdivided into a two dimensional array of pixels, and radiation from each pixel is detected over a plurality of frequencies; and c) an image is generated from the radiation detected in step (b) preferably using a frequency or a selection of frequencies from the plurality of frequencies in the pulsed electro-magnetic radiation. The method can be used as a medical imaging technique and can be used to image cancer tumours.

25 Claims, 42 Drawing Sheets

FOREIGN PATENT DOCUMENTS

| | | |
|---|---|---|
| EP | 0864857 | 9/1998 |
| GB | 2254417 | 10/1992 |
| WO | WO 97/45747 | 12/1997 |

OTHER PUBLICATIONS

Patent Abstracts Of Japan vol. 13, No. 182 (C-591), Apr. 27, 1989 & JP 01 011530 A (Hitachi), Jan. 17, 1989.

*IEEE Journal of Selected Topics in Quantum Electronics*, vol. 2, No. 3, Sep. 1996, pp. 679-692: *T-Ray Imaging*, Daniel M. Mittleman, et. al. —XP 000689828.

Fattinger, et al., "Point Source Terahertz Optics" Appl. Phys. Lett. 53(16), Oct. 17, 1988, pp. 1480-1482.

Fattinger et al., "Tetahertz Beams" Appl. Phys. Lett. 54(6), Feb. 6, 1989, pp. 490-492.

Mittleman, et al. "T-Ray Imaging" IEEE Journal of Selected Topics in Quantum Electronics, 2 (3), Sep. 1996, pp. 679-692.

Zamdmer et al., "On-Chip Frequency-Domain Submillimeter-Wave Transceiver" Appl. Phys. Lett. 75 (24), Dec. 12, 1999, pp. 3877-3879.

* cited by examiner

Fig. 28: Sample port for THz breast screening (for use with all-optical systems in Figures 2 and 3)

Fig. 29: Sample port for THz breast screening (for use with all-optical systems in Figures 2 and 3)

Fig. 31: Possible alternative configuration of coupling optics used in Figure 5 (regions denoted 1. And 2. In dotted boxes).

*THz transmission through animal bone*
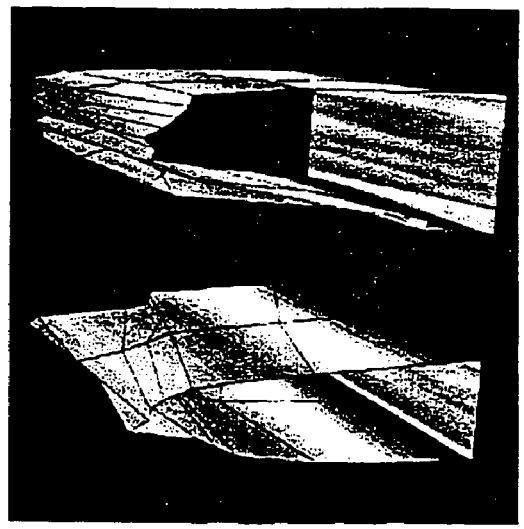
*3D THz image through 2 bone sample*
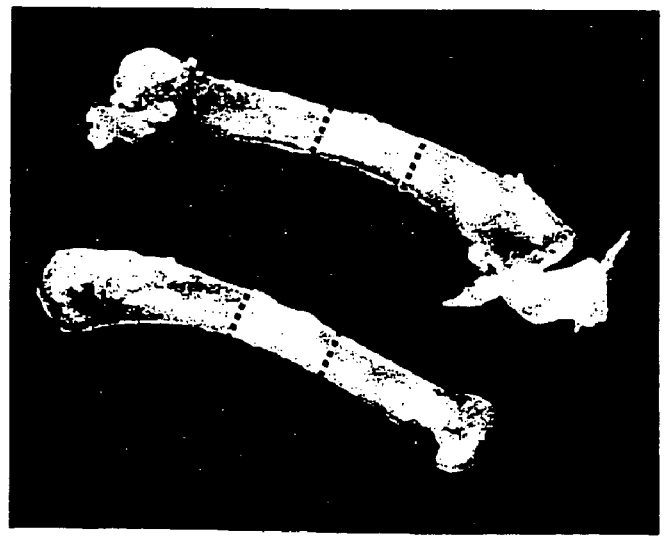
*Example of 2 bones – visible image*
(a)  (b)
Fig. 38

Fig. 40: THz imaging of different types of animal tissue: clotted blood

*Transmittance = (signal through skin)/(reference signal)*

METHOD AND APPARATUS FOR TERAHERTZ IMAGING

The present invention relates to the field of imaging samples with radiation in the infra-red (IR) frequency range. More specifically, the present invention relates to apparatus and methods for improving contrast in images obtained using electromagnetic radiation in the higher Gigahertz (GHz) and the Terahertz (THz) frequency ranges. However, in such imaging technology, all such radiation is colloquially referred to as THz radiation, especially that in the range from 50 GHz to 84 THz.

Recently, there has been much interest in using THz radiation to look at a wide variety of samples using a range of methods. THz radiation has been used for both imaging samples and obtaining spectra. Recently, work by Mittleman el al. IEEE Journal of Selected Topics in Quantum Electronics, Vol. 2, No. 3, September 1996, page 679 to 692 illustrates the use of using THz radiation to image various objects such as a flame, a leaf, a moulded piece of plastic and semiconductors.

THz radiation penetrates most dry, non metallic and non polar objects like plastics, paper, cardboard and non polar organic substances. Therefore, THz radiation can be used instead of x-rays to look inside boxes, cases etc. THz has lower energy, non-ionising photons than X-rays, hence, the health risks of using THz radiation are expected to be vastly reduced compared to those using conventional X-rays.

The use of THz imaging for medical purposes has also been suggested in the above referenced paper. However, it has previously been believed that strong-water absorption prevents the use of THz in many bio-medical research areas. Previously, a large amount of THz imaging has been analysed on the basis of obtaining contrasts between strongly water absorbing regions and non strongly water absorbing regions.

The present invention addresses the above problems and is concerned with methods for enhancing image contrasts in such THz images to allow THz to be used to not only image contrast based on water absorption but to allow a fine contrast to be shown in THz imaging over a range of different samples.

In a first aspect, the present invention provides a method of imaging a sample, the method comprising the steps of:
a) irradiating the sample to be imaged with pulsed electro-magnetic radiation with a plurality of frequencies in the range from 50 GHz to 84 THz;
b) subdividing an area of the sample into a two dimensional array of pixels, and detecting radiation from each pixel over a plurality of frequencies;
c) generating an image from the radiation detected in step (b) using a frequency or a selection of frequencies from the plurality of frequencies in the incident pulsed electromagnetic radiation.

Preferably, the sample is irradiated with pulsed electromagnetic radiation with a plurality of frequencies in the range from 100 GHz to 20 THz; more preferably from 500 GHz to 10 THz.

The detected radiation may be analysed for a single frequency, or, it may be analysed over a selected frequency range. A selected frequency range is taken to be a frequency range which is typically, less than a third of the total frequency range of the pulsed e-m radiation used to irradiate the sample. More preferably, the selected frequency range is less than 10% of the total frequency range of the pulsed e-m radiation used to irradiate the sample.

For example, it has previously been mentioned that water is a strong absorber of THz. There are 'windows' in the water absorption spectra from 50 GHz to 500 GHz, from 30 THz to 45 THz and from 57 THz to 84 THz. If the sample is a irradiated with a range of frequencies from 50 GHz to 84 THz, it may be preferable to generate the image using one or more of the following selected frequency ranges: 50 GHz to 500 GHz, 30 THz to 45 THz and 57 THz to 84 THz. The image may be generated by integrating over the selected frequency range.

Thus, the present invention allows an image to be created from single frequency or from a selected frequency range. Also, the present invention allows a plurality of images to be derived from a plurality of frequencies or allows a single image to be derived from data from two or more distinct frequencies.

The present invention can either be used to image a sample by detecting radiation transmitted through the sample or reflected from the sample.

The image or images generated by the present invention my be displayed in a number of ways. For example, the method of the first aspect of the present invention may further comprise the step of displaying a sequence of images generated in step (c) for a plurality of different frequencies.

The image generated in step (c) may be scanable through a continuum of frequencies. Alternatively, the image generated in step (c) can be stepped through a plurality of discrete frequencies.

For many imaging contrast techniques discussed herein, a reference signal is required. Ideally, the reference signal is obtained from THz radiation which has not been passed through or reflected from the area of the sample which is to be imaged.

The reference signal may be obtained from a fraction of the electro-magnetic pulsed radiation which has not been passed through the sample, alternatively, the reference signal may be obtained by passing the pulsed electro-magnetic radiation through a different part of the sample. For example, the present invention may be used to image tumours tissue, the area of the sample which is to be imaged would be the tumour, the reference signal could be obtained by passing the radiation through a healthy part of the tissue. The reference signal may also be measured when the sample is absent. For example, the reference signal could be measured before the sample is positioned in the path of the radiation beam or the reference signal could be measured after the sample has been imaged.

In general, the present invention will be performed using imaging apparatus which is configured to detect temporal data at each pixel. Preferably, the data is Fourier transformed to give the complex THz electric field in the frequency domain $E(\omega)$.

The image can be obtained in a number of ways from the complex THz electric field $E(\omega)$, e.g.:
(i) The power spectrum $P_{sample}(\omega)$ of the sample and the power spectrum $P_{ref}(\omega)$ of the reference signal may be calculated. The image could then be generated by plotting the difference between the two Power spectrums for a given frequency for each pixel at a selected frequency over integrated over a selected frequency range.
(ii) The power spectrum $P_{sample}$ of the sample and the reference power spectrum $P_{ref}$ may be divided to give the transmittance. The transmittance may then be plotted for each pixel at a selected frequency over integrated over a selected frequency range.

(iii) The frequency dependent absorption coefficient $\alpha(\omega)$ may be calculated from the complex electric field $E(\omega)$ and plotted for each pixel at a selected frequency over integrated over a selected frequency range.

(iv) The frequency dependent refractive index $\eta(\omega)$ may also be calculated from the complex electric field and plotted for each pixel at a selected frequency over integrated over a selected frequency range.

The detected temporal electric field contains both phase and amplitude information which give a complete description of the complex dielectric constant of the medium in the beam path. The sample to be characterised is inserted into the beam and the shape of the pulses that have propagated through the sample or have been reflected from the sample are compared with the reference temporal profile acquired without the sample. The ratio of the complex electric field $E(\omega)$ and the reference signal $E_{ref}(\omega)$ is calculated to give the complex response function of the sample $S(\omega)$. In the most simple case, the complex response function is given by:

$$S(\omega) = \frac{E(\omega)}{E_{ref}(\omega)} \propto \exp\left(\frac{i\omega d}{c}(\eta(\omega) - 1)\right) \exp(-\alpha(\omega)d) \quad (1)$$

where d is the sample thickness, c is the velocity of light in vacuum, $\eta$ is the refractive index and $\alpha$ is the absorption coefficient. The experimental absorption coefficient $\alpha(\omega)$ and the refractive index $\eta(\omega)$ may then be easily extracted from the magnitude $M(\omega)$ and the phase $\phi(\omega)$ of $S(\omega)$, respectively, according to $$\alpha(\omega) = -\frac{1}{d}\ln(M(\omega)) \quad (2)$$

$$\eta(\omega) = 1 + \left(\frac{c}{\omega d}\right)\phi(\omega) \quad (3)$$

Additional terms may be included in equations (1) to (3) to account for reflections at dielectric interfaces of a sample, thus allowing accurate analysis of multilayered samples.

These parameters are simply related to the complex dielectric function $\epsilon(\omega)$ of the sample $$\epsilon(\omega)=(\eta(\omega)+ik(\omega))^2=(\eta(\omega)+i\alpha(\omega)c/2\omega)^2 \quad (4)$$

The data derived as discussed in (i) to (iv) above, may be directly plotted either as a colour or a grey scale image where the colour or shade of grey of each pixel represents a given magnitude.

Instead of a single frequency, a selected frequency range could be chosen and the result and data of (i) to (iv) integrated over that range. The integrated data could then be plotted.

It may also be preferred to subdivide the magnitude of the data process in accordance with any of (i) to (iv) above into various bands. For example, all data below a certain value could be assigned the value 0, all data in the next magnitude range could be assigned the value 1, etc. These ranges may have equal widths in magnitude or they may have different widths. Different widths may be preferable to enhance contrast e.g. to emphasise contrast in regions of the sample where there is little variation in the sample absorption of THz.

Preferably, the present invention uses two or more frequencies. The data from say two frequencies is processed in accordance with any of (i) to (iv) above. The data is then banded as described for a single frequency above.

The data may be split into two bands, one assigned the value "0" and the other "1". The data from both frequencies can then be added together using a rule such as a Boolean algebraic expression e.g. AND, OR, NOT, NAND XOR, etc.

Of course, the present invention also allows images to be compared from two different frequencies. This may be particularly useful to identify a substance where the absorption to THz changes over a certain frequency range.

Other methods are also possible for such THz imaging. It is known to plot the maximum or minimum of the electric field. Indeed, this has been done by Mittleman in the earlier reference paper. However, far greater contrast is achieved by plotting the peak to peak signal, i.e. the distance between the minimum and maxima of the electric field. Therefore, in a second aspect, the present invention provides a method for imaging a sample, the method comprising the steps of:

a) irradiating the sample to be imaged with a pulsed electro-magnetic radiation with a plurality of frequencies in the range from 50 GHz to 84 THz;

b) subdividing an area of the sample into a two dimensional array of pixels and detecting radiation from each pixel over a plurality of frequencies;

c) generating an image from the radiation detected in step (b) by calculating the difference between the magnitude of a maxima and a minima of the radiation detected in step (b) for each pixel.

Preferably, the main peak minima and maxima are chosen i.e. the highest and lowest parts of the temporal trace.

More preferably, the sample is irradiated with pulsed electro-magnetic radiation with a plurality of frequencies in the range from 100 GHz to 20 THz;

It is also known to derive temporal information from the data. For example, the time difference between the maxima of the electric field which is passed through the sample and the field which is not passed through or reflected from the area of the sample, which is to imaged, can be plotted. However, there has been no suggestion of plotting the temporal difference between the maximum and the minimum of the electric field. This provides data on the frequency dependent absorption. Therefore, in a third aspect, the present invention provides a method for imaging a sample, the method comprising the steps of:

a) irradiating the sample to be imaged with pulsed electromagnetic radiation with a plurality of frequencies in the range from 50 GHz to 84 THz;

b) subdividing an area of the sample into a two dimensional array of pixels, and detecting radiation from each pixel over a plurality of frequencies;

c) generating an image from the radiation detected in step (b) by calculating the difference between the temporal positions of a maxima and a minima of the radiation detected in step (b) for each pixel.

Preferably, the main peak minima and maxima are chosen i.e. the highest and lowest parts of the temporal trace.

More preferably, the sample is irradiated with pulsed electromagnetic radiation with a plurality of frequencies in the range from 100 GHz to 20 THz;

To obtain even better contrast, the temporal difference between the maximum and the minimum field may also multiplied by a value of the field at that pixel. For example, the minimum, maxima or difference between the minima and maxima.

As mentioned above, the method of the present invention is suitable for medical imaging and is ideally suited to probing certain tissue abnormalities and conditions. It is also useful for imaging items inside containers, for investigating the internal structure and composition of foods, as well as authentication of documents, labels, banknotes or other printed matter and for analogous security applications. Some particular medical applications will now be explained in more detail. First, a description of some examples of the different types of tissue types which can be imaged will follow:

Cancerous Tissue:

Normal tissue contains a large number of mature cells of uniform shape and size. Each cell is characterised by a nucleus of uniform size.

Benign Neoplasm:

Benign neoplasm involve cellular proliferation of adult or mature cells growing slowly in an orderly manner in a capsule. These tumours do not invade surrounding tissue but may cause harm through pressure on vital structures within an enclosed structure such as the skull.

Malignant Cells:

A malignant cell is one in which the basic structure and activity have become arranged in a manner that is unknown and from a cause or causes that are still poorly understood. The malignant cells lose the normal specialised function of the normal cell or may take on new characteristics and functions. A characteristic of malignant cells that can be observed through a microscope is loss of differentiation, or loss of likeness to the original cell (parent tissue) from which the tumour growth originated. This loss of differentiation is called anaplasia, and its extent is a determining factor in the extent of malignancy of the tumour. Anaplasia is one of the most reliable indicators of malignancy. It is seen only in cancers and does not appear in benign neoplasms.

Other characteristics of malignant cells that can be seen through a microscope are the presence of nuclei of various sizes, many of which contain unusually large amounts of chromatin, and the presence of mitotic figures (cells in the provision of division), which denotes rapid and disorderly division of cells. The proportion of cells actively proliferating in malignant tumours is generally greater than that of normal cells. Malignant cells have no enclosing capsule; thus they invade adjacent or surrounding tissue.

Spread of Cancer:

It has been calculated in general that a tumour mass will double in size 30 times before it is 1 cm in size, when there is a chance for clinical detection by conventional means. The rate of growth of a malignant neoplasm determines its capacity to spread. Cancer may spread by direct extension, by gravitational metastasis, or by metastatic spread.

Direct extension or invasion of neighbouring tissue produces the typical local effects of ulcerating, bulky, hemorrhagic masses or indurative, fibrosing lesions with tissue fixation, distortion of structure, and pitting of the skin seen in some breast cancer. Infection may accompany this spread.

Gravitational metastasis involves erosion of cancer cells in the body cavities and their dropping onto the serous membrane lining in the cavity.

Metastatic spread occurs when the cancer cells invade vascular or lymphatic channels and travel to distant parts of the body where implantation occurs. In metastatic spread, there is almost always a high degree of histologic, cytologic, and functional similarity between the primary cancer and these metastases. Consequently, the type of cell and probable site of the primary tumour can be identified from the morphology of the metastasies. In addition, the mestastes usually mimic the primary tumour in the formation of cell products and secretions.

Anaplasia should result in the modification of the transmission, absorption, and reflection properties of tissue 50 GHz–40 THz frequency range which can be studied by the method of the present invention. The loss of differentiation and additional ulcerating, bulky, hemorhagic masses or indurative, fibrosing lesions with tissue fixation, distortion of structure will modify properties such as the refractive index, the thickness of the tissue, etc, which can be imaged by a method of the present invention.

Taking the refractive index, for a given thickness, the probability of interaction between radiation and tissue is dependent on the density of the material. The appearance of fibrous material and additional (mutated) cells in a tumorous region suggests that the density of the tissue in this region will be modified relative to that of healthy tissue, leading to a density change. This in turn should modify the refractive index of the medium (either at a fixed frequency $\omega$ or over a range of frequencies) relative to that in normal tissue. These changes in the refractive index can be detected by either 1) simply, by shifts in the time domain of a transmitted or reflected THz pulse or 2) least squares fits to frequency domain information, which will yield the refractive index at each frequency $\eta(\omega)$. In the cancerous regions, we expect increases in the refractive index due to increases in the density of cells in that region. However, exclusion of water in the cancer will also modify the refractive index. Due to either effect, the refractive index at different pixels in the image can be used as a contrast mechanism.

Changes in thickness d between abnormal and normal tissue will lead to changes in either a) the absorption in a given region $a(\omega)d$ or b) the time delay of the pulse in that region $\eta(\omega)d$.

Both a) and b) can be determined using electric field and time domain spectra, respectively, forming the basis of a contrast mechanism. Because malignant cancer grows rapidly relative to the tissue which it invades, it is likely that a malignant turnout and the normal tissue adjacent to it will differ appreciably in thickness, which can be determined by the methods of the present invention using a) and/or b) above.

For a given thickness, the probability of interaction between radiation and tissue is dependent on the density of the material. The appearance of fibrous material and additional (mutated) cells in a tumourous region suggests that the density of the tissue in this region will be modified relative to that of healthy tissue, leading to a density change between normal and cancerous tissue. The linear attenuation coefficient $a(\omega)$ (usually quoted in units of $cm^{-1}$) is dependent on the density of the material. Thus, if a tumour represents a larger amount of tissue in the same volume, the linear attenuation coefficient $a(\omega)$ will increases proportionally to the increase in density. For a given thickness, this change will manifest itself as increased absorption in the tumour relative to the normal tissue.

Convolved with such density-induced changes in $a(\omega)$ will be variations in $\alpha(\omega)$ due to changes in the composition of the tissue itself. Changes in chemical composition are the most obvious reason for this. For example, the presence of ulcerating bulky, hemorrhagic masses in tumours implies a change in chemical composition relative to healthy tissue. In certain types of malignant tumours such as cytologic anaplasia, there is increased or altered nucleic acid synthesis in growing tissue, which implies a change in chemical content. Moreover, simpler changes such as the exclusion or inclusion of additional water in a tumour will change its chemical composition relative to that of healthy tissue.

$\alpha(\omega)$ may also change in the THz range due to increased disorder in the system. Thus, even if there is no change in the type of molecules in tumourous vs normal tissue, the tumour is likely to be more disordered in terms of the arrangements between cells. A similar phenomenon occurs in liquids, where increasing disorder (or lack of crystallisation) leads to increased absorption. It is therefore probable that $\alpha(\omega)$ will be larger in randomly arranged tumour tissue than in more "regularly arranged" tissues.

The methods of the present invention can also be used to detect increased vascularity around tumours and cancerous regions. As noted in the text above, the increased number of blood vessels necessary to feed a tumour can be a first indication of the appearance of cancer. Therefore, detection of increased blood flow or the increased presence of blood in a certain region can be used for the detection of cancer.

In the fourth aspect, the present invention provides a method for detecting cancer, the method comprising the steps of:

a) irradiating the sample with pulsed electromagnetic radiation with a plurality of frequencies in the range from 50 GHz to 84 THz;

b) subdividing an area of the sample into a two dimensional array of pixels, and detecting radiation from each pixel over a plurality of frequencies;

c) generating an image of the area of the sample from the radiation detected in step (b).

The imaging step (c) can be generated in a number of ways. For example, it can be generated by plotting the refractive index of the sample for each pixel or it can be generated by plotting the absorption coefficient. Simpler ways to obtain the image would be to plot either the maxima or minima of the electric field or even the time of flight of the radiation through the sample, which would give crucial information about the thickness of the tumour.

The method could also comprise a step of analysing the detected radiation for the presence of lime in the sample. For example, this could be done by obtaining an image of the sample at a frequency where lime is known to strongly absorb. Or, it could be achieved by looking at the individual spectra of the image to isolate the lime fingerprint in the THz region.

The method may also comprise a step of analysing the water content in the sample. This again could be done by looking at the absorption frequencies for water. The image could be stepped through a plurality of different frequencies where water is known to strongly absorb to obtain an accurate result. The method can be used for imaging breast cancer or imaging tumours in human skin. It can also be applied to any type of tumour.

In practice, usually, a reference signal will be taken from a healthy part of the sample in order to compare with the tumourous tissue.

Further aspects of the present invention provide apparatus for effecting the methods, respectively, of the first, second and third aspects of the present invention, each respectively comprising means for carrying-out each of the steps of those methods.

The present invention will now be described by way of example and with reference to the following non-limiting embodiments in which.

Figure 3:
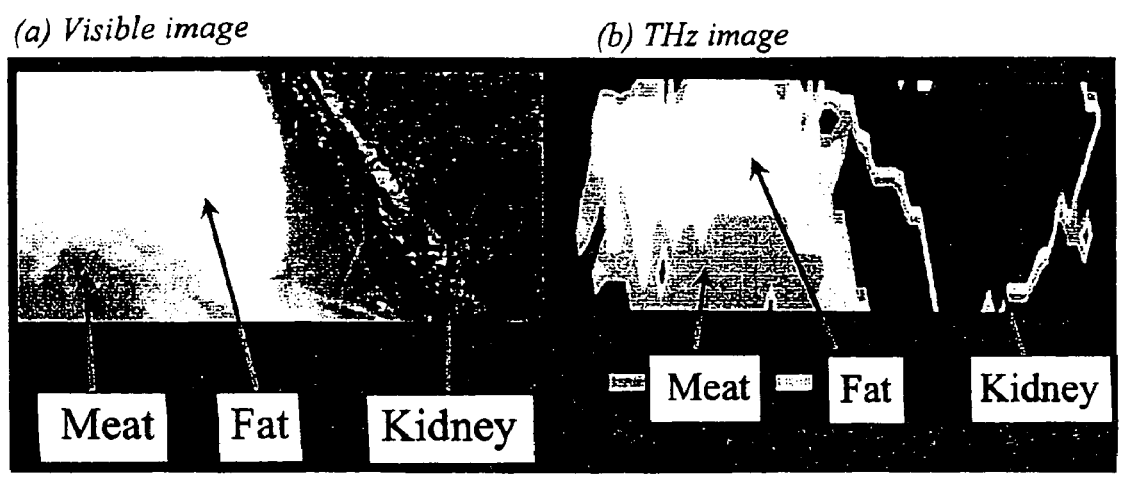
Figure 4:
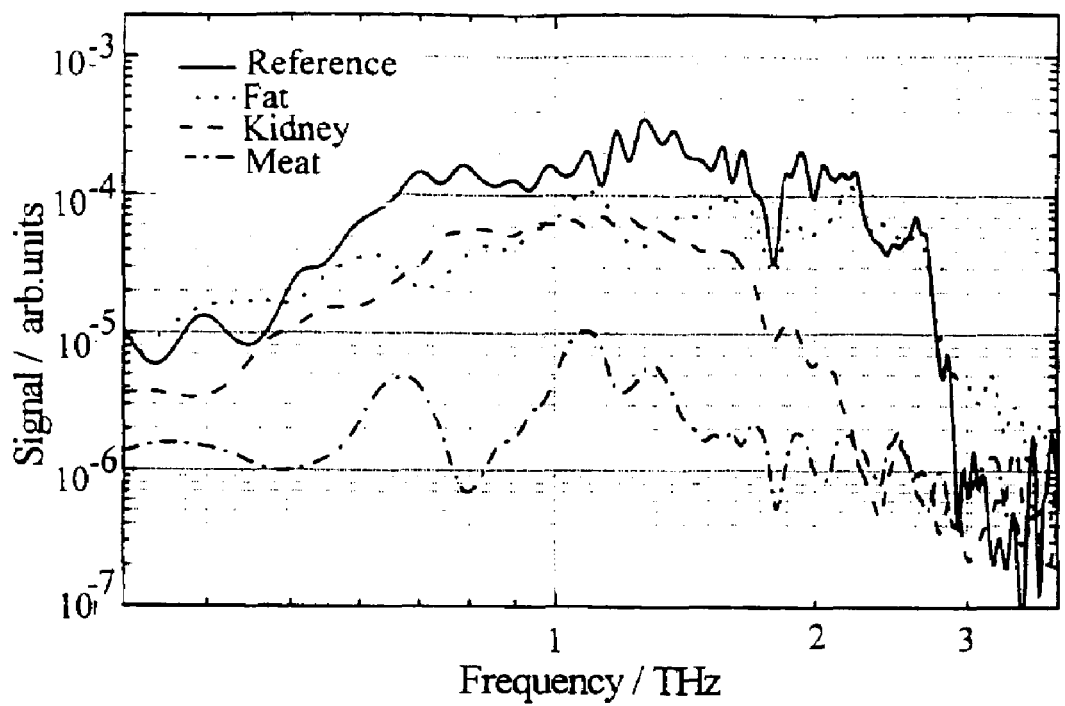

FIG. 3*a* is an image of a pork sample at visible light wavelengths and FIG. 3*b* is the same pork sample at THz frequencies;

FIG. 4 shows three power spectra for different pixels of the image of FIG. 3*b;*

Figure 5:
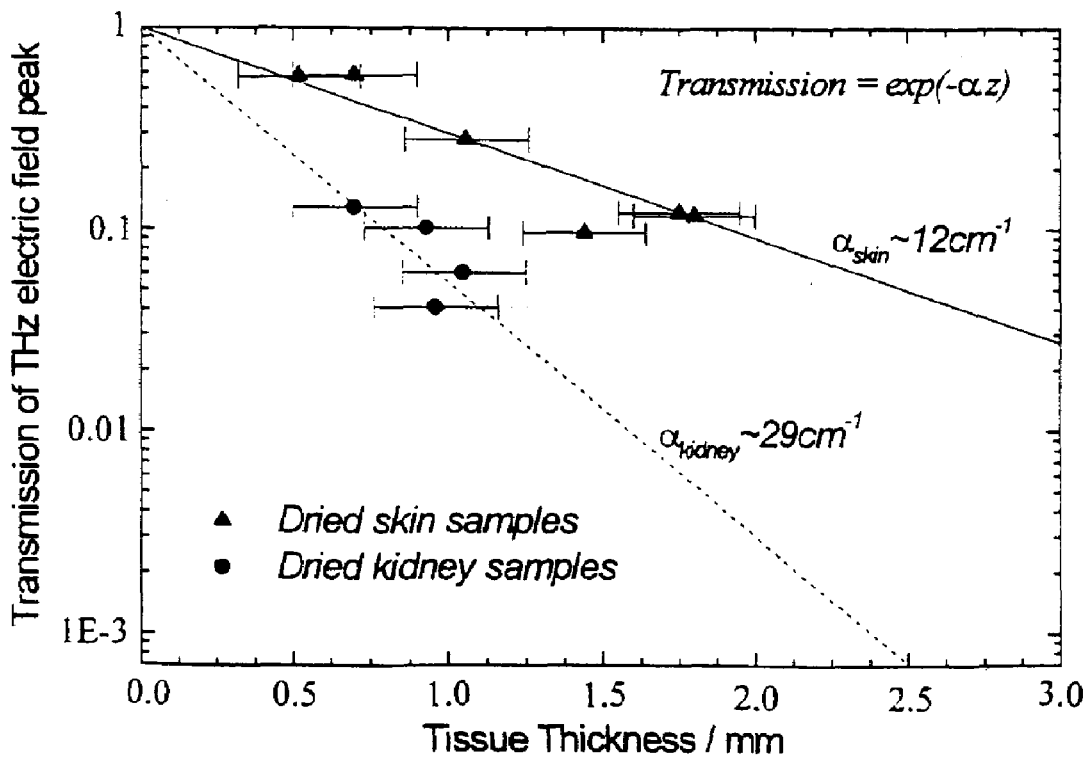
Figure 6:
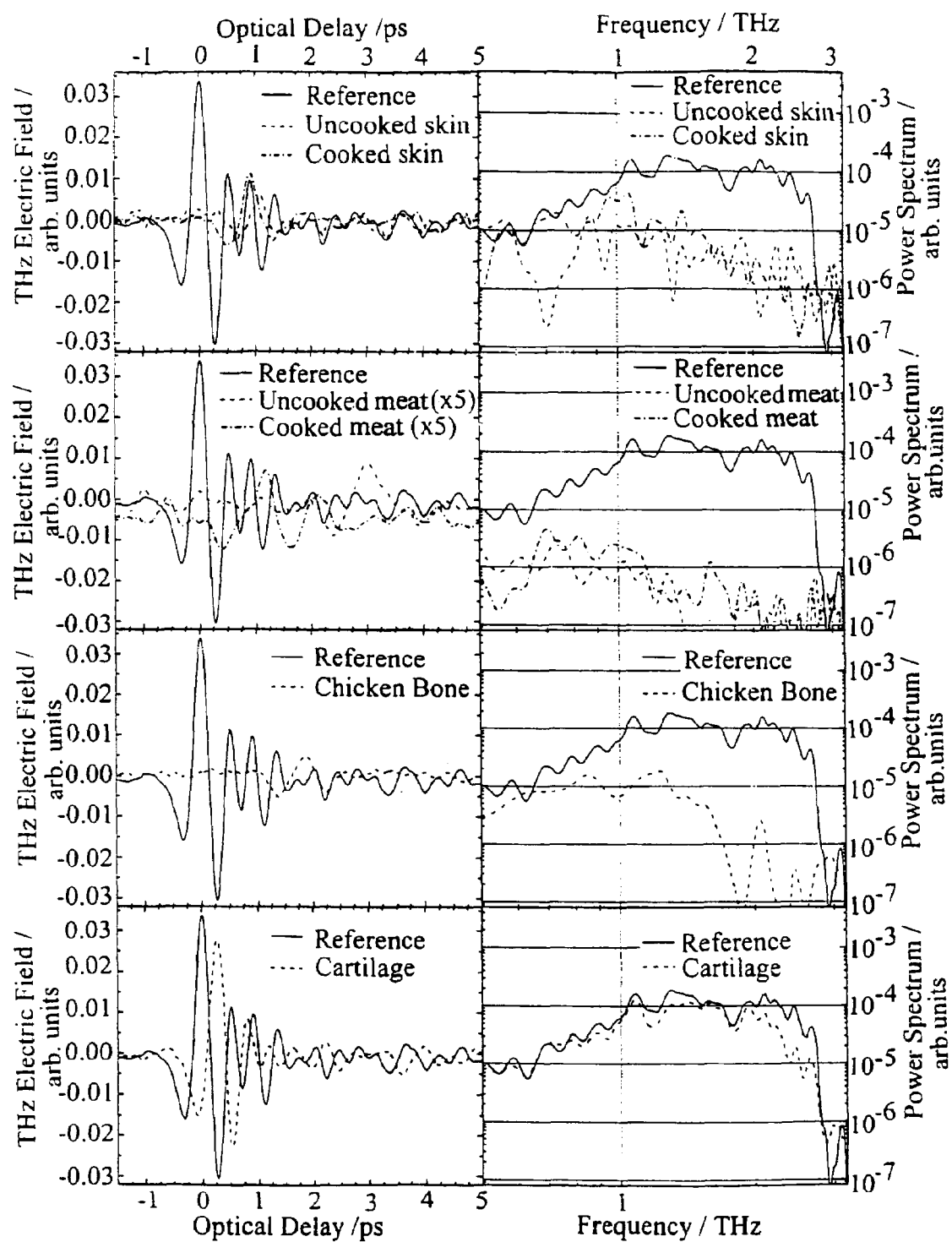
Figure 7:
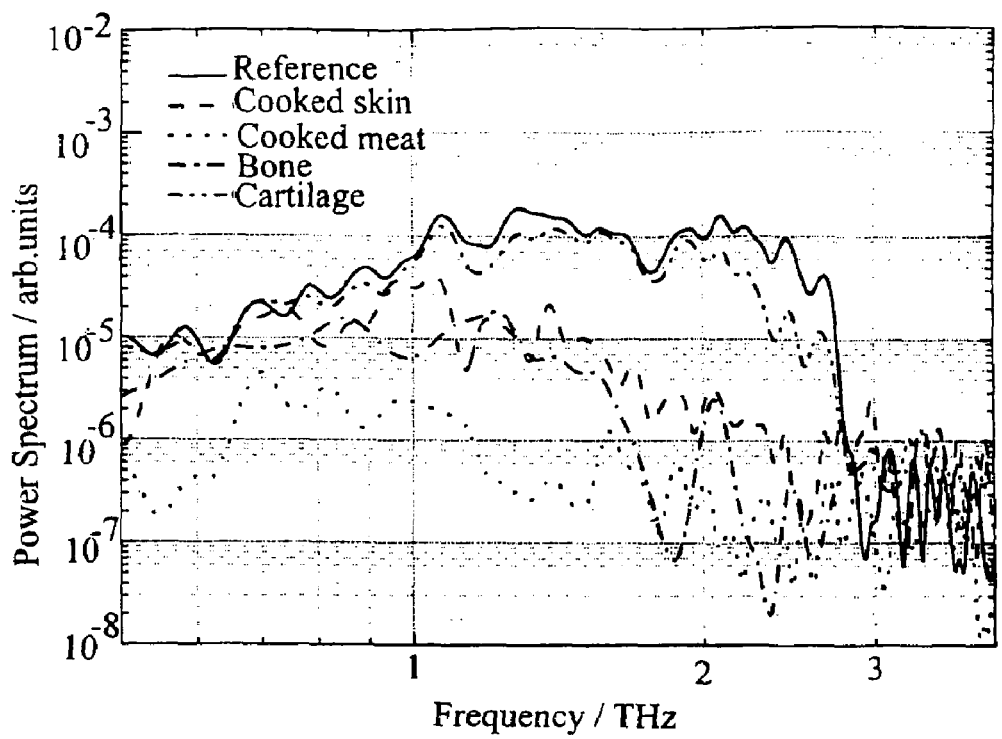
Figure 8:
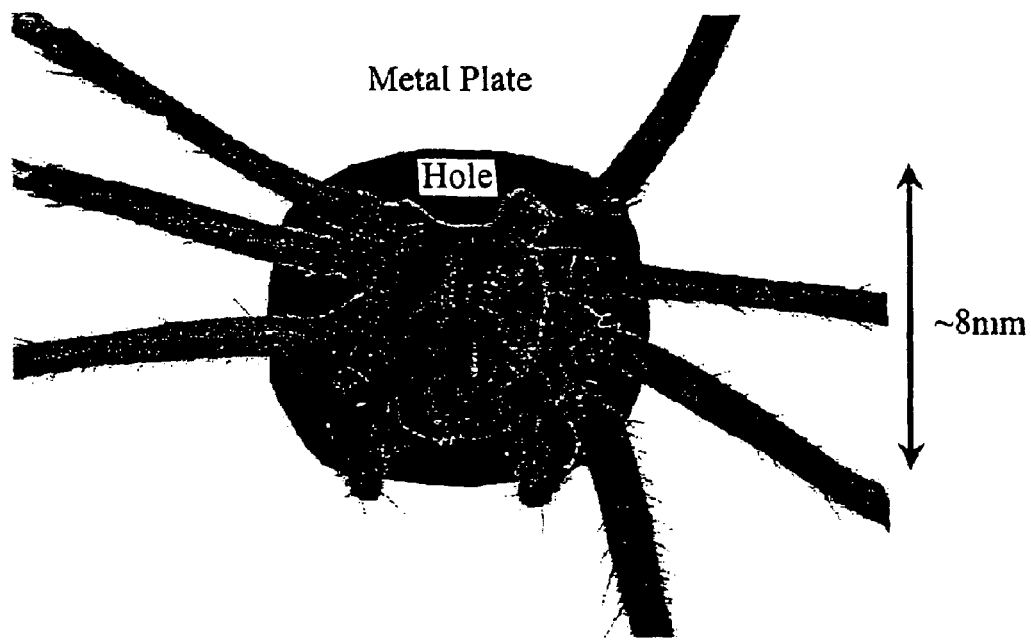
Figure 9:
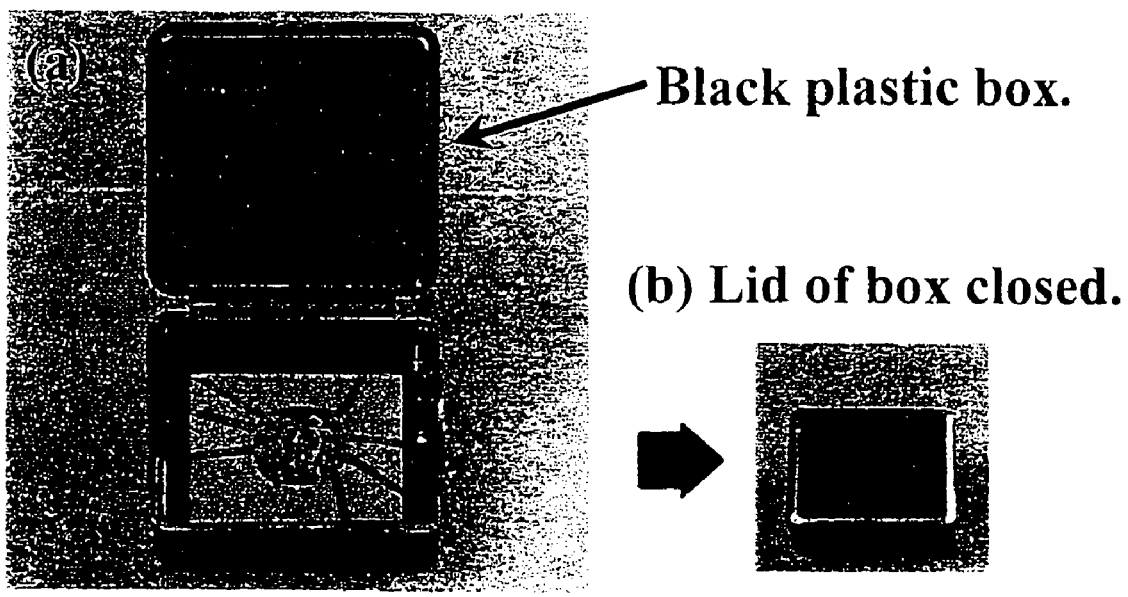
Figure 10:
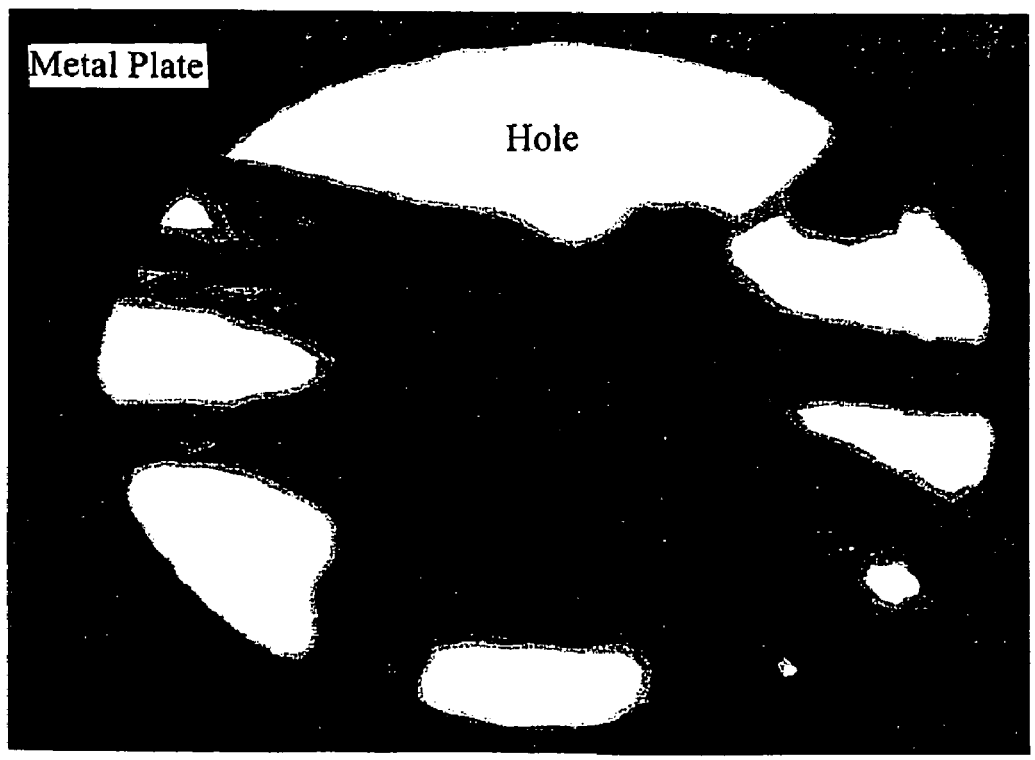

FIG. 5 shows data for absorption coefficient for dried pork skin and dried pork kidney samples;

FIG. 6 shows THz electric field data and time domain and power spectrum frequency domain for different types of chicken tissue;

FIG. 7 shows power spectra obtained from the data of FIG. 6 plotted on a single axis;

FIG. 8 shows a visible image of a spider mounted over a hole in the metal plate;

FIG. 9 shows a visible image of the spider in a box with the box open (FIG. 9*a*) and the box closed (FIG. 9*b*);

FIG. 10 shows the THz image of the spider in the box of FIG. 9*b;*

Figure 11:
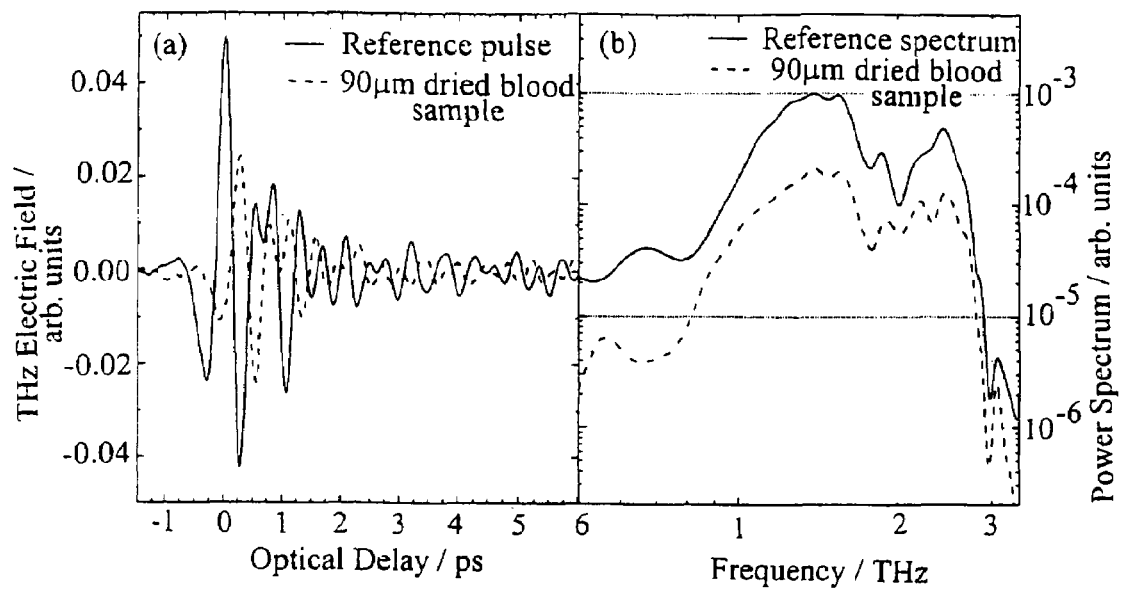
Figure 12:
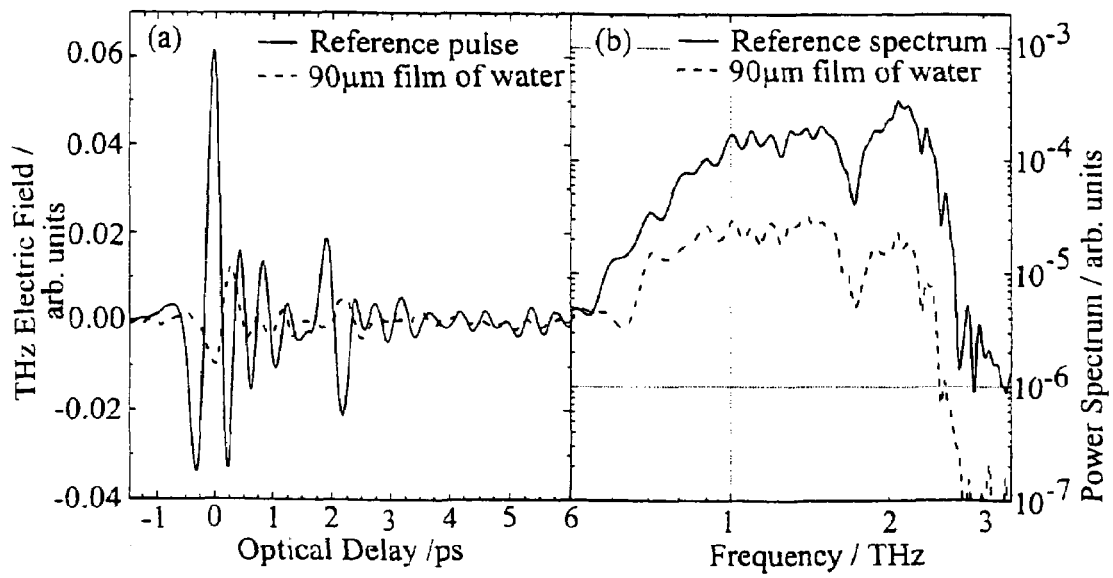

FIG. 11 shows the THz electric field and power spectrum derived from a blood sample;

FIG. 12 shows the THz electric field and power spectra derived from a water sample;

FIG. 13*a* shows a visible image of a commercial package transistor. FIG. 13*b* shows a THz image of FIG. 13*a* and FIG. 13*c* shows a cut away image of the transistor of FIG. 13*a;*

Figure 13:
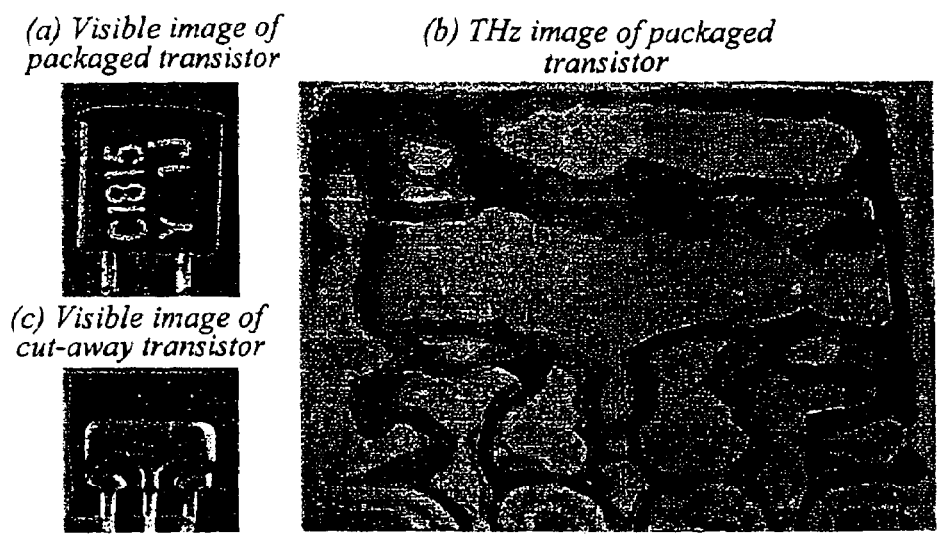
Figure 14:
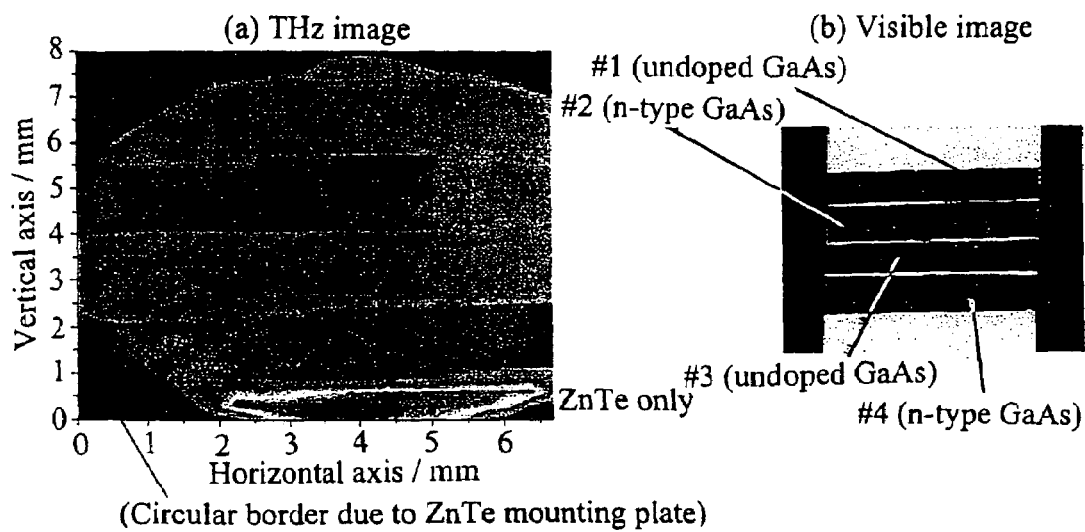
Figure 15A:
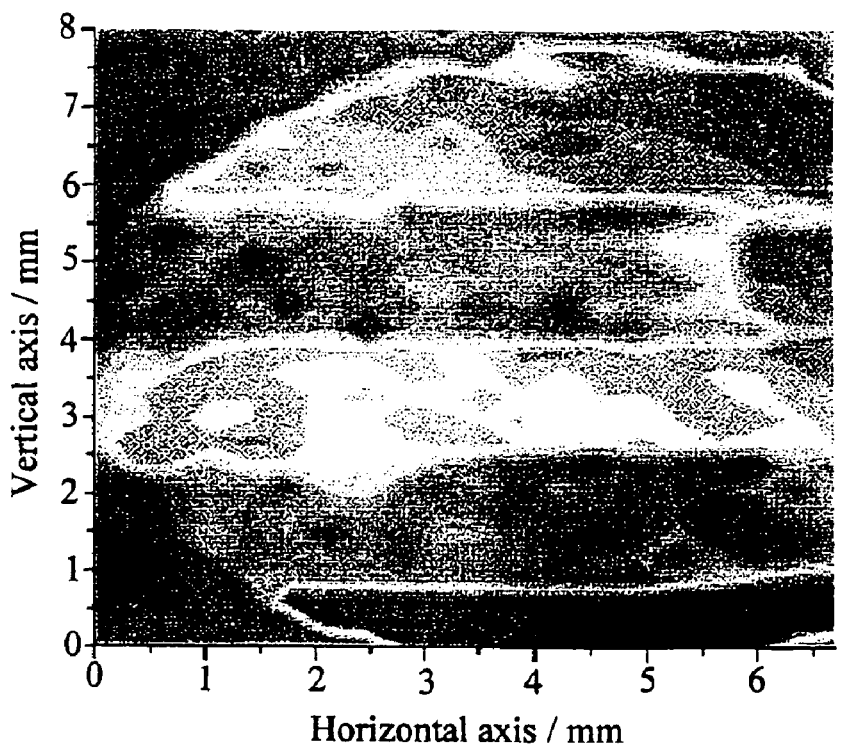
Figure 15B:
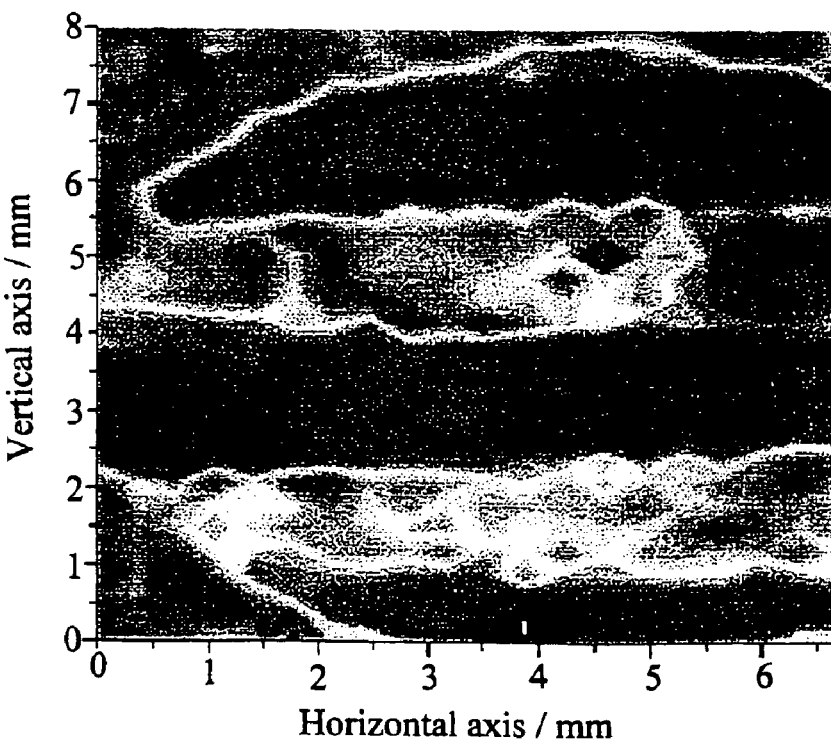
Figure 16:
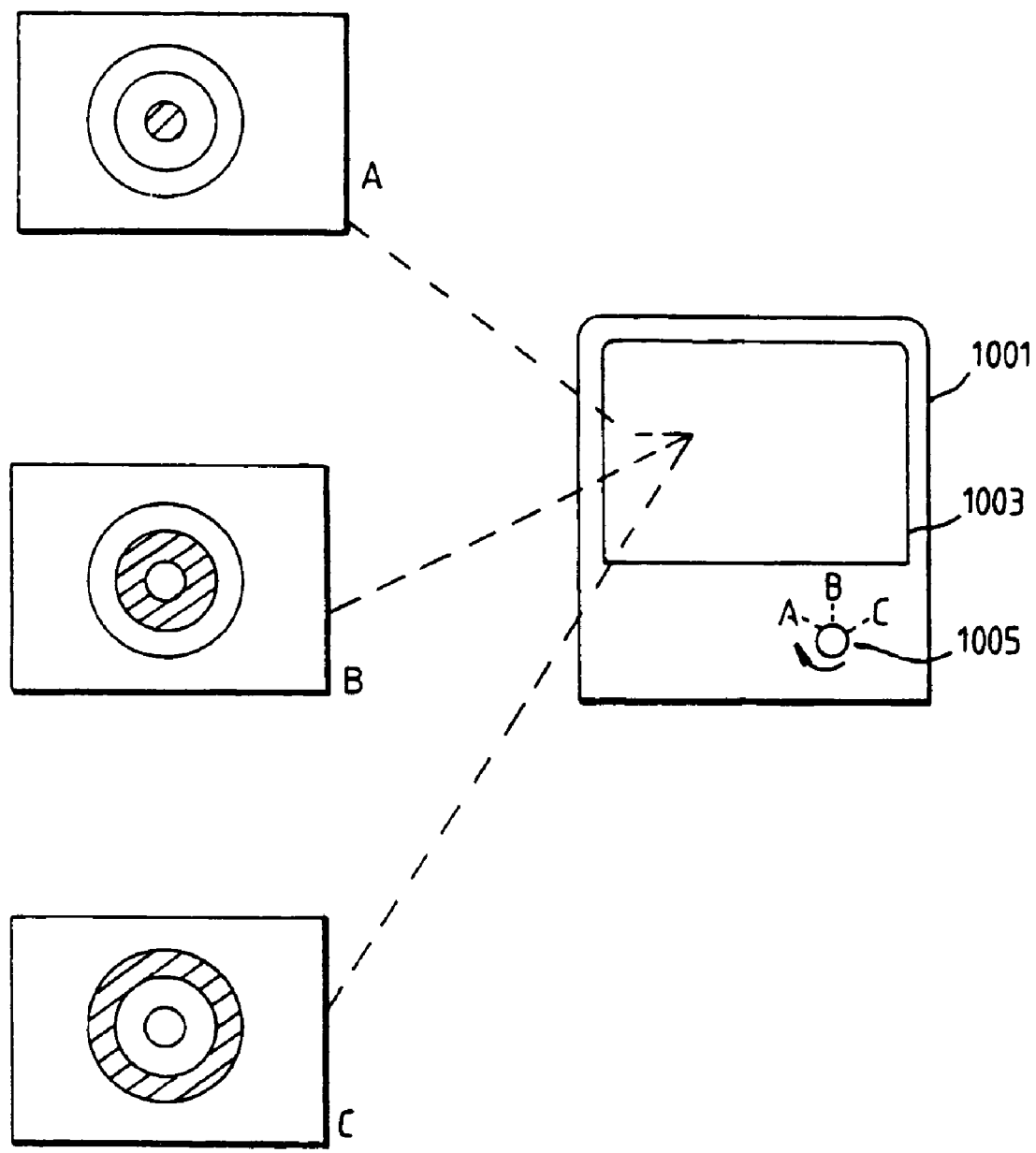
Figure 17:
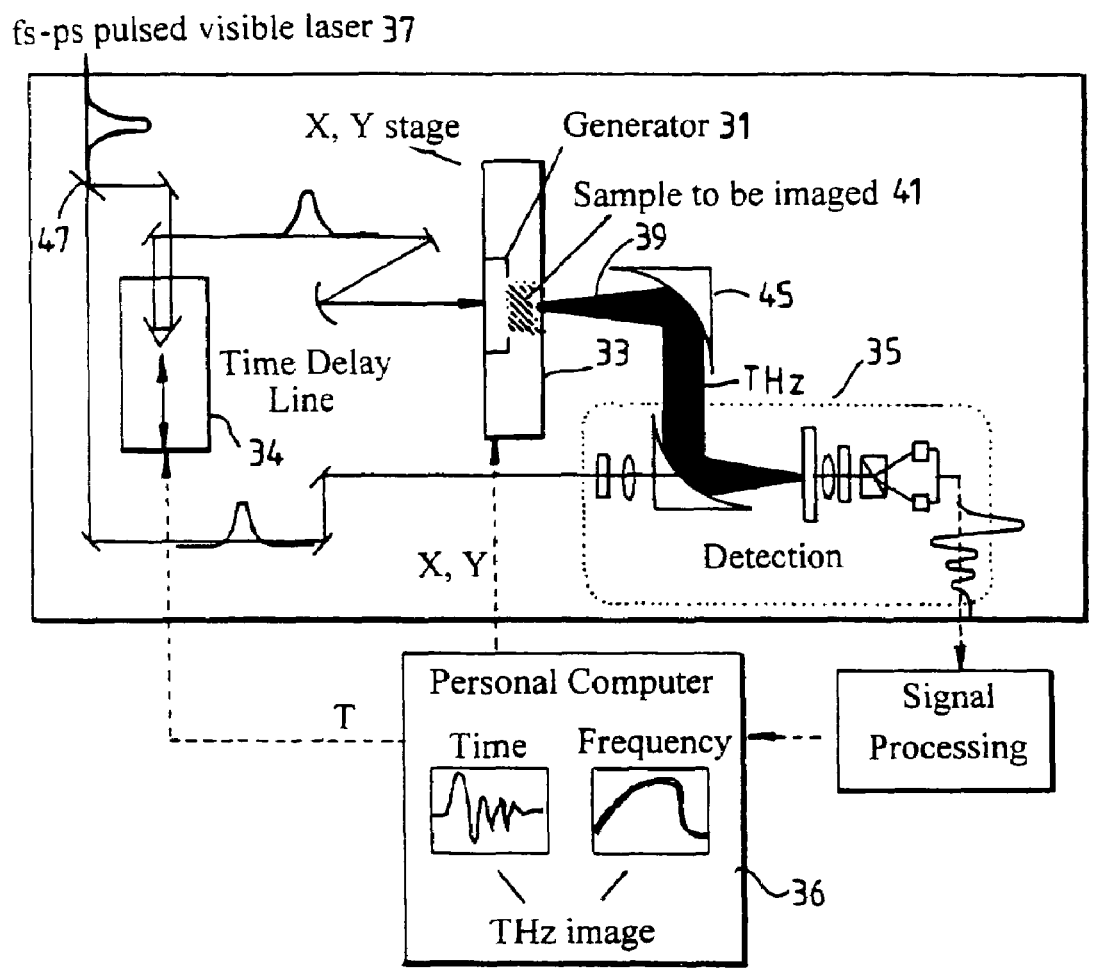
Figure 18:
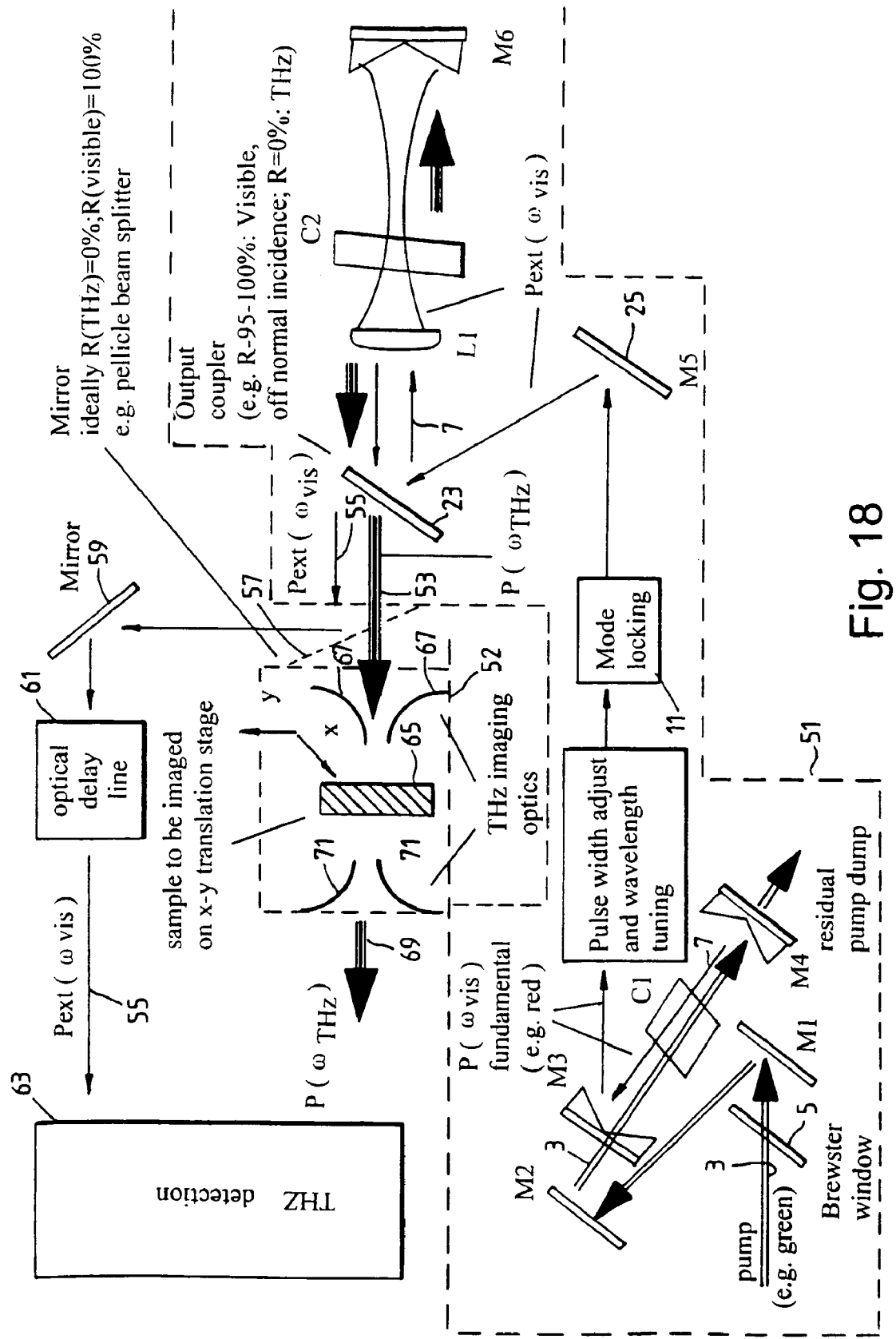
Figure 19:
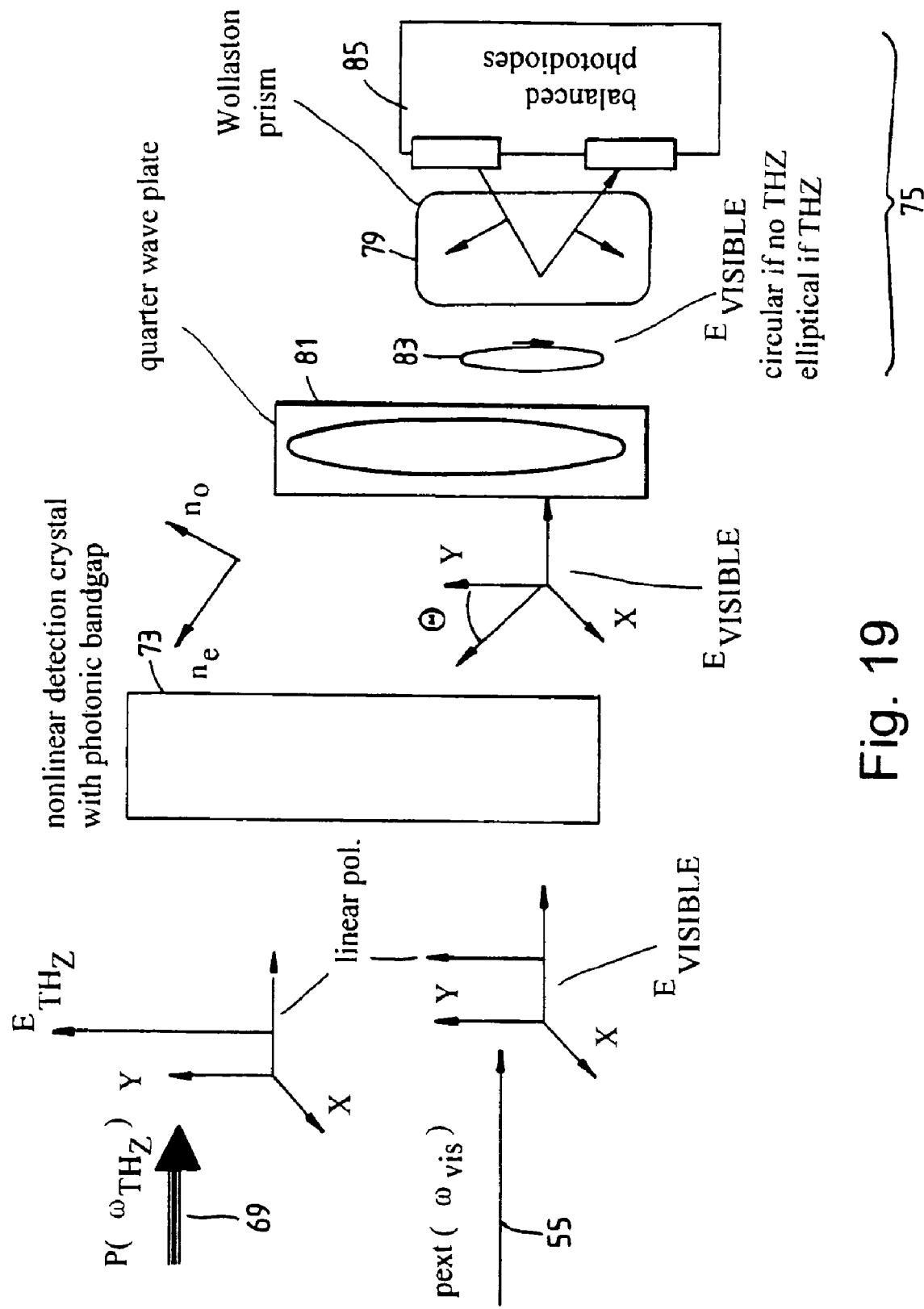
Figure 20:
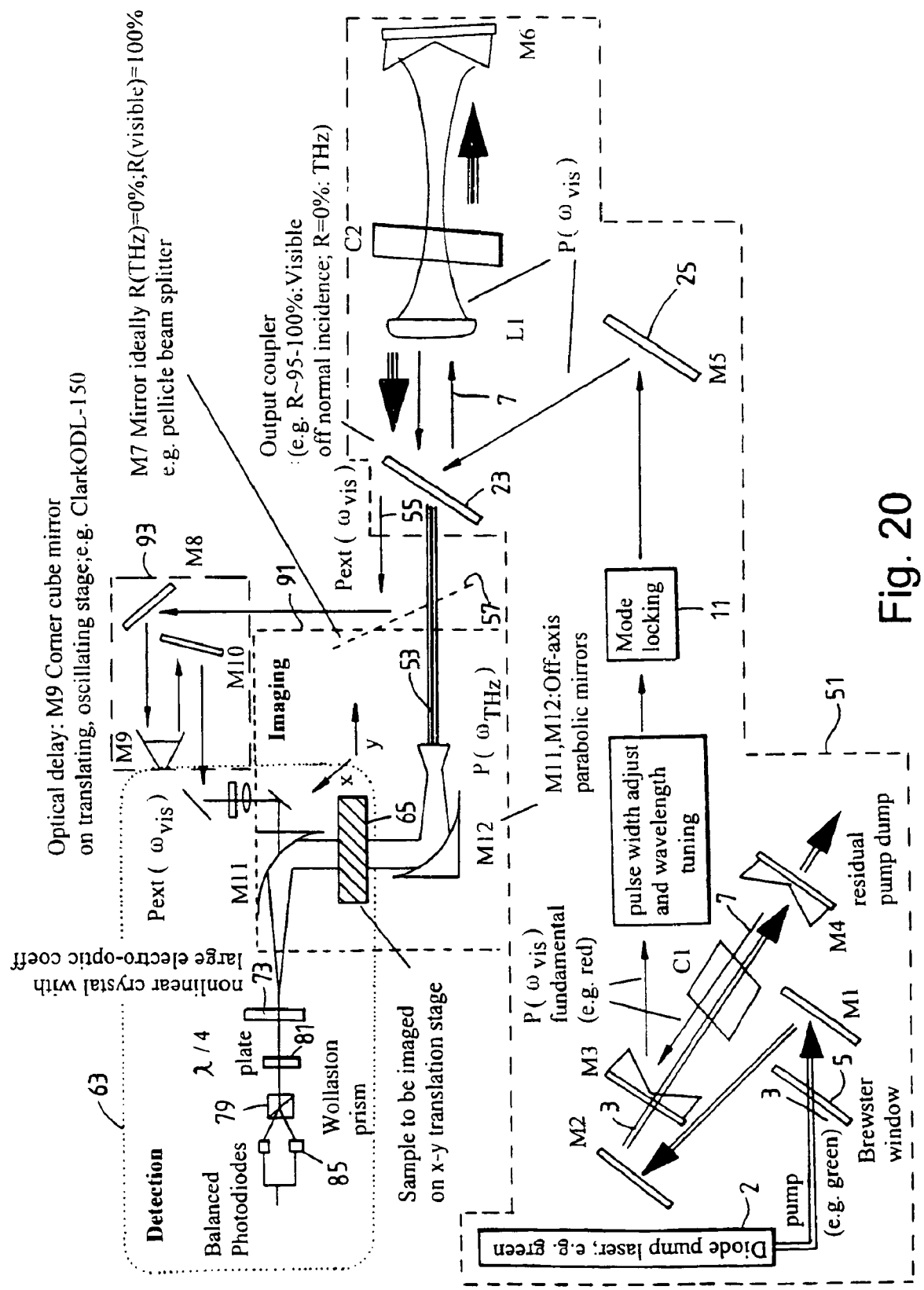
Figure 21:
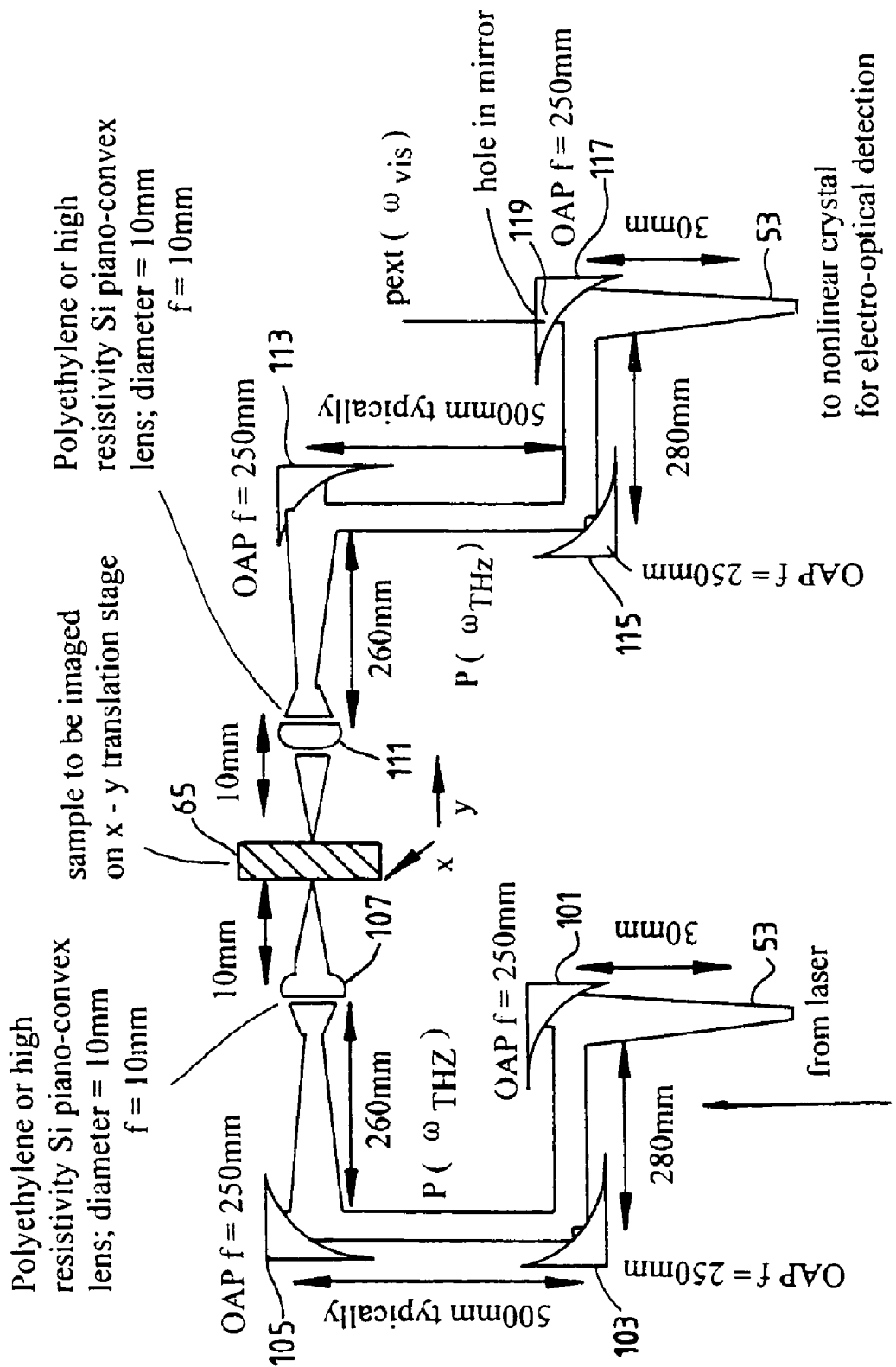
Figure 22:
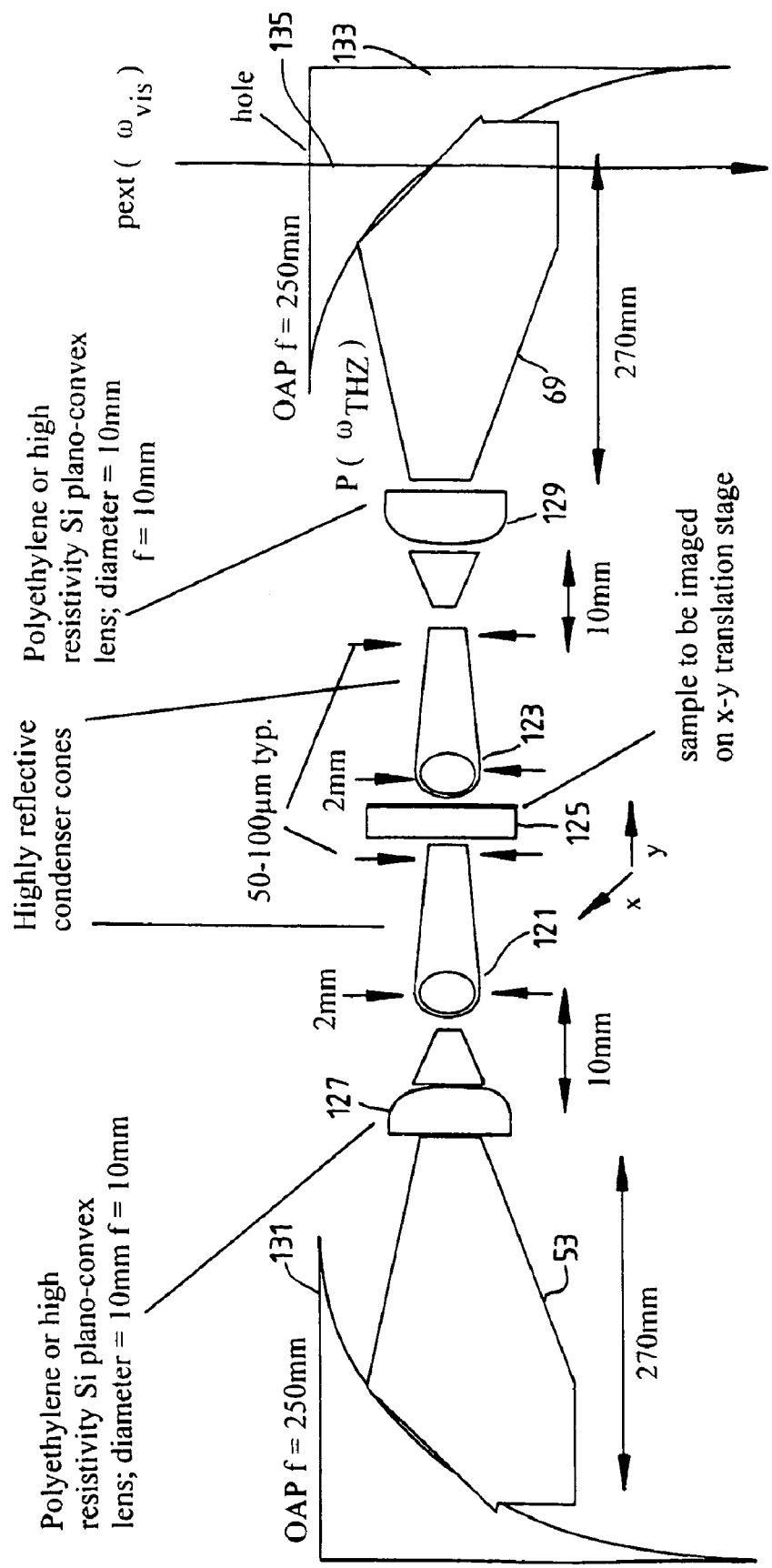
Figure 23:
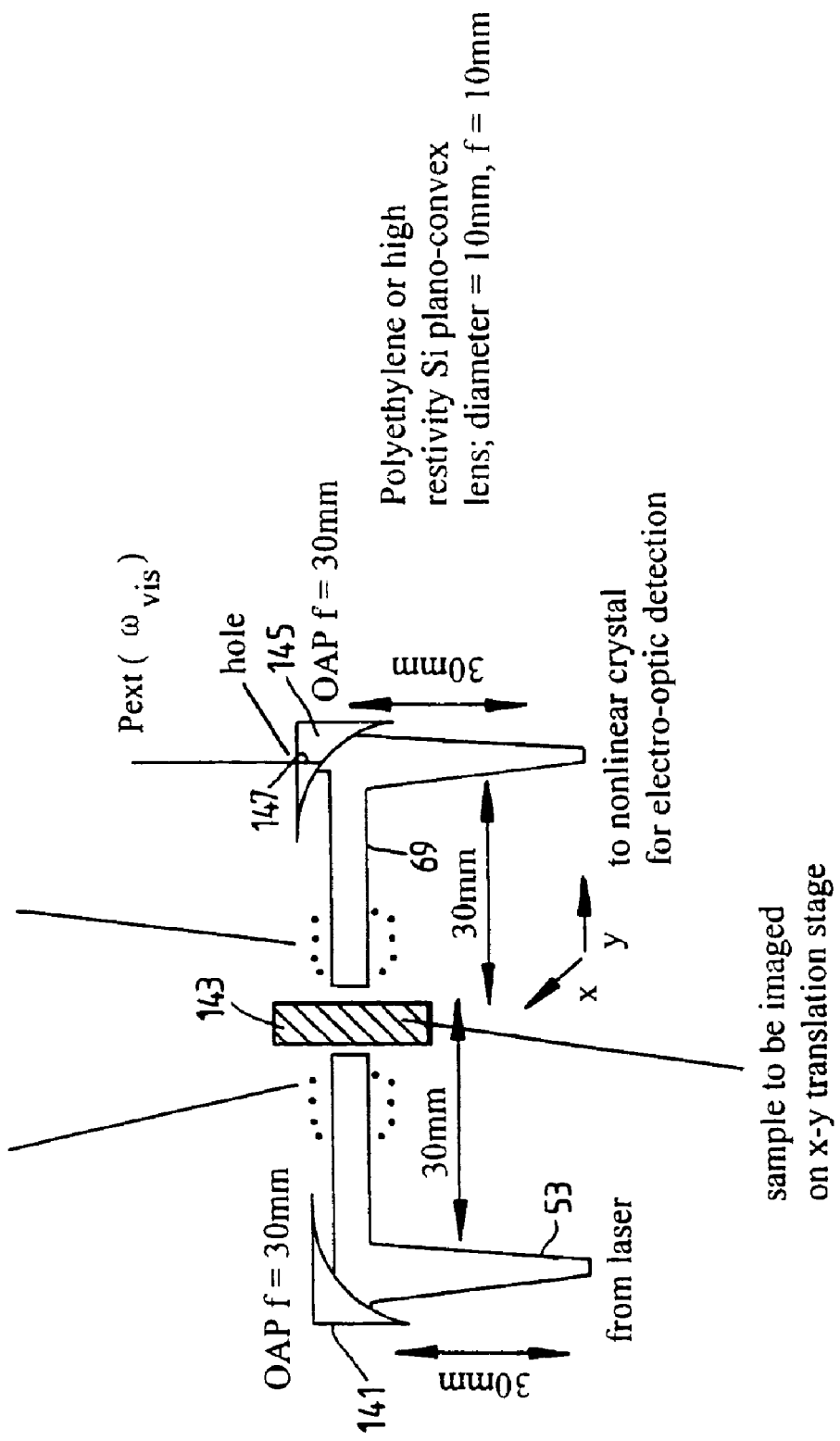
Figure 24:
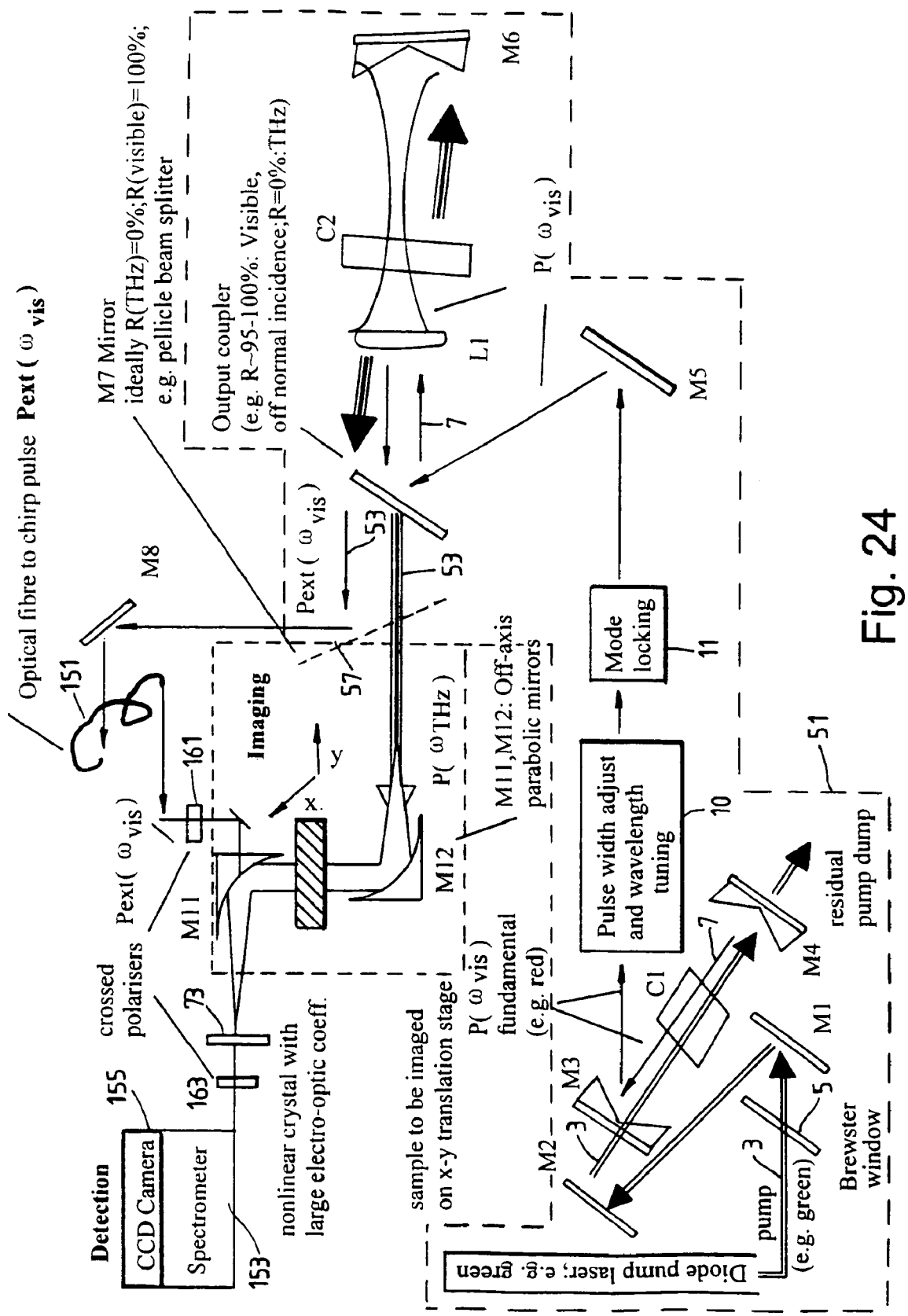

FIG. 14*a* shows the THz image of doped and undoped GaAs. FIG. 14*b* shows the same sample using visible radiation;

FIG. 15*a* shows a monochromatic image of the semiconductor of FIGS. 13 and 14 and FIG. 15*b* shows a monochromatic image similar to FIG. 15 but at a different frequency;

FIG. 16 shows schematic apparatus in accordance with an embodiment of the present invention;

FIG. 17 is a schematic diagram of a THz imaging system;

FIG. 18 shows a variation of imaging system of FIG. 17;

FIG. 19 shows a schematic of a detection section which can be used with the imaging system of FIG. 18;

FIG. 20 shows the imaging system of FIG. 18 with the detection section of FIG. 19;

FIG. 21 shows a variation on the imaging section of FIG. 20;

FIG. 22 shows a variation on the imaging section of FIG. 20;

FIG. 23 shows a variation on the imaging section of FIG. 20;

FIG. 24 shows a further example of an imaging system; and

Figure 25:
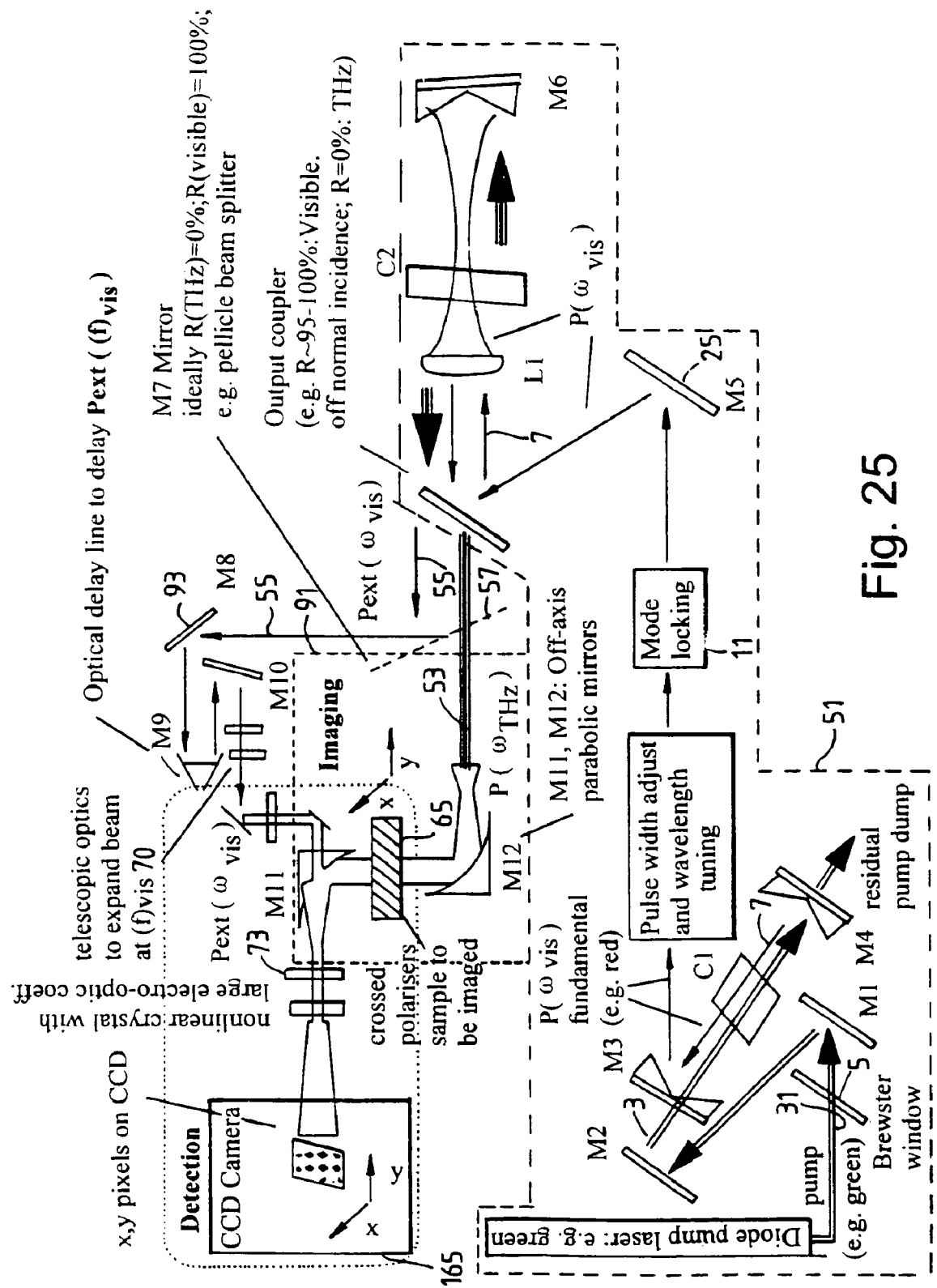

FIG. 25 shows another example of an imaging system.

Figure 26:
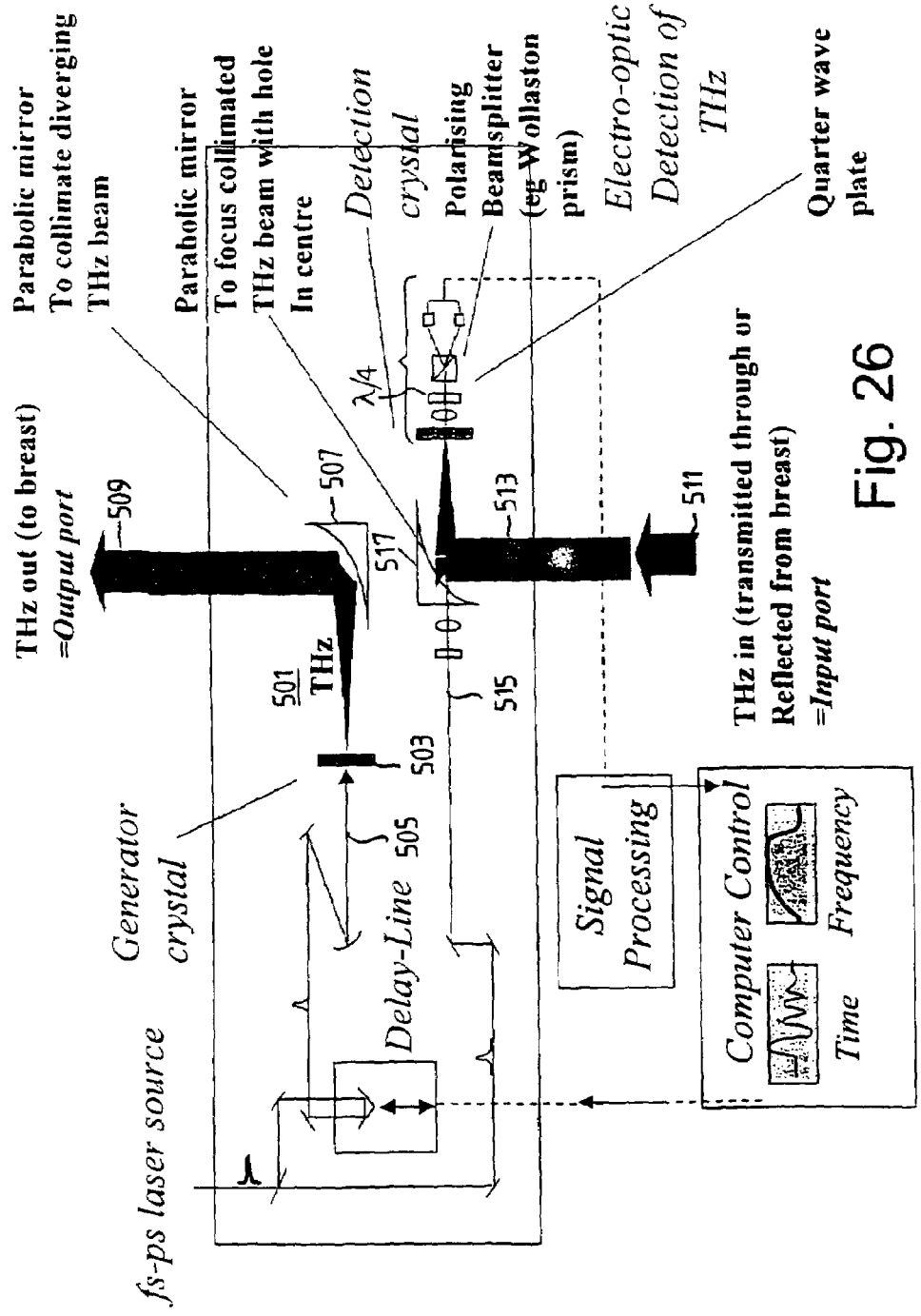
Figure 27:
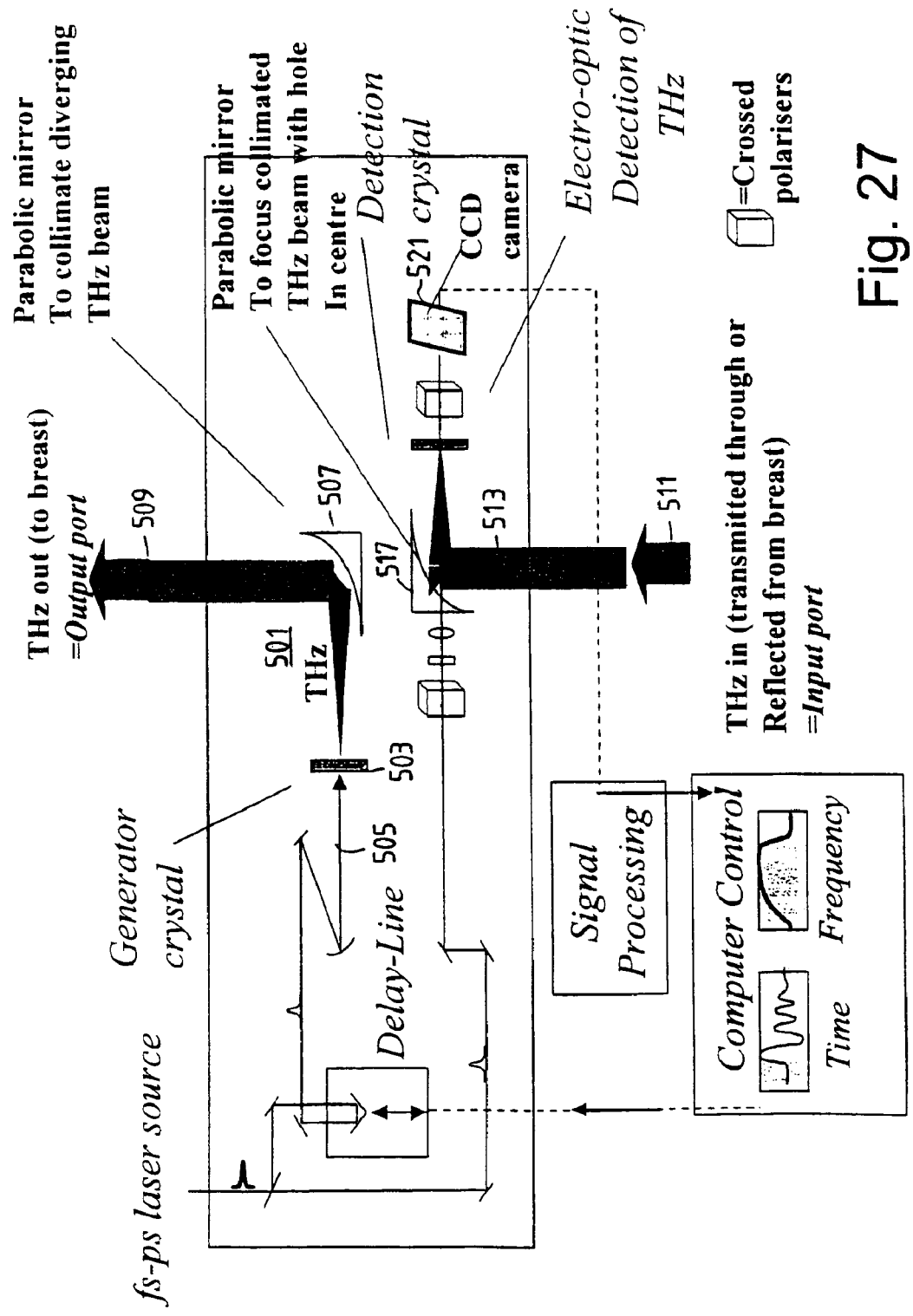
Figure 28:
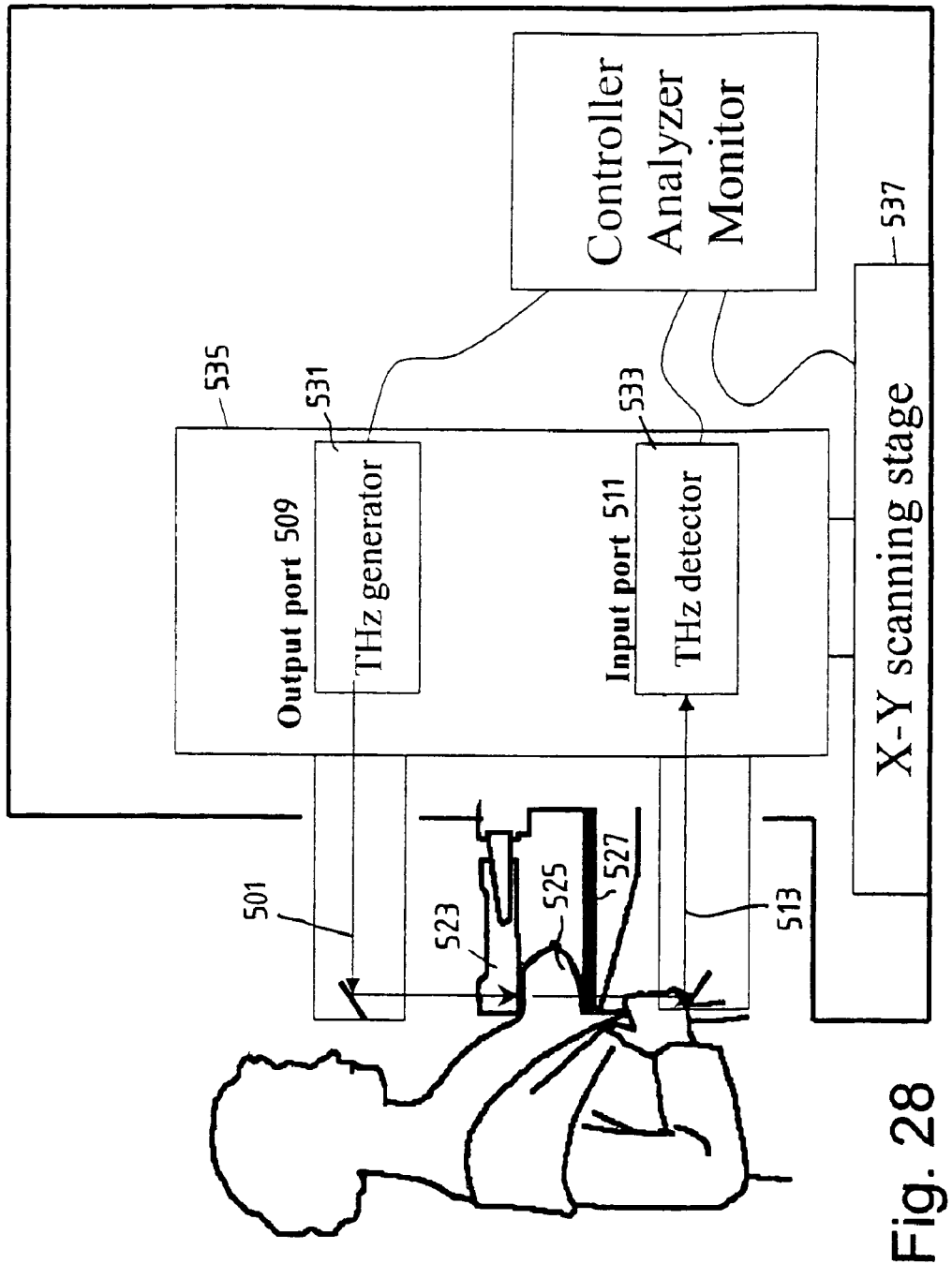
Figure 29:
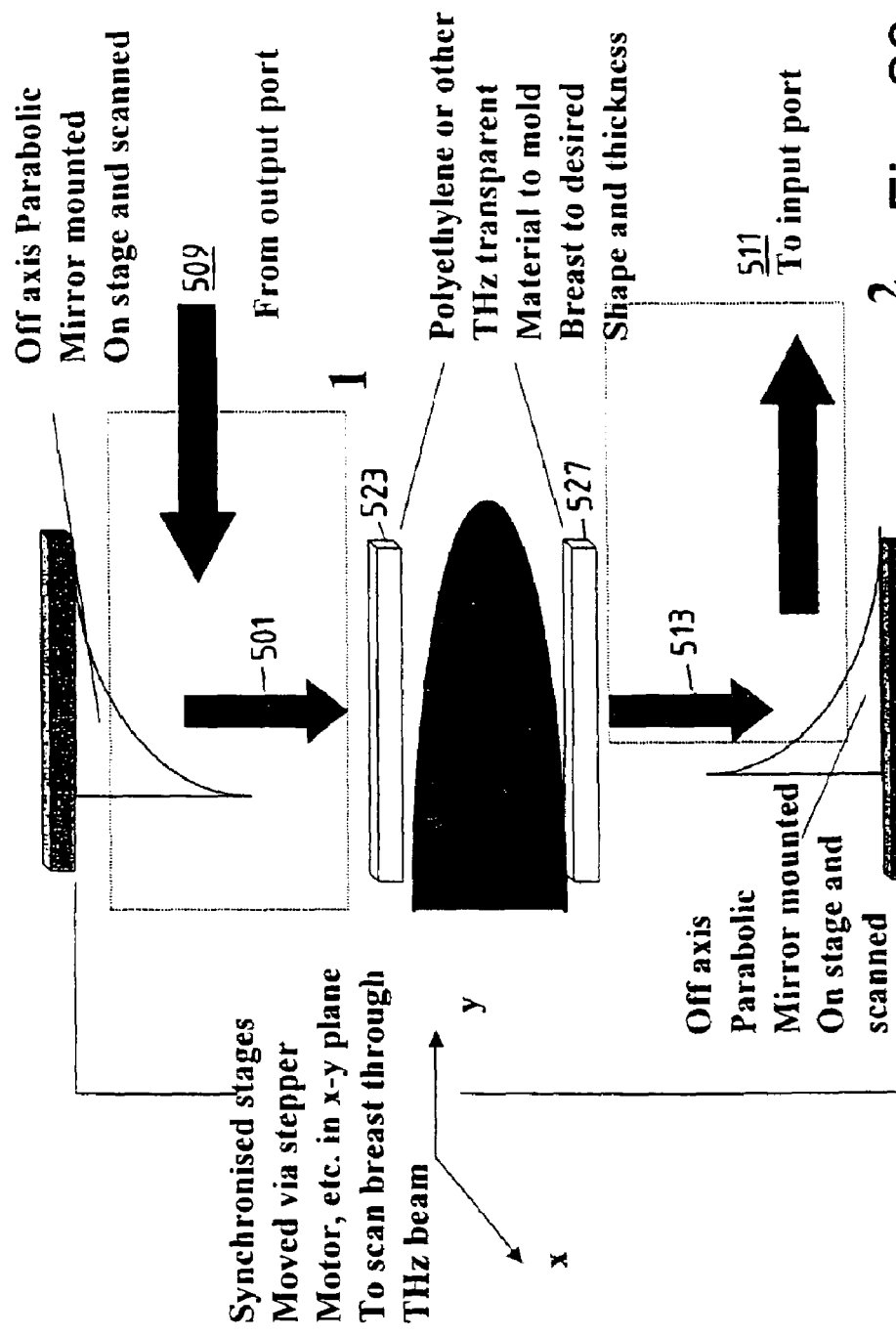
Figure 30:
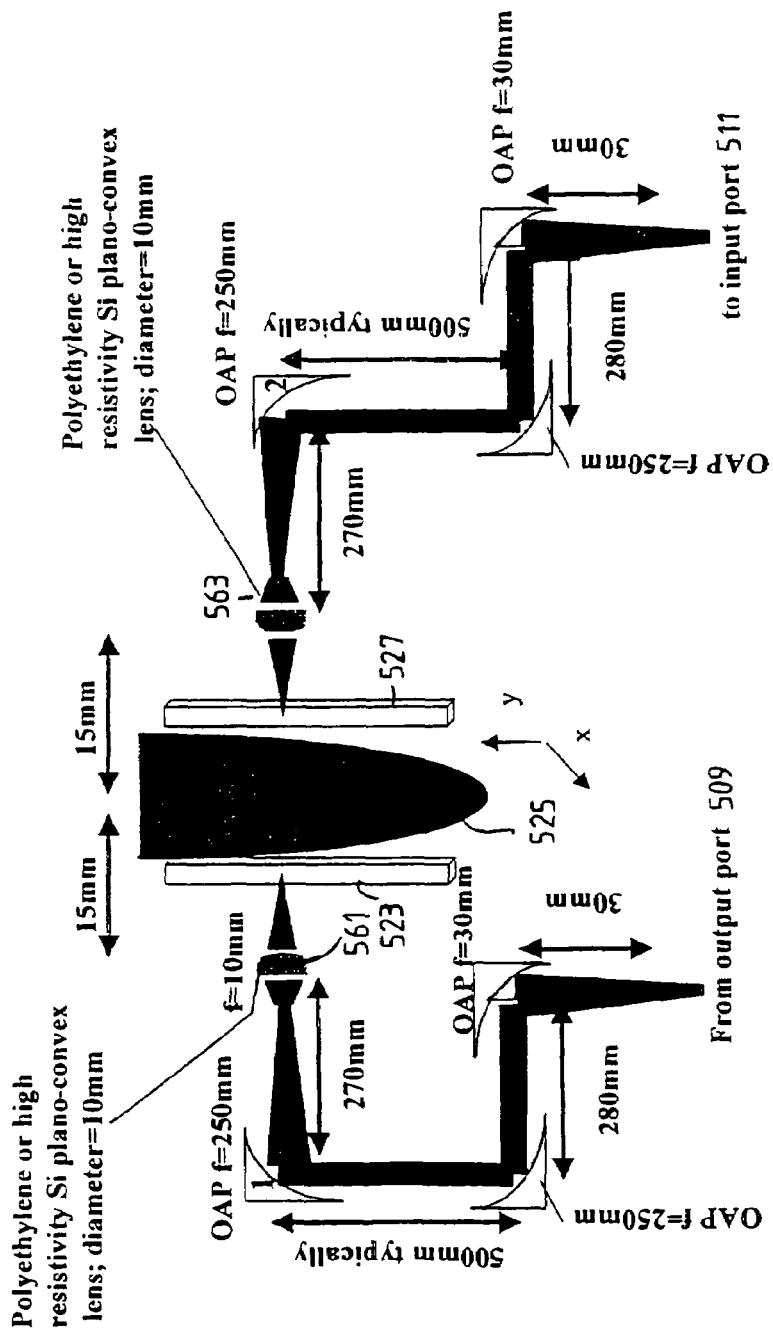
Figure 31:
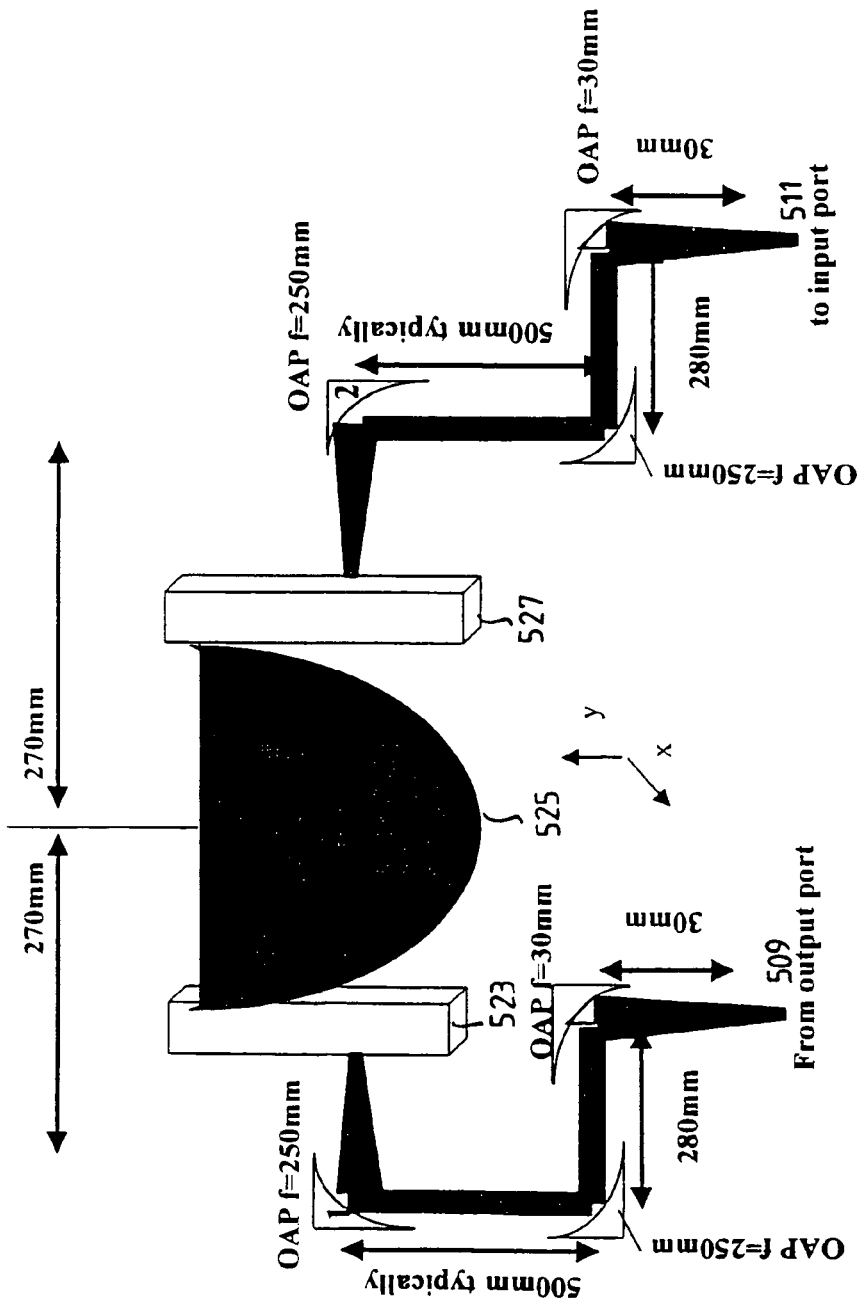
Figure 32:
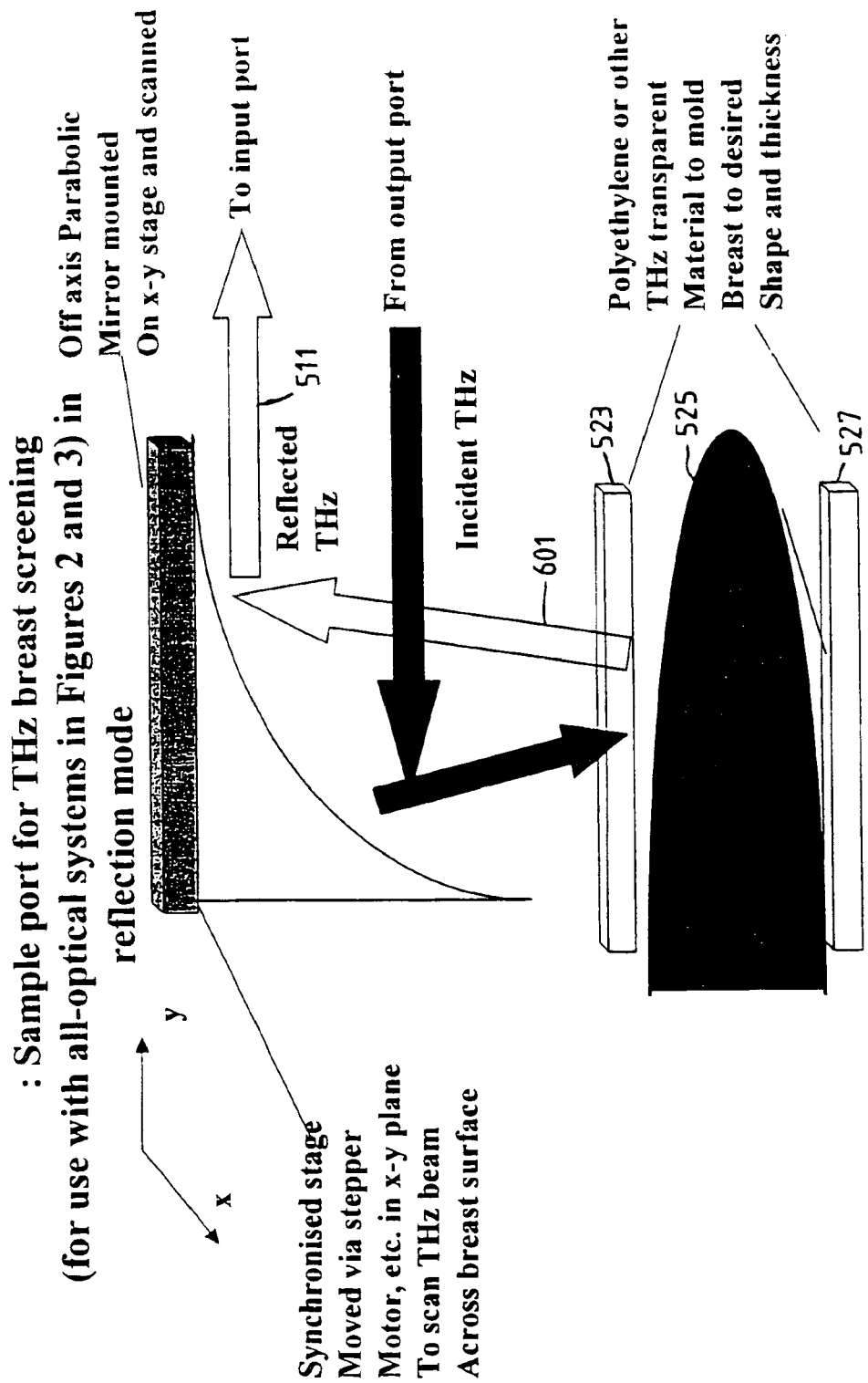
Figure 33:
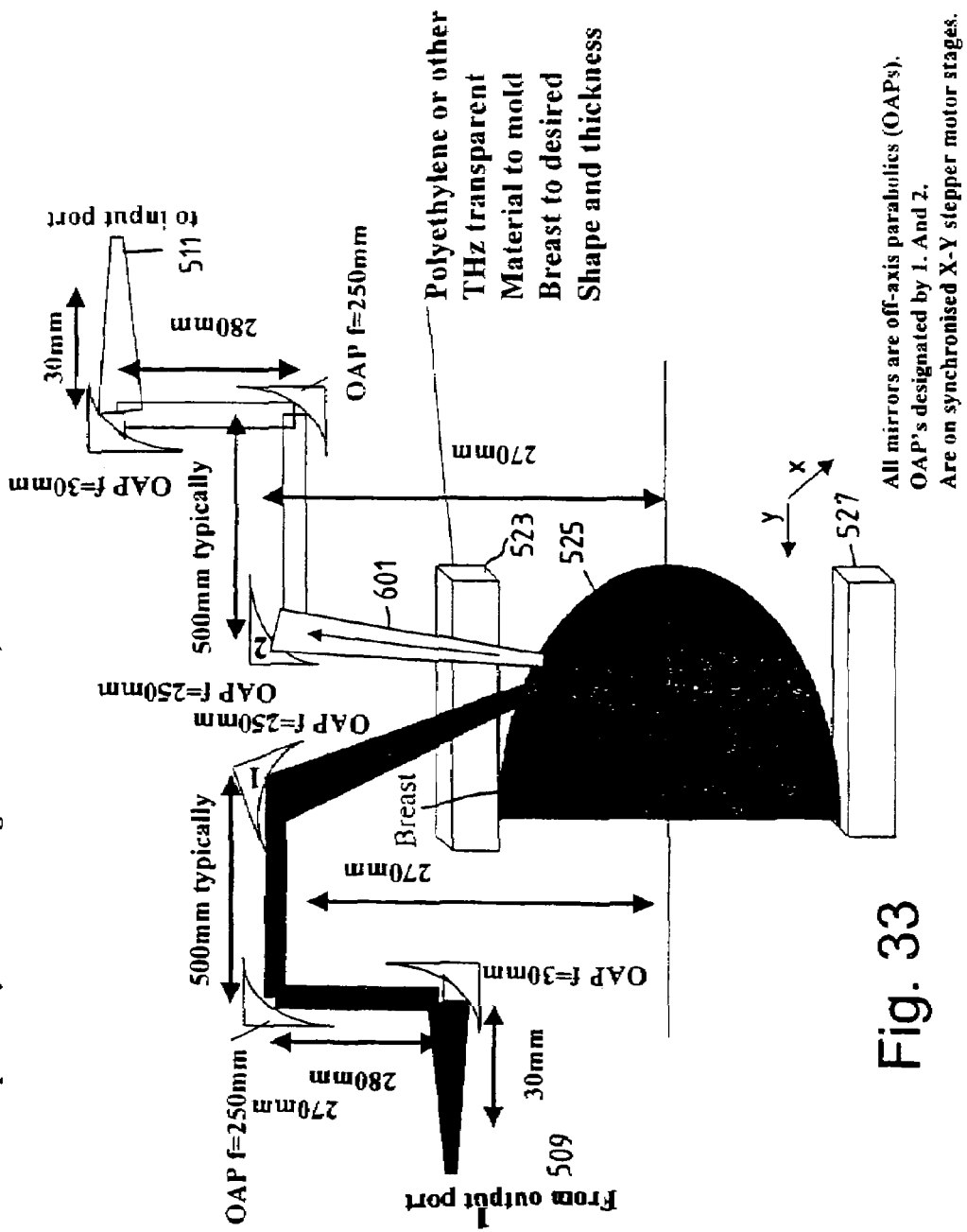
Figure 34:
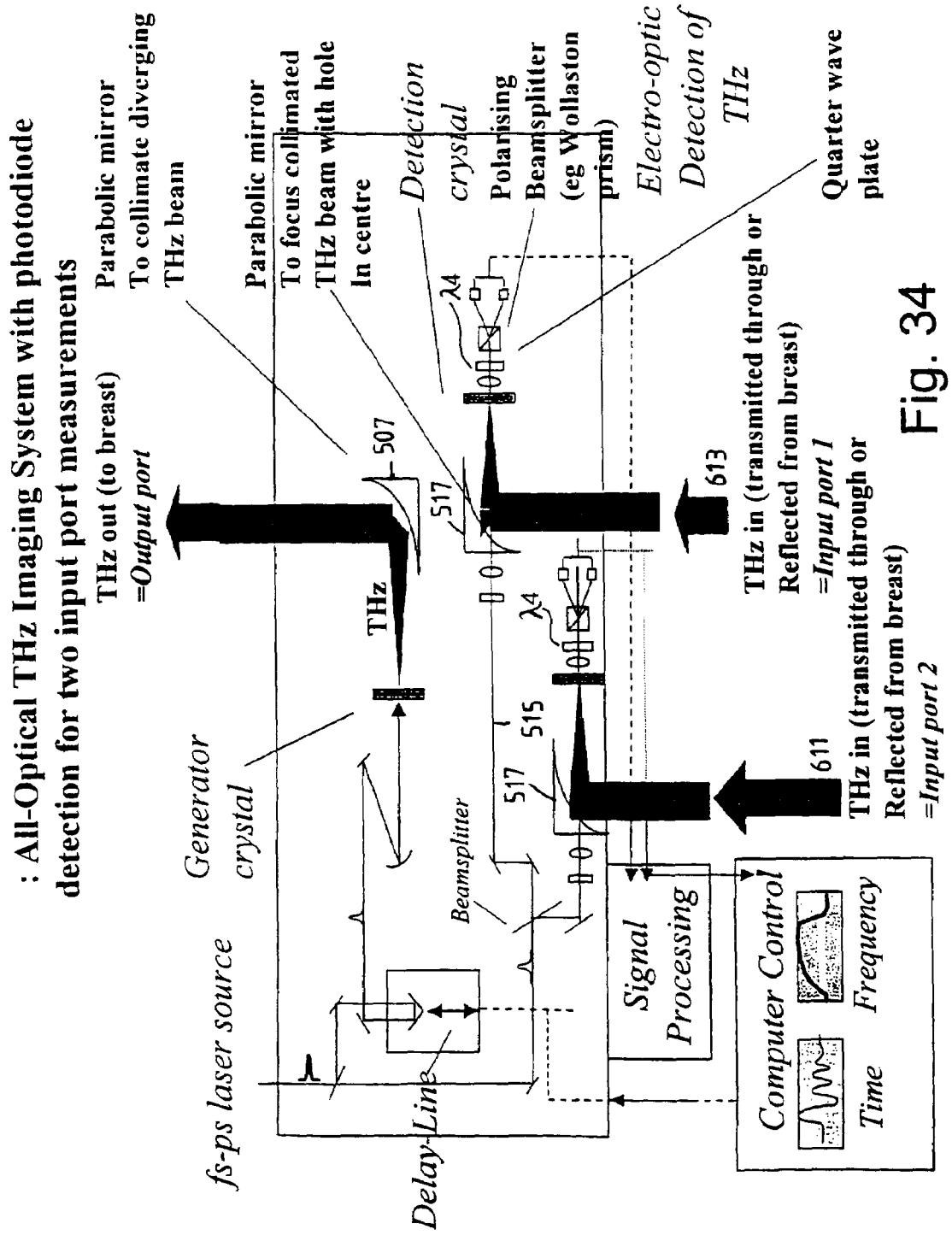
Figure 35:
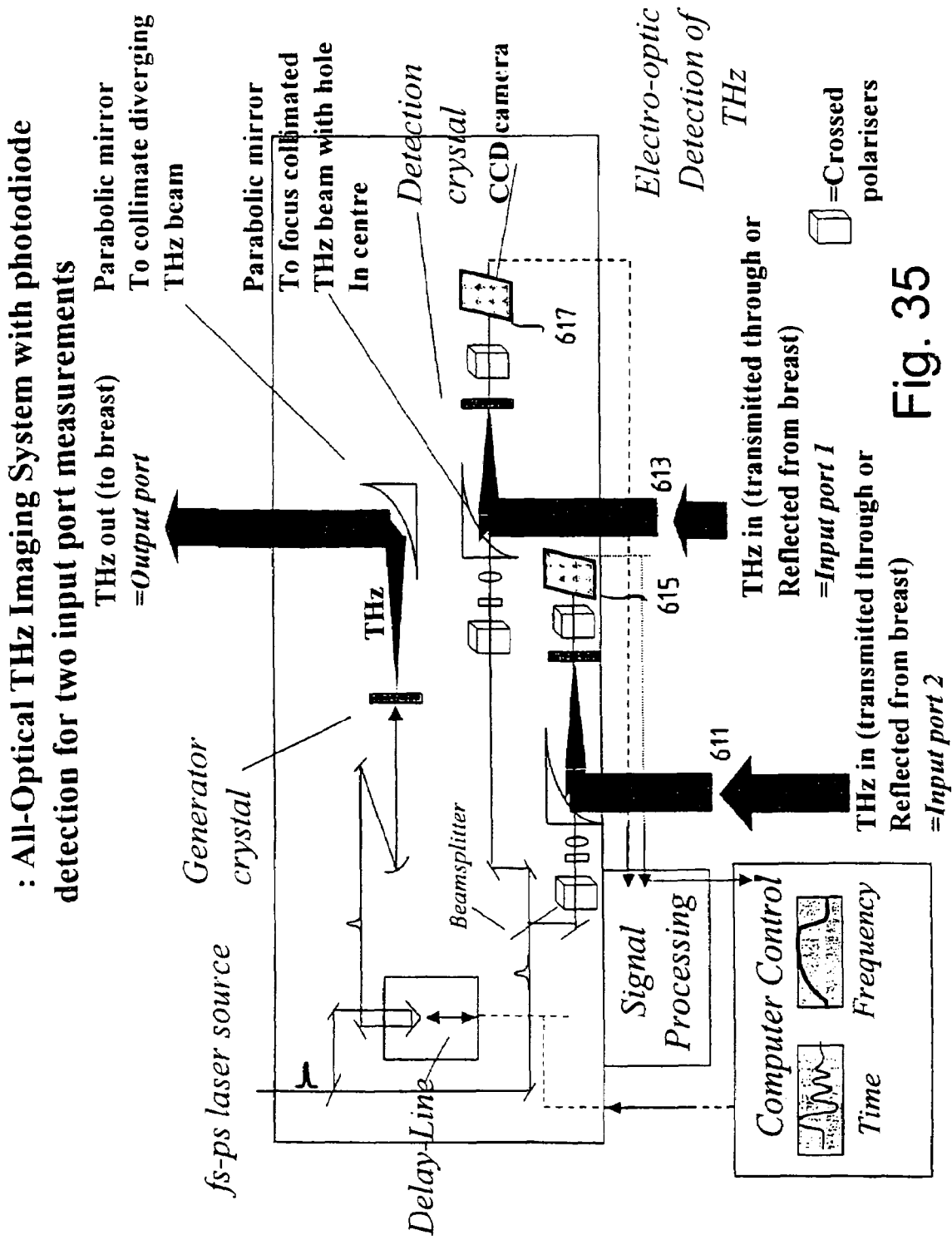
Figure 36:
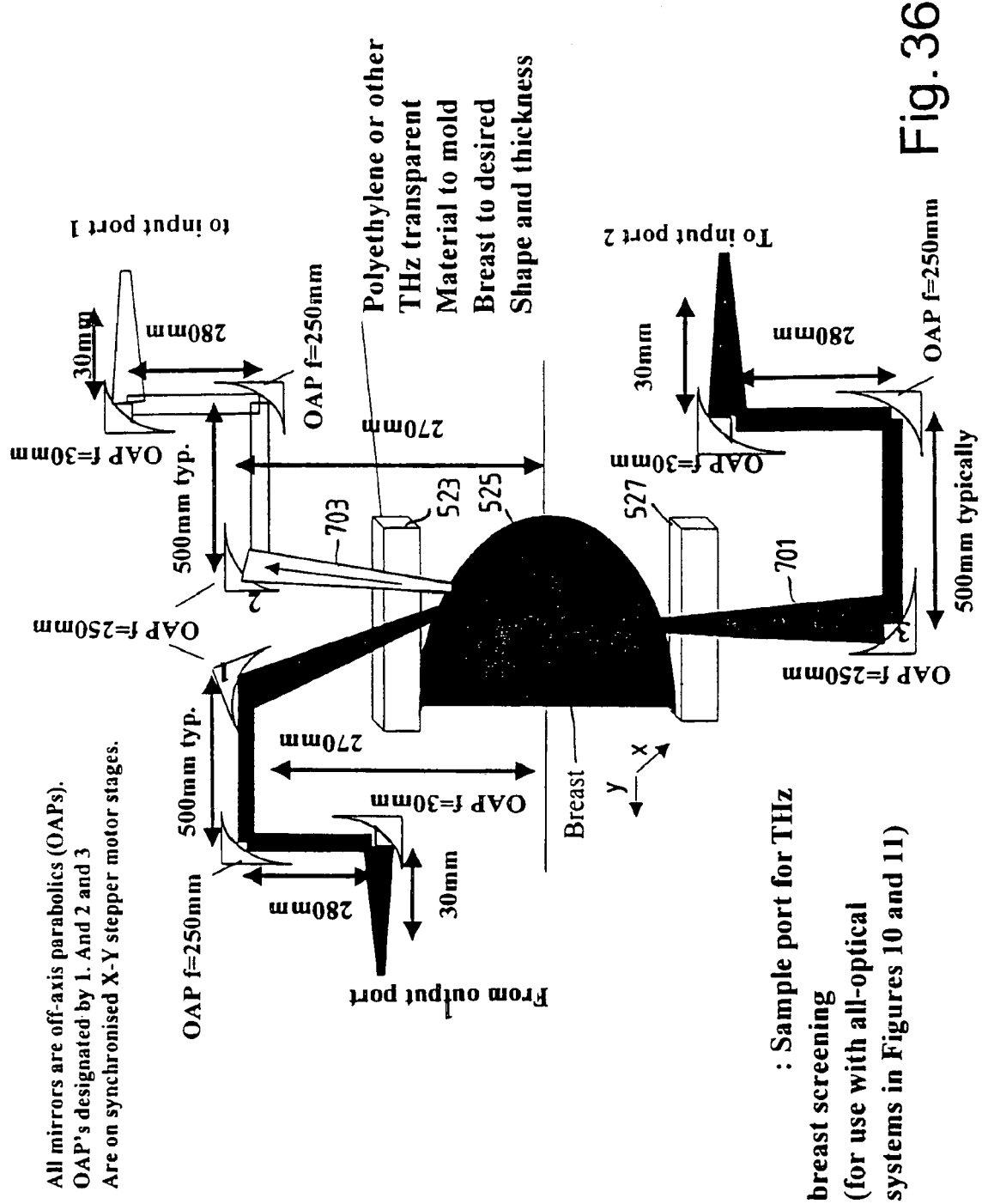
Figure 37:
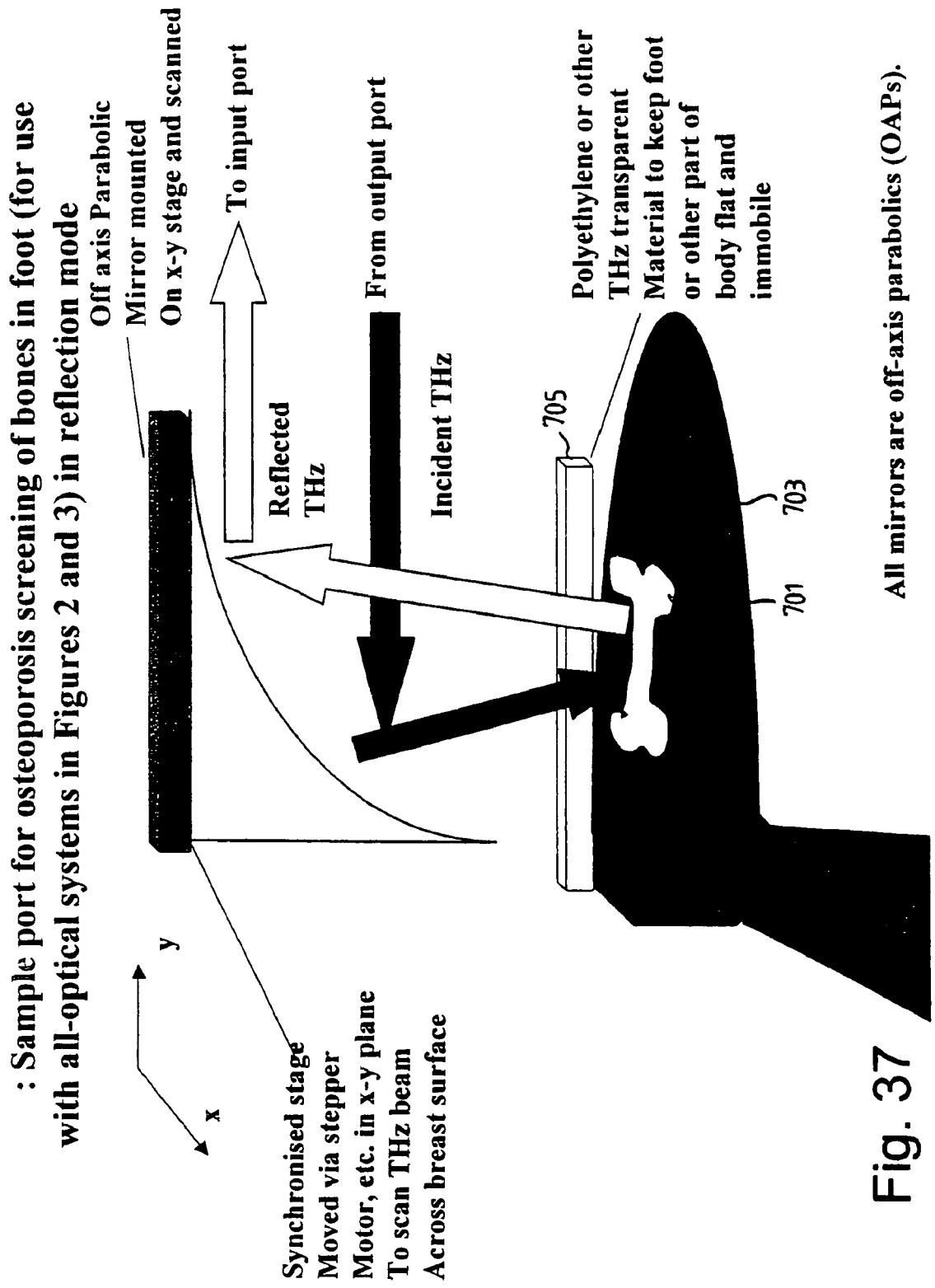
Figure 39:
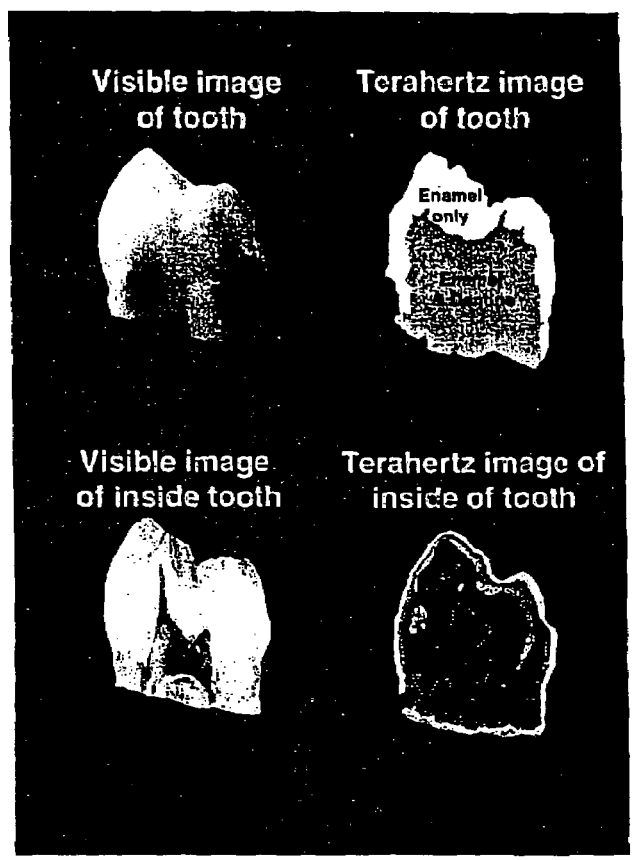
Figure 40:
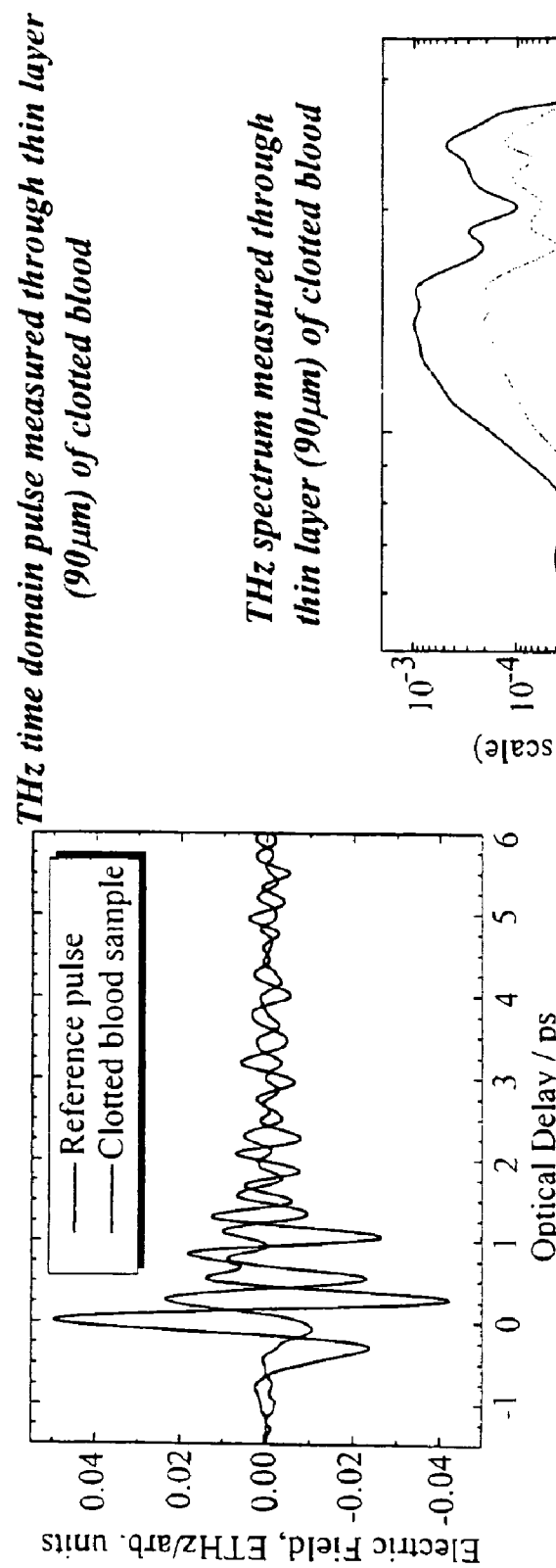
Figure 41:
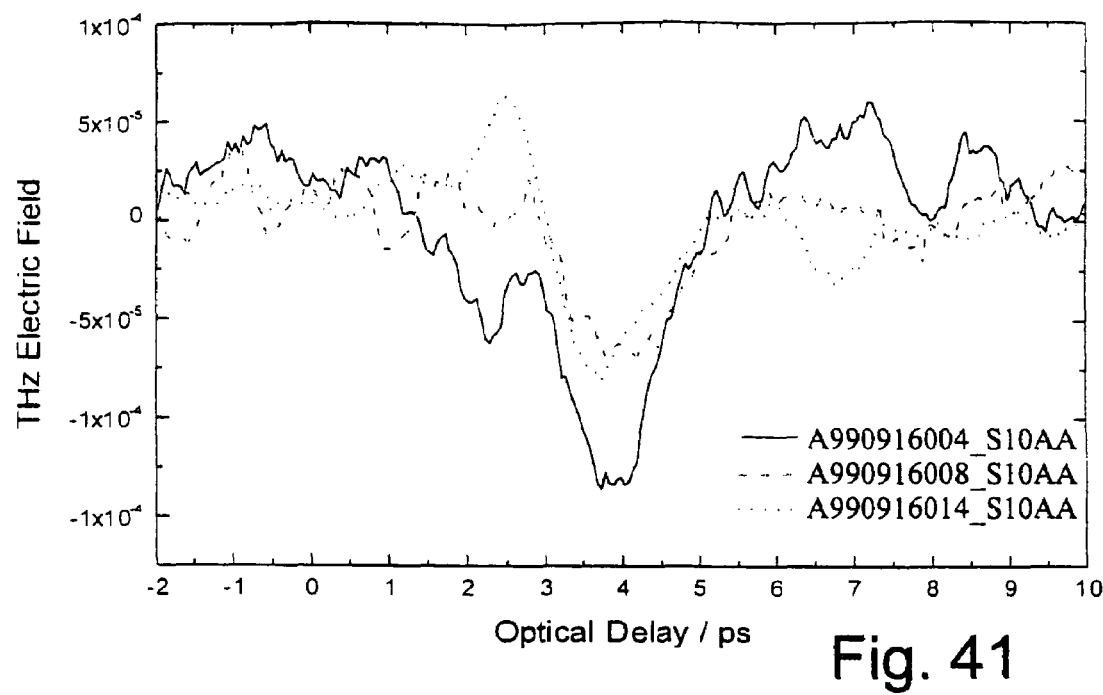
Figure 42:
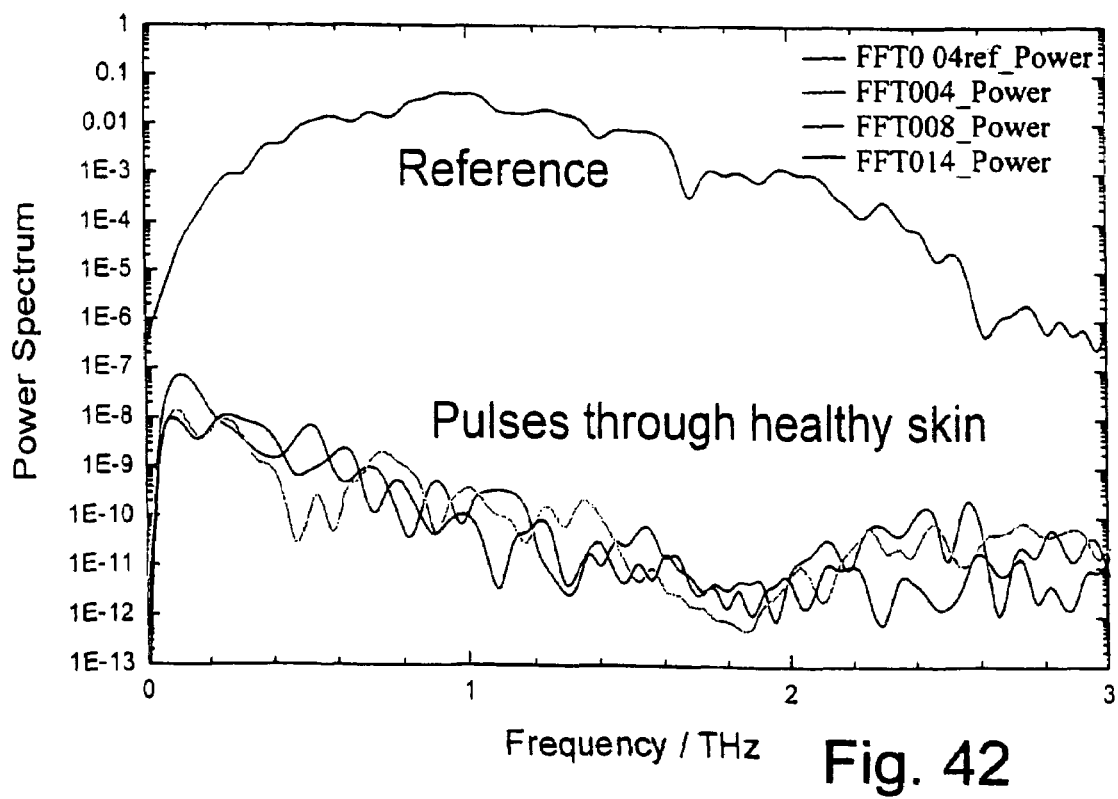
Figure 43:
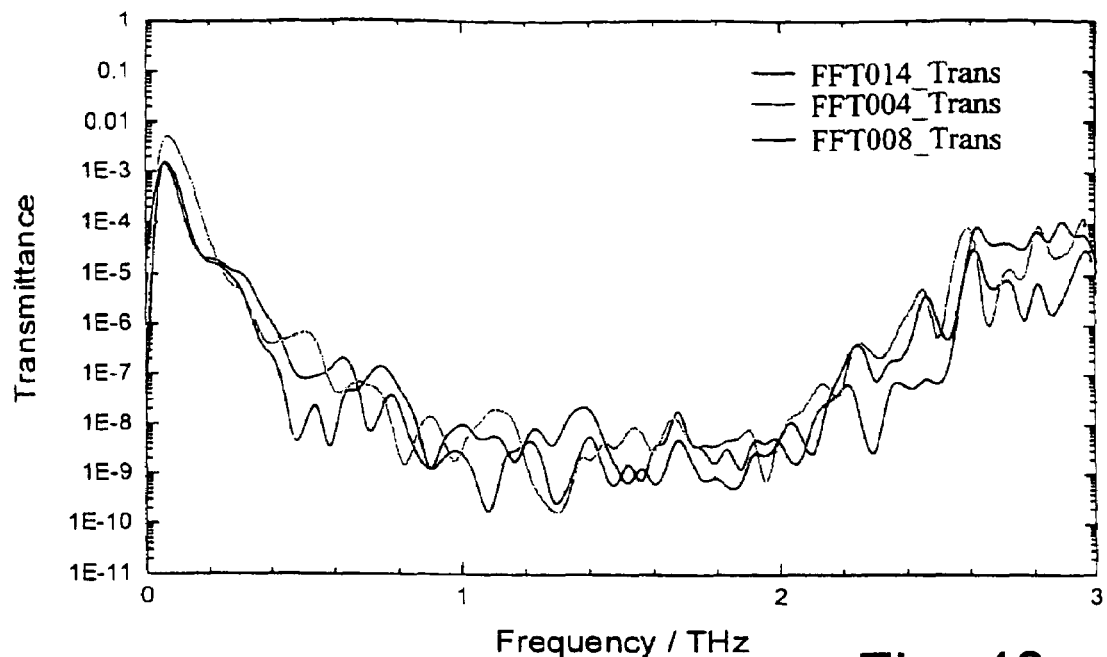
Figure 44:
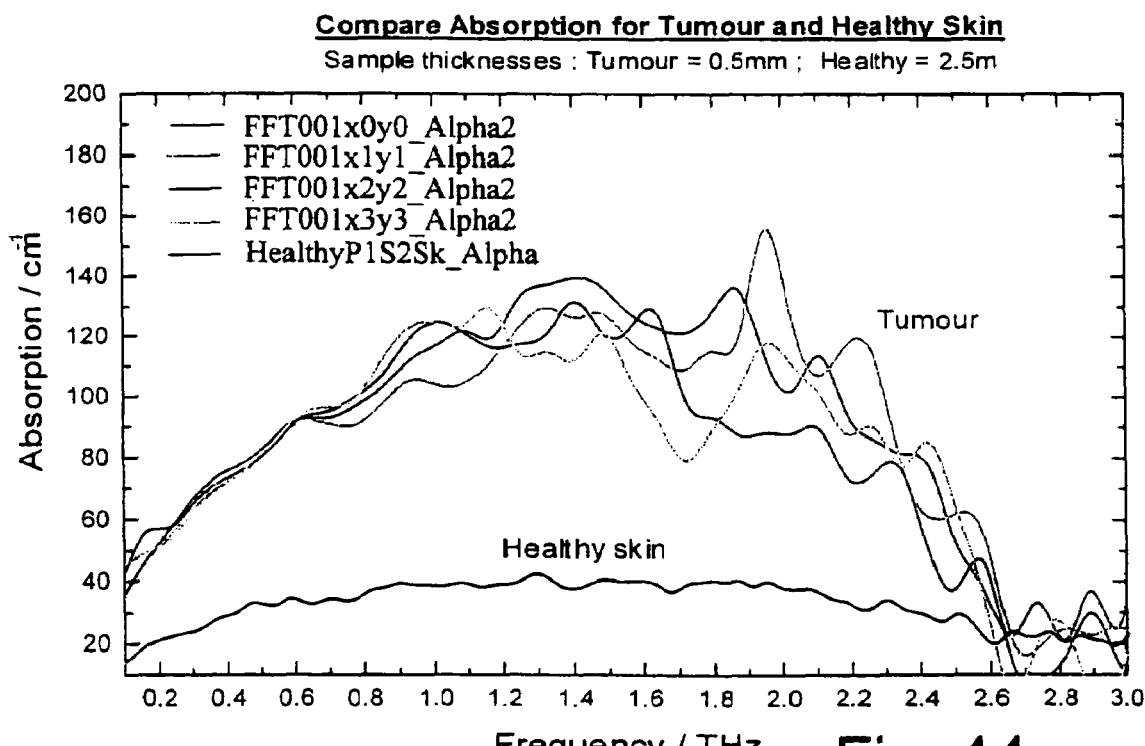
Figure 46:
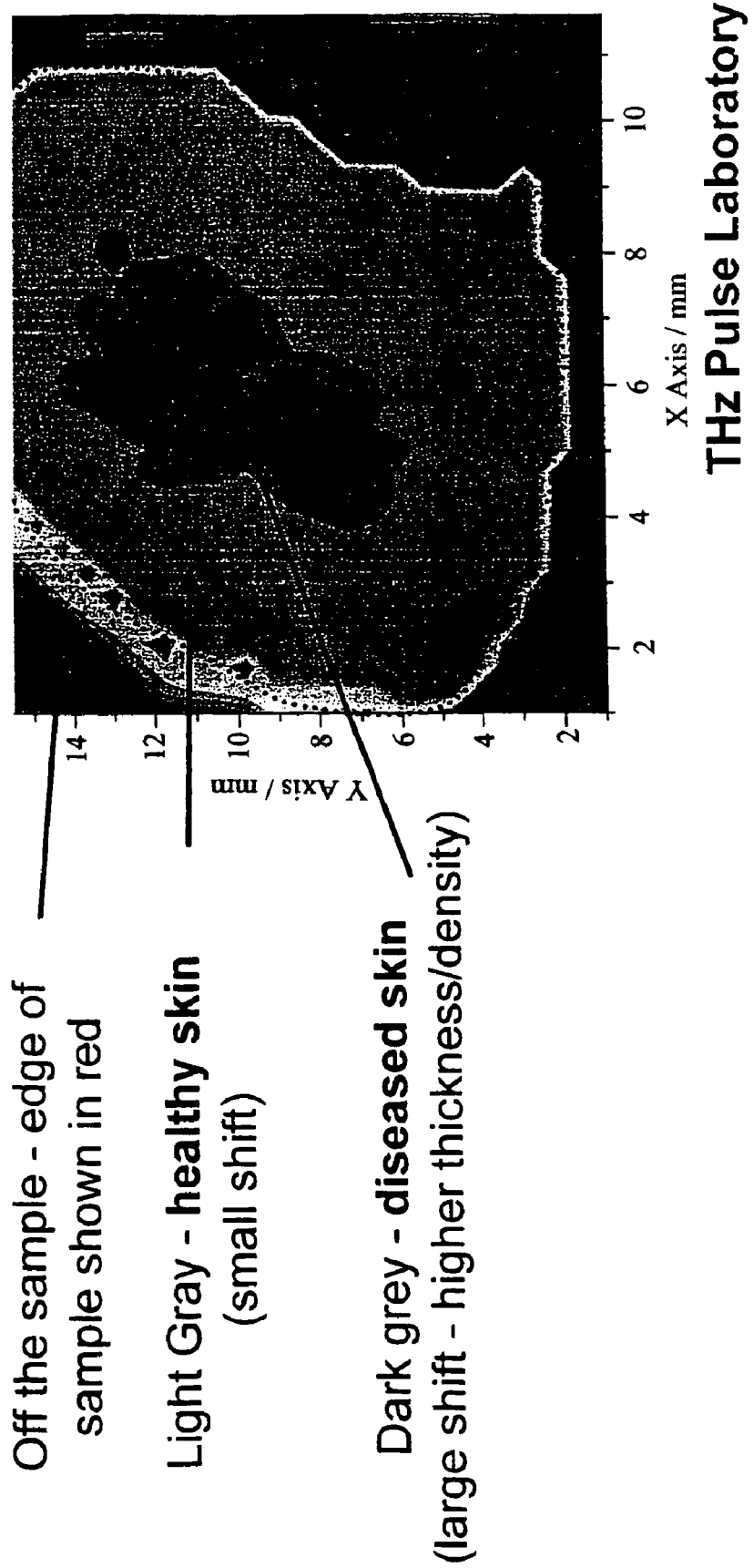
Figure 47:
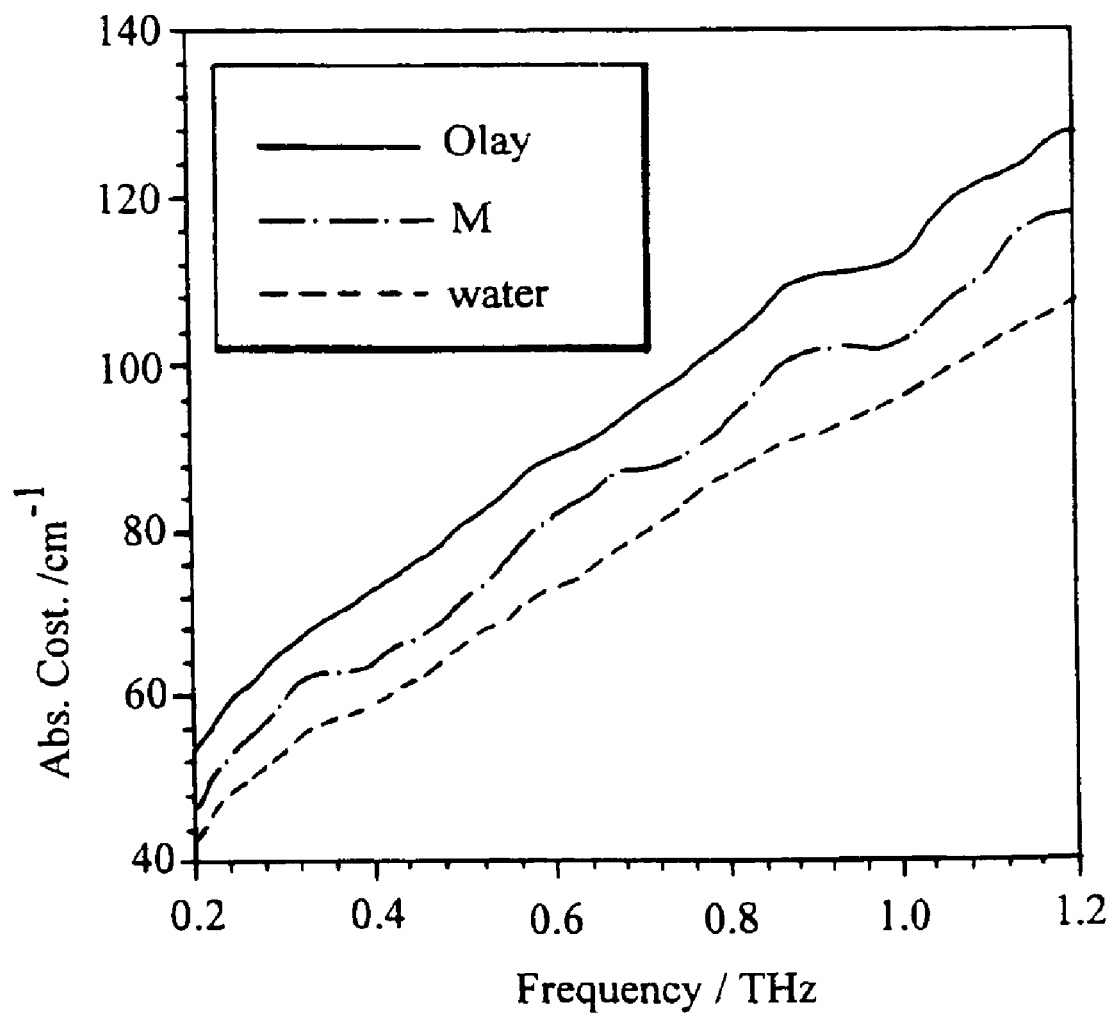
Figure 48:
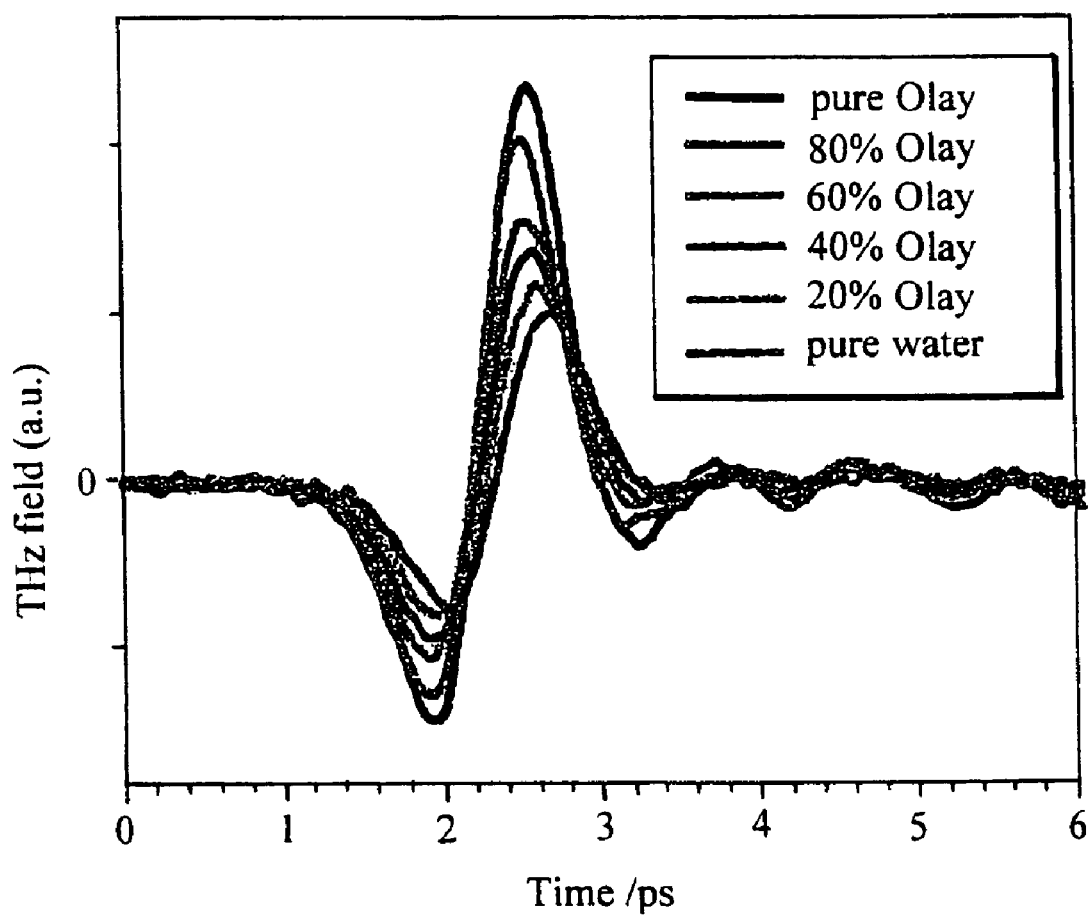
Figure 49:
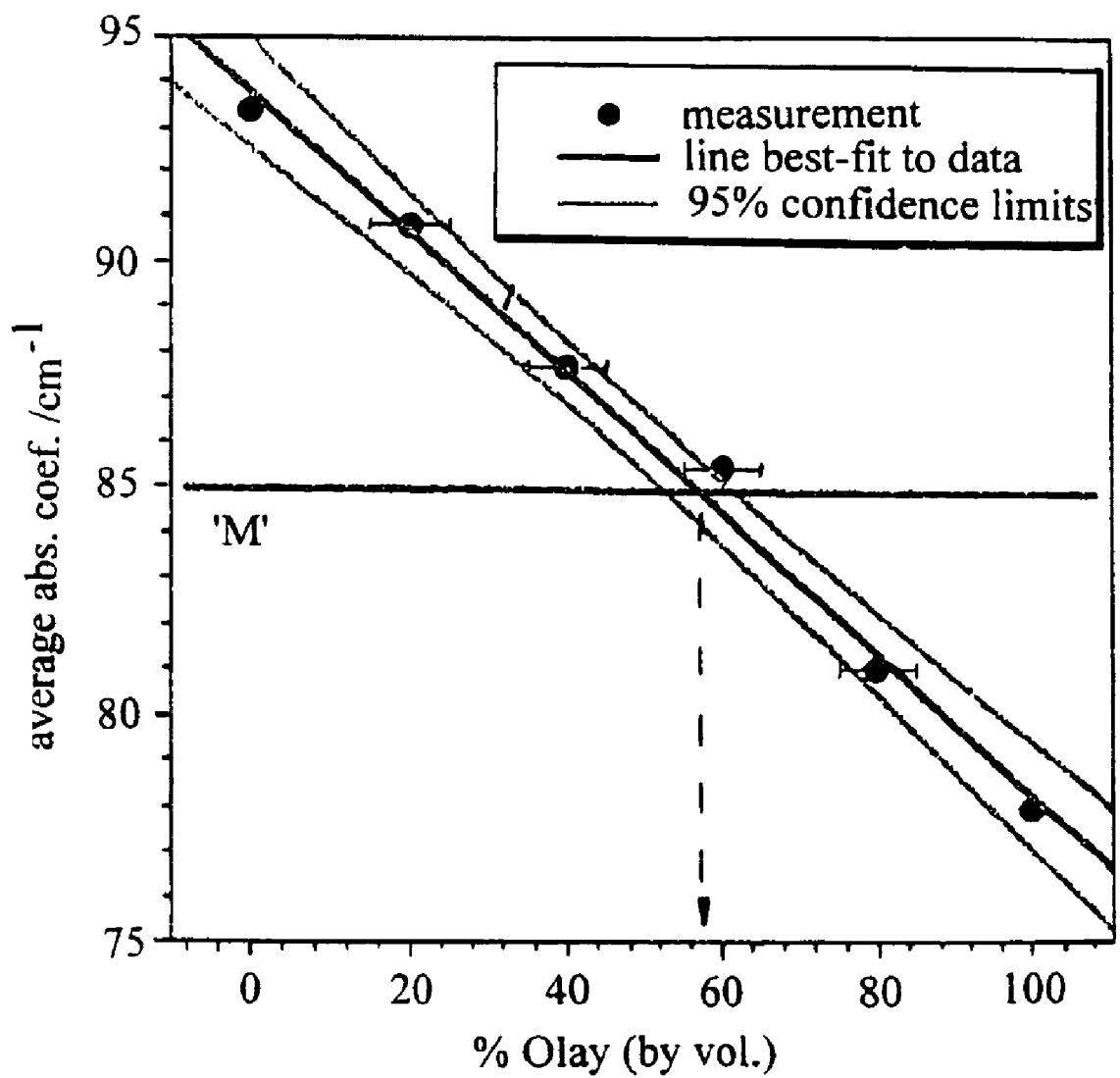

FIG. 26 shows a THz imaging system configured for detecting breast cancer;

FIG. 27 shows a variation on the system of FIG. 26;

FIG. 28 shows a schematic view of breast screening apparatus using the detection systems of FIG. 26 and/or FIG. 27;

FIG. 29 shows in detail the sample receiving area of the breast screening apparatus of FIG. 28;

FIG. 30 shows an alternative configuration of the optics of the breast screening apparatus;

FIG. 31 shows yet another configuration of the optics of the breast screening apparatus;

FIG. 32 shows a variation on the sample receiving area of the breast screening apparatus;

FIG. 33 shows a further variation on the sample receiving area and optics of the breast screening apparatus;

FIG. 34 shows a further variation on the optics of the breast screening apparatus;

FIG. 35 shows yet a further variation on the optics of the breast screening apparatus;

FIG. 36 shows a further variation on the optics and sample receiving area of the breast screening apparatus;

FIG. 37 shows apparatus for studying bone;

FIG. 38 shows visible and THz images of chicken bone;

FIG. 39 shows THz and visible images of teeth;

FIG. 40 shows THz images of clotted blood;

FIG. 41 shows a THz image in the time domain of healthy skin tissue;

FIG. 42 shows frequency domain data of a sample of healthy skin;

FIG. 43 shows a plot of the transmittance in the frequency domain taken from a sample of healthy skin;

FIG. 44 is a plot of absorption against THz frequency for a tumourous region of skin and healthy skin;

FIG. 45a shows a visible image of a skin tumour and FIG. 45b shows the corresponding image taken using THz radiation;

FIG. 46 shows a further THz image of a skin tumour;

FIG. 47 shows a plot of absorption coefficient against frequency for two types of moisturisers and water;

FIG. 48 shows a plot of the amplitude of a THz pulse in the time domain to illustrate the effect of water on the results; and FIG. 49 shows a plot of the absorption coefficient against percentage of moisturiser by volume in water.

Figure 1:
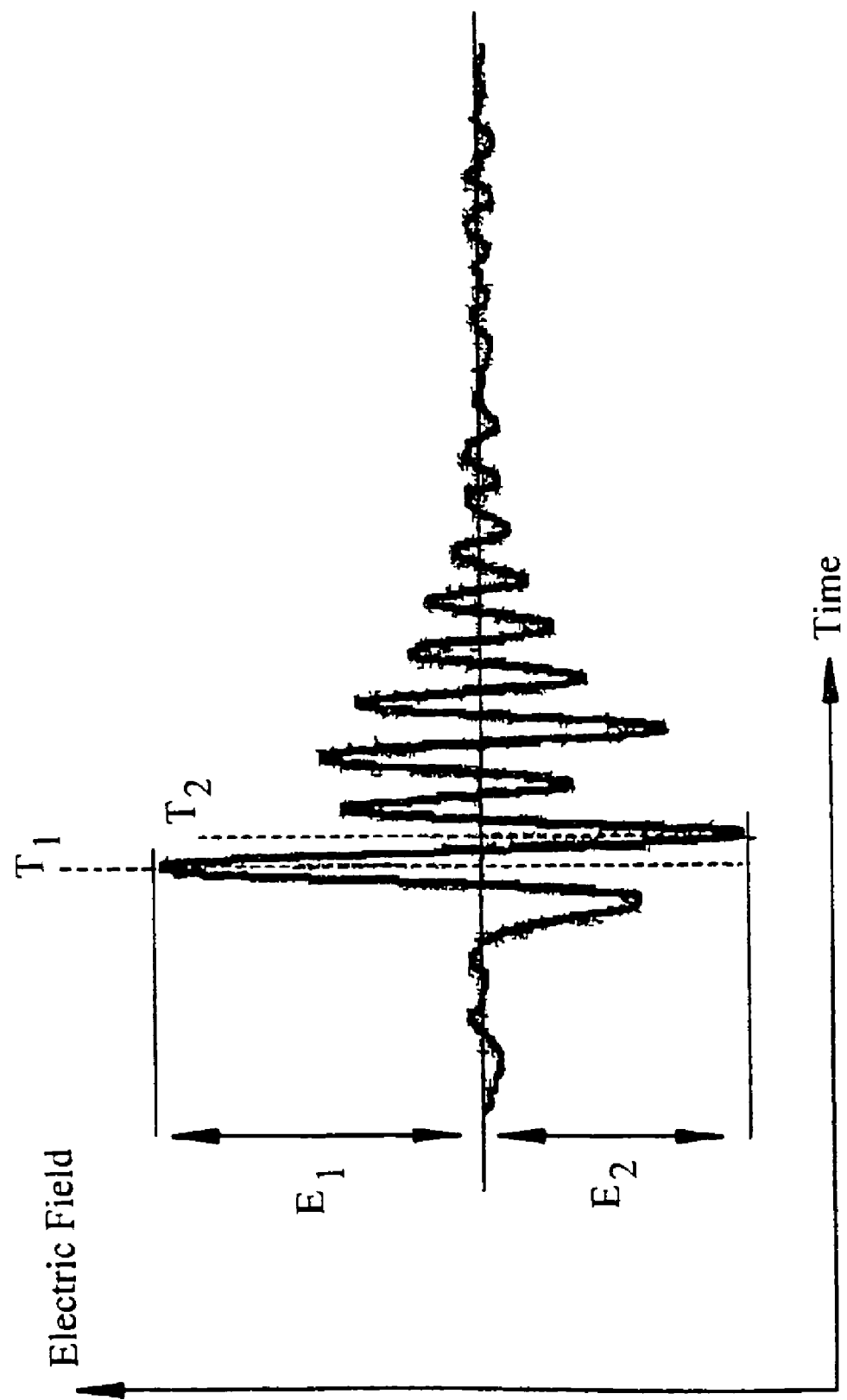
FIG. 1 shows a typical THz time domain data obtained from imaging a sample.

The sample is imaged by irradiating with pulsed electromagnetic radiation in 50 GHz to 84 THz. The THz radiation is either passed through the sample or reflected from the sample. FIG. 1 shows a typical trace of detected electric field over time detected from the sample for a single pixel. If there is a variation in the sample composition from pixel to pixel, then this will show up in the THz trace for each pixel.

As can be seen from FIG. 1, there is a vast amount of information obtained for each pixel therefore, the information needs to be processed to provide a meaningful image. There are four main parameters which can be derived from this time dependent signal. These are: the maxima of the electric field ($E_1$), the minima of the electric field ($E_2$), the temporal position of the maxima of the electric field ($T_1$) and the temporal position of the minima of the electric field ($T_2$).

To obtain a THz image, one or more of these parameters may be plotted directly. However, further contrast may be obtained by plotting the following functions:

1. The peak to peak height i.e. $E_1$ and $E_2$;
2. The difference in the temporal spacing between a position of the maxima $E_1$ and the position of the minima $E_2$ i.e. $T_1-T_2$. This parameter is particularly useful as it gives information on the frequency dependent absorption of the sample.
3. The product of the temporal peak position with one or more electric field parameters. For example:

$(T_2-T_1) \times E_1$ $(T_2-T_1) \times E_2$ $T_2-T_1 \times (E_1+E_2)$

Figure 2:
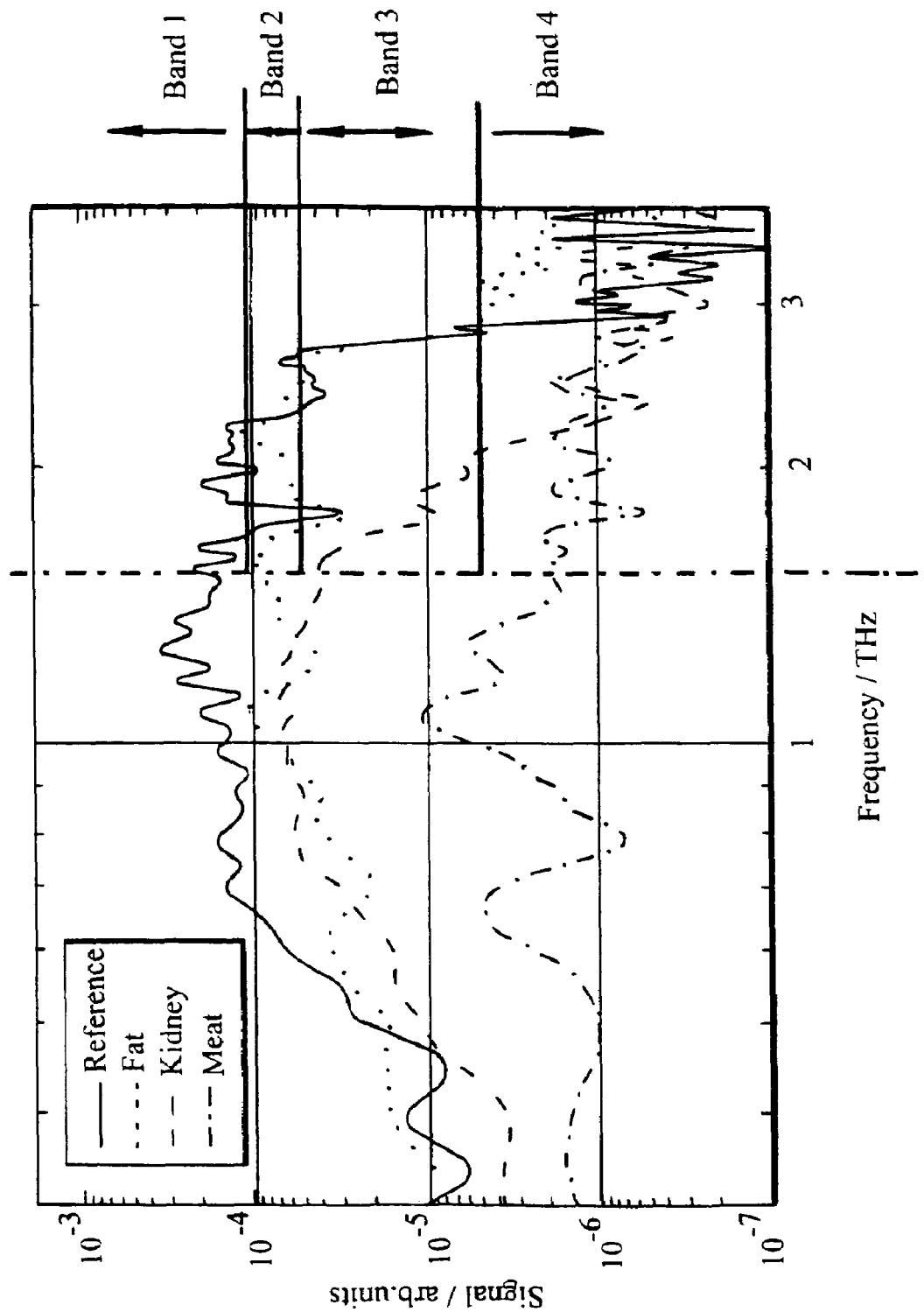
FIG. 2 shows a power spectrum of a THz trace originally measured in the time domain.

Further information may also be obtained from FIG. 1 by performing a frequency analysis. FIG. 2 shows a power spectrum for a typical trace. The power spectrum is obtained in the conventional way from Fourier transforming the temporal data (i.e. the type of data shown in FIG. 1). The magnitude of the signal is plotted logarithmically on the y-axis and the frequency is plotted on the x-axis. The data for FIG. 2 was derived from a sample which had regions of fat, kidney and meat. This sample will be described later in more detail with reference to FIG. 3. A reference signal is also shown which is the power spectrum of radiation which has not passed through the sample. By viewing the data in this form, the spacing between the data (along the y axis) for the three tissue types is seen to vary with frequency. Therefore, by choosing an appropriate frequency ($f_{select}$) an image with strong contrast may be obtained.

Also, to distinguish certain tissue types it is often advantageous to plot the image at two separate frequencies for comparison. This is particularly useful when there is little contrast between the tissue types at various frequencies. For example, taking the data of FIG. 2, it is seen that the power spectrum corresponding to kidney tissue and fat tissue has an almost identical value at 1 THz. Therefore, in an image generated at this frequency, both fat and kidney would look very similar. However, looking at the trace at around 2.5 THz, it is seen that the kidney data has a similar value to that of the meat data. Therefore, in an image taken at 2.5 THz there is very little contrast between the meat and the kidney data. However, comparing the image taken at 1 THZ with the image taken at 2.5 THz, allows the three tissue types to be equally distinguished. Two or more images at different frequencies can also be compared by a mathematical operation. For example, the data taken at 2.5 THz could be subtracted from the data taken at 1 THZ to clearly show the characteristic signal due to absorption by kidney tissue. Other mathematical operations are also possible such as multiplication, addition, and division etc.

To further enhance contrast, the data can be subdivided into a series of bands based on magnitude. In FIG. 2, four bands are shown. Each of these bands can be assigned a single numerical value and this data can then be plotted. In the data of FIG. 2, it can be seen by assigning a single value to band 2 and a single integer value to band 2 and a single integer value to band 3 where substantially enhanced contrasts between the fat tissue and the kidney tissue. This analysis can further be extended to just two amplitude bands. In one amplitude band, the amplitude is assigned a value of zero and in the second amplitude band the amplitude is assigned a value of one. This analysis allows data at two different frequencies, $f_1$ and $f_1$ to be compared using certain rules. Such a rule could be:

| Signal ($f_1$) | Signal ($f_2$) | New Value |
|---|---|---|
| 0 | 0 | 1 |
| 1 | 0 | 2 |
| 0 | 1 | 3 |
| 1 | 1 | 4 |

Also, certain Boolean algebraic expressions could be used, for example. AND. NAND. XOR, OR, NOR. For an AND comparison, the following table would be used:

| Signal ($f_1$) | Signal ($f_2$) | New Value |
|---|---|---|
| 0 | 0 | 0 |
| 1 | 0 | 0 |
| 0 | 1 | 0 |
| 1 | 1 | 1 |

Instead of the power spectrum, the frequency dependent absorption coefficient a(ω) or the frequency dependent refractive index η(ω) could be analysed in the same way as the power spectrum.

FIGS. 3a and 3b show images obtained from a pork sample.

The pork sample consists of a variety of different pork tissue types, meat, fat and kidney. Each tissue type is approximately 1 mm thick, and the area measured using THz is approximately 13×10 mm$^2$ with a 500 µm step size. The temporal scan at each pixel was 10 ps long, giving a frequency resolution of 100 GHz, and each pixel took approximately 1 minute to measure. The sample was mounted on cellulose nitrate film and a 1 mm thick polythene window, before being placed behind a THz radiation source (<110>ZnTe; 1 mm thick, 20×25 mm$^2$). Details of the apparatus used to obtain the images will be described later with reference to FIGS. 18 to 26.

At each pixel, the tissue type was identified using both the change in the magnitude and temporal position of the electric field maximum. All tissue types were found to transmit THz pulses, with the absorption increasing in the order: fat, meat, and kidney. The THz image shown in FIG. 3(b) is a panchromatic THz image since the analysis of the absorption was not frequency specific.

Comparing the visible and THz images the different tissue types have been successfully imaged and identified at THz frequencies. Due to the simplistic nature of this analysis there is an increased error along the boundary of each tissue region due to some scattering, which results in tissue types being incorrectly identified in these regions. FIG. 4 shows power spectra for each tissue type. The data was taken at 3 different pixels. Clear differences in the absorption characteristics for each tissue type are shown.

FIG. 5 shows data of the absorption coefficient for skin and kidney using the attenuation of the peak of the THz electric field. All samples were dried to minimise water absorption effects in the data. The data illustrates that the absorption coefficients for the two tissue types are different, which may be used to identify the tissues in an image; the thickness can be found from the temporal shift. Thus, the maximum tissue thickness that can be measured assuming a signal to noise ration (SNR) of $10^4$:1. For this example, these values are 3.0 mm for kidney and 7.5 mm for skin. With the addition of an amplifier to boost visible, and hence THz, powers $10^5$:1–$10^6$:1 can be achieved, which allows several cm of tissue to be probed in theory.

FIG. 6 shows data from six types of chicken tissue: bone, cartilage, skin (cooked and uncooked), meat (cooked and uncooked). All tissue types were found to transmit THz by varying amounts. The meat has the strongest absorption of all the tissue types, with the electric field results multiplied by five for clarity. The frequency domain data (NH5) shows a clear difference in the nature of the absorption for each type of tissue.

FIG. 7 shows the data from FIG. 6 plotted on a single axis for comparison.

THz can be used to image the contents of objects that are otherwise opaque at particularly visible wavelengths, much in the same way as x-rays are currently used. However, due to the non-ionising nature of THz plus the low average powers, THz is inherently safe. For example, common packaging materials such as plastics, paper and cardboard have been found to be transparent at THz frequencies. FIG. 8 shows a visible image of a spider mounted over a hole in a metal plate. The spider is placed in a plastic box for imaging as shown in FIG. 9a. At visible wavelengths it was not possible to observe the contents of the plastic box with the lid closed, FIG. 9b.

The spider and the box were imaged over a 10×10 mm region with a 200 µm step size. Analysing the image using the change in peak of the THz electric field, a THz image was formed of the contents of the box, FIG. 10. The light areas correspond to regions of highest THz transmission. The spider is clearly resolved inside the box, with fine detail, such as a break in one of legs (top right corner) resolvable. Closer inspection of the image shown in FIG. 10 also revealed some weak internal structure inside the spider.

Of considerable interest to medical applications would be the ability to measure the properties of blood using a non-invasive method on a human subject. i.e. a "contactless" in vivo method of assessing the constituents of the subject's blood. Thus, a technique that combines imaging and spectroscopic capabilities to locate and identify, respectively, different tissue types and their constituents would be of enormous medical and commercial value. Also, for imaging purposes blood is (partially) transmitting at THz frequencies. A sample of dried blood (black pudding) was taken and a thin layer spread on a piece of cellulose nitrate film. The transmission was measured at a single point on the sample, FIG. 11a, with the peak electric field decreasing by 55%. In the frequency domain, FIG. 11b, the absorption is found to be strongest between 1.00 THz and 1.90 THz, with a strong absorption around 0.66 THz.

One of the most important materials that must be considered for biological applications of THz is liquid water. Water is known to have a number of strong absorption bands in the infrared and far-infrared/THz regions due to the polar nature of the molecule, and ultimately it may be absorption due to liquid water in biological samples that limits the applications of THz technology. To quantify the strength of water absorption a thin (90 µm) layer of liquid water was measured. This layer was formed on the surface of a piece of cellulose nitrate film. The time-domain results for the sample and a reference (dry cellulose nitrate) are shown in FIG. 12a, and the frequency domain results in FIG. 12b. From the time-domain results alone the absorption is clearly stronger than in the blood sample. Considering the frequency domain results, the absorption is found to increase with increasing frequency: at frequencies above 2.5 THz the repeatability of the spectra is less reliable and therefore only the frequency range 0.6 THz to 2.5 THz should be examined. It is therefore important for biological applications that the frequency range of THz spectroscopy is extended to higher and lower frequencies where absorption windows are present. It should be noted, however that the ability of THz to probe the skin, blood, and water thicknesses noted above suggests that it is possible to use the present invention.

In FIGS. 14a to c, a commercially available, discrete transistor was taken which has the active elements encapsulated in a black casing that is opaque at visible wavelengths, FIG. 13a. Fortunately, because the black casing is partially transparent to THz, the internal structure of the device can be imaged. The THz image in FIG. 13b was constructed using 150 µm steps over a 5×6 mm$^2$ region centred on the transistor. Where there is only plastic, THz pulses are transmitted, but where there are metal tracks of the three leads, no THz is transmitted. To confirm the accuracy of the THz image, an identical transistor was cut open and the same lead arrangement was found, as recorded in the visible photograph of FIG. 13c. Additional information on the depth of the leads below the outer surface could be obtained using reflection-based imaging. Scanning the THz beam across the front of the sample, strong reflections were recorded in regions with the metal tracks, with the temporal delay of the pulses giving the distance of the tracks below the surface.

A simple image of the distribution of the doping in a semiconductor can be formed using the change in the peak of a transmitted THz pulse, due to the approximately linear increase of THz free-carrier absorption with carrier density. FIG. 14b shows a visible image of a sample consisting of two strips of undoped GaAs and two strips of n-type (n~1×10$^{18}$ cm$^{-3}$) with the strips arranged alternately side by side. Each strip was 10×1×0.5 mm. An area of approximately 8×8 mm$^2$ was imaged using THz, with a 200 µm step size. While at visible wavelengths there was no means of identifying the GaAs, the THz image clearly shows a difference in the absorption, FIG. 14a. Here the peak of the THz field is plotted for each pixel. The highest transmission (at the bottom of the image) is where there was no GaAs present. Moving across the GaAs strips there is variations in the absorption due to the different dopings, with absorption strongest in the n-type strips. Strip #3 also shows a step in the absorption at the boundary of the etch through the n-type doping.

FIGS. 15a and 15b show frequency dependent (monochromatic) images derived from the THz data of the semiconductor sample. Instead of plotting the peak of the field, power spectrum for each pixel is found using a fast Fourier transform and the power at a given frequency selected. FIGS. 15a and 15b show the images for f=2.38 Thz and f=890 Ghz respectively. At 2.75 THz the image is similar to FIG. 14a, with the difference in the absorption between the two type of GaAs clearly resolvable. However, for the 890 GHz image there is no difference in the transmission for the undoped and areas with no sample, with both appearing as the same shade of grey indicating that no absorption in the GaAs at this frequency. Thus showing that sequentially viewing the images at a plurality of different frequencies can be used to determine information about the sample.

FIG. 16 shows a schematic apparatus which can be used to look at a THz image for a plurality of different frequencies. The apparatus, in its most basic form involves a module 1001 having a screen 1003 and a knob 1005. The knob 1005 is a frequency selector and controls the frequency of the image to be shown on screen 1003.

The detection system will detect a plurality of different frequencies. The image which is to be displayed will be dependent on the setting of frequency selector 1005. In this simplified arrangement, frequency selector 1005 has three settings, A, B, and C. The sample has three concentric rings. The composition of each of the rings is different so that each ring will strongly absorb (become shaded) at a particular frequency. At frequency A, the inner ring is strongly absorbing. However, the two outer rings do not absorb. Therefore, looking at the sample at just frequency A provides virtually no information about the outer two rings. Switching to frequency B using frequency selector knob 1005 changes the image so that the middle ring is now strongly absorbing. However, the inner ring and the outermost ring do not strongly absorb at this frequency. Comparing images A and B allows information about the whole structure of the sample to be determined. This is far more useful than just looking at image A or just image B. It is also less complicated than looking at a fill panchromatic image of the structure.

When the frequency selector knob 1005 is turned to C, the frequency is selected so that the outer ring strongly absorbs and the inner two rings do not. The situation is similar to Figure A in that no real information can be established about differences between the two inner rings.

FIG. 17 shows a basic THz imaging system. The system can be simplified into three main sections, a generator 31, an imaging section 33 and a detection section 35. THz radiation is generated in the generating section 31 by using a THz emitter which is supplied by a visible pulsed laser 37.

A THz beam 39 is emitted from generation section 31 and is directed onto sample 41 of the imaging section 33. The THz beam 39 is then directed via further optics 45 into the detection section 35. The system of FIG. 17 is an example of a near field imaging system, where the sample to be imaged is placed immediately behind the THz source.

The detection section reads the information carried in the detected THz signal via a visible light signal and AC Pockels effect. The visible light is ideally obtained from laser 37 via beam splitter 47. A time delay is added to the THz pulse via time delay line 34. The system (e.g. the control of the sample 41 movement, the time delay 34 and the detected signal processing) is controlled by computer 36.

Details of the AC pockels effect will be described with reference to FIG. 19.

FIG. 18 shows another imaging system. Here, for simplicity, details of the detection part of the system will be omitted. These will be described with reference to FIG. 19.

The THz generation section is indicated by the components within box 51. The imaging system requires both a visible light pulse and a THz pulse to be emitted from the generation section 51. Therefore, the output coupler 23 should not 100% reflective to visible radiation to allow some visible radiation to be emitted from the THz generation section 51.

The emitted THz beam 53 and visible 55 from the generation system are incident on beam splitter 57. This beam splitter 57 allows transmission of the THz beam 53 but reflects the visible light beam 55 onto mirror 59 which reflects the beam 55 into optical delay line 61. The delayed beam 55 is then inputted into the THz detection unit 63.

The THz beam 53 is directed into the imaging section 52 and onto sample 65 via THz imaging optics 67. The sample 65 is located on a motorised X-Y translation stage (not shown) so that the whole sample 65 can be imaged. (The x-y plane is orthogonal to the beam axis). The THz radiation 69 carrying the imaging information from the sample is reflected into the THz detection system 63 via THz imaging optics 71.

The presence of visible radiation 55 as well as THz radiation 69 allows for imaging and electro-optic detection to be performed inside a single nitrogen-purged unit.

The sample 65 is mounted on a X-Y motorised translation stage (not shown) which is controlled by a PC computer (not shown). Each section (pixel) of the object may then be imaged. To improve the spatial resolution of the technique, off-axis parabolic mirrors, condenser cones, and lenses may be used to focus the beam to a diffraction limit spot. By mounting the sample in the near field of a condenser cone, the diffraction limit may be overcome and spatial resolution of about 50 µm may be achieved. The imaging system can function with or without such objects depending on the nature of the object to be imaged and the nature of the detection circuit.

FIG. 19 shows the detection system in detail. The THz beam 69 carrying the imaging information and a visible light beam 55 are inputted into the THz detection system. The visible light beam 55 acts as a reference beam which is incident on the detection crystal 73. The reference beam 55 is linearly polarised and the polarisation is orientated such that it has components along both the ordinary and extraordinary axis of the detection crystal 73. Each of the axes has distinct refractive indices $n_o$ and $n_e$ along the ordinary and extraordinary axis of the crystal 73 respectively. In the absence of a second (THz) radiation beam 69, the linearly polarised reference beam 55 passes through the detection crystal 73 with negligible change in its polarisation.

The applicant wishes to clarify that the angle Θ through which the polarisation is rotated by is negligible. However, the linearly polarised beam can become slightly elliptical. This effect is compensated for by a variable retardation waveplate, e.g. a quarter waveplate 81.

The emitted beam 77 is converted into a circularly polarised beam 83 using quarter wave plate 81. This is then split into two linearly polarised beams by a Wollaston Prism 79 (or equivalent device for separating orthogonal polarisation components) which directs the two orthogonal components of the polarised beam onto a balanced photodiode 85. The balanced photodiode signal is adjusted using wave plate 81 such that the difference in outputs between the two diodes is zero.

However, if the detector 73 also detects a secondary beam 69 (in this case a beam with a frequency in the THz range) as well as a reference beam, the angle Θ through which the polarisation is rotated by is not negligible. This is because the THz electric field modifies the refractive index of the visible (fundamental) radiation along one of the axes $n_e$, $n_o$. This results in the visible field after the detector 73 being elliptical and hence the polarisation components separated by the prism 79 are not equal. The difference in the voltage between the output diodes gives a detection voltage.

The reference beam 55 and the THz beam 69 should stay in phase as they pass through the crystal 73. Otherwise the polarisation rotation Θ is obscured. Therefore, the detection crystal 73 has phase matching means to produce a clear signal.

All of the items shown in FIG. 20 sit on an optical bread board of dimensions 36 inches by 36 inches. The only external units required are a power supply for the diode laser and a cooling unit for the generation section 51.

The imaging section 91 has a motorised stage which is movable in the x-y plane, i.e. along two orthogonal axis which are perpendicular to the incident beam of THz radiation.

The imaging section 91 has two mirrors M11 and M12. Mirror M12 directs the THz beam 53 onto the sample 65. Mirror M11 is positioned to reflect the THz radiation transmitted through sample 65 onto the detection crystal 73. Mirrors M11 and M12 are off axis parabolic (OAP) mirrors. Such mirrors are configured so that the phase difference between the incident and reflected beams is the same at all points on the mirror. The parameters resulting in an off axis parabolic surface are characterised by the focal length of the mirror.

An optical delay section 93 is also shown. The visible light beam emitted from the generating section is reflected by beamsplitter 57 into delay section 93. The delay section 93 has a corner cube mirror M9 which is moveable along the beam axis. The beam is directed onto corner cube mirror M9 via mirror M8. The beam is reflected off corner cube mirror M9 onto mirror M10. Corner cube mirror M9 is oscillated back and forth along the beam direction with an oscillation frequency of several 10s of Hz. This increases or decreases the path length of the visible beam 55 as required. A Clark ODL-150 system may be used to drive the mirror, this is capable of delays of 150 ps. The emitted beam is then combined with the emitted THz beam at mirror M11.

Alternatively the THz and visible beams may be combined colinearly using a beam splitter, for example, a pellicle beam splitter. Such a device would be placed before or after M11 and would eliminate the requirement for a bole in M11.

FIG. 21 shows a variation on the imaging section 91 of FIG. 20. The extended path length over which the THz beam 53 travels is purged with nitrogen to remove water vapour and hence improve the quality of the image.

Due to diffraction effects associated with the large wavelengths in the THz range, the cross-sectional size of the THz beam 53 and imaging applications is not sufficiently large that it may be treated as plain parallel. If diffraction effects are such that the radiation is paraxial so that it can be represented by a scalar field distribution. Gaussian beam mode optics and optical techniques can be used. The simplest case for system design is to assume that the fundamental mode dominates the beam profile. The use of Gaussian mode optics and design applied to conventional THz radiation and systems (generated in the Fourier transform machines, far-infrared lasers or Gunn diodes) is applicable and important to THz imaging systems.

A number of design rules or guidelines should be followed when constructing a THz imaging system to obtain a good quality image. For transmission optics such as lenses, geometric losses are kept to a minimum by ensuring that the ratio of the lens thickness to focal length and diameter to focal length is less than 0.2. If this is satisfied, then losses in the lenses will be primarily due to absorption and reflection. In this case, choice of materials is important.

A requirement which arises in pulsed systems is the need for the material to be non-dispersive so that pulse broadening does not occur. Given these requirements, high density polyethylene (DHPE), polytetrafluorethylene (PTFE), high resistivity silicon (Si), and TPX are some of the best materials and can also be machined in a lathe: any material combining low absorption and low dispersion at THz frequencies is a good candidate for fabrication of transmission optics, provided its shape can be suitably fabricated for a lens. Reflection losses in lenses tend to be highly frequency dependent at THz frequencies. Therefore care must be taken in lens design to ensure that all frequencies across the pulse bandwidth undergo the same reflection (and absorption) losses.

Ideally, reflective optics (mirrors) are used wherever possible instead of transmission optics (lenses) in order to minimise a number of losses associated with transmission optics, which include (i) frequency-dependent reflection losses and amplitude pattern distortion at dielectric (e.g. air-lens) interfaces, (ii) frequency-dependent absorption losses, (iii) diffraction effects and distortions to field distribution due to power falling on the lens's surface at an angle.

An additional property of importance in imaging (and not particular to Gaussian mode beam optics) is that if two mirrors are separated by the sum of their focal lengths, then the size of the beam waist (minimum beam diameter in plane normal to optical axis) on the optical axis after the reflection from the second mirror will be frequency-independent. This is true of the last mirror (focusing element) in a chain provided there are an even number of focusing elements in the chain. This provides a major advantage for THz imaging as the pulse is comprised of a wide range of frequency components and it is desired to keep the object at a fixed position on the optical axis whilst images are being recorded at various (x, y) points and at all THz frequencies in the pulse. This is particularly important THz imaging as the spectral coverage (bandwidth) of THz pulses increases into the mid-infrared and even higher frequencies.

The system in FIG. 21 will produce beams with l/e diameters (for the fundamental Gaussian mode in the beam) of 1–2 mm at the sample in the THz frequency range (e.g. at 300 GHz, diameter=2 mm). In the system of FIG. 21, six mirrors and two lenses are used as opposed to the two mirrors of FIG. 20. The direction of the beam in FIG. 21 is reversed to that in FIG. 20. In the imaging section, the beam is first reflected off first OAP mirror 101 onto second OAP mirror 103 and then onto third OAP mirror 105. Second 103 and third OAP mirrors each have a focal length of 250 nm. They are separated by 500 nm.

The beam is reflected from the third OAP mirror 105 onto plano-convex lens 107 which has a focal length of 10 mm and a diameter of 10 mm. Third OAP mirror 105 is separated from piano convex lens 107 by 260 nm (i.e. the sum of their focal lengths). The lens 107 is made from polyethylene or high resistivity Si. The lens 107 is placed 10 mm from the motorised stage (not shown) on which sample 109 is mounted. The beam has traversed through an even number of focusing optics and mirrors (101, 103, 105 and 107) which are all spaced apart by the sum of their focal lengths. Hence, the waist of the beam at the sample is independent of the frequency. Here, the beam diameter is chosen to be 2 mm, independent of frequency in the frequency range of about 300 GHz (0.30 THz).

Once the beam has passed through sample 65, the transmitted THz radiation falls onto second plano convex lens 111. Plano convex lenses 107 and 111 are identical in optical characteristics. Lens 111 focuses the THz radiation onto the fourth OAP mirror 113. Fourth OAP mirror 113 has a focal length of 250 mm and reflects the THz beam onto fifth OAP mirror 115. Fifth OAP mirror 115 also has a focal length of 250 mm and lies 500 nm away from the fourth OAP mirror 113 (i.e. the sum of the focal length of the fourth and fifth OAP mirrors).

The beam is reflected from the fifth OAP mirror 115 to the sixth OAP mirror 117. Sixth OAP mirror has a focal length of 30 mm and is located 280 mm away from the fifth OAP mirror (i.e. the sum of the focal length of the fifth and sixth OAP mirrors).

The sixth OAP mirror 117 is provided with a hole 119. The visible light beam 55 is passed through this hole to combine it with the THz beam 69 for detection.

Further improvements in spatial resolution may be achieved by inserting condenser cones (made of brass or copper, highly polished on insides, with electro-plating and/or gold/silver evaporated coating) adjacent to the sample to be imaged as shown in FIG. 22. In FIG. 22, condenser cones 121 and 123 are located on either side of the sample 125 between the sample 125 and piano convex lenses 127 and 129 respectively. The piano convex lenses are the same as those described with reference to FIG. 21. They have a focal length of 10 mm and are placed 10 mm away from condenser cones 121 and 123. The cones have a typical entrance aperture of 2 mm and an exit aperture of between 50 to 100 $\mu$m.

The sample 125, is typically placed within a few wavelengths of the exit aperture of condenser cone 121 e.g. about 100 $\mu$m such that near field imaging techniques may be used to realise THz spot sizes at the sample which are less than the diffraction-limited spot size.

Another advantage of this design is that the beam waist size is frequency independent at the aperture entrance., so that all frequencies in the pulse should fit into the condenser cone.

The plano-convex lenses 127, 129 condenser cones 123, 121 and sample 125 are placed between OAP mirrors 131, 133. The mirrors have a focal length of 250 mm. THz beam 53 is reflected from OAP mirror 131 onto piano convex lens 127 which focuses beam 153 onto condenser cone 121. The beam 53 enters through the widest aperture of the condenser cone and exits through the narrowest aperture onto sample 125. Once beam 53 has passed through sample 125 it enters condenser cone 123 and exits the condenser cone 123 through its narrowest aperture onto piano convex lens 129. The beam is then reflected off OAP mirror 133 onto the detection crystal 73. The OAP mirror 133 has a hole 135. Visible light from the generator is combined with the THz beam 69 at mirror 133. It should be noted also that the optical configuration in FIG. 7 can also be used with a multiplicity of other mirrors, such as the arrangement in FIG. 21. It should be noted, however, that a variety of different focal lengths are possible for mirrors 133 and 131.

Also, the arrangement of condenser cones used here can easily be inserted into the system of FIG. 21 using similar guidelines to beam size and mirror placement as those already elucidated.

It should be noted that simpler coupling systems such as that in FIG. 23 are possible which utilise only two off-axis parabolic mirrors. These reduce the path length of the beam and therefore minimise losses due to any water vapour or other absorbing gases in the beam path. However, transmission optics are necessary in order to create frequency independent beam waists at the same and/or to realise higher spatial resolution.

In FIG. 23, the THz beam 53 is reflected from OAP mirror 141 onto sample 143. The focal length of OAP mirror 141 is 30 mm and sample 143 is placed 30 mm away from OAP mirror 141. Optionally, further optical components such as lenses and condenser cones as described in FIG. 22 may be added between mirror 141 and sample 143.

Once beam 53 has passed through sample 143 it is encoded with imaging information and is referred to as beam 69. Beam 69 is reflected from OAP mirror 145 onto the detection crystal. The OAP mirror is provided with a hole 147 which allows the visible beam 55 to be mixed with the THz beam 69 for detection.

FIG. 24 shows a further example of an imaging system. The details of these components will not be repeated here. In FIG. 24, the delay section of FIG. 20 is replaced with a grating pair or an optical fibre 151 which chirps the visible pulse, extending its temporal width from 50 fs to about 20 ps. The different wavelength components in the visible pulse travel through the detection crystal 73 at different times.

Thus, when a grating spectrometer 153 is used to spatially disperse the wavelengths and a CCD camera 155 is used to record the spatial diversion, each pixel in the (for example) X-direction corresponds to a different wavelength and hence a different time. The result is that a given row of pixels in the x-direction on the CCD 155 effectively map out the temporal form of the THz beam which co-propagates through the detector crystal 73 and rotates the polarisation of the visible beam at different times during the pulse by varying amounts. Thus, transmission through the object being imaged is plotted as a function of time along one direction in the CCD array. Hence, the rotation of the polarisation of the reference beam 55, is measured by crossed polarises 161, 163 which are arranged on either side of the detection crystal 73.

The imaged object may then be stepped in the y direction on the translation stage in the usual way to develop a 2D THz image. Alternatively, if the probe beam is focused down by a cylindrical lens to a line (say 400 $\mu$m in x by 10 mm in y) on the sample, the THz transmission along the y axis of the sample can be measured by the pixels along y direction of the CCD, i.e. the y-pixels of the CCD may then be used to image the object in the y-direction without resorting to the translation stage moving in y. A full image is then completed by stepping the translation stage in x. Both of these abilities (to measure time delay along the x-axis of the CCD and y image information without mechanical movement) resulting in much quicker acquisition times if sufficient THz power is available as in this intra-cavity design to affect higher signal to noise ratios. Quicker data acquisition and potentially cheaper cost for more compact systems are the result.

The primary advantage of this system is the fast data acquisition owing to the lack of moving parts such as translation stages; using this system, both a) imaging along the y-direction of the object and b) the sampling of the time domain is very fast, limited the creation of a time delay are very fast, limited only by the speed of the CCD camera and the need to average many frames from the camera to get adequate signal to noise rations (SNR) on the images. The latter is the chief mechanism which limits the application of this technique, and hence the realisation of real-time imaging. Poor SNR results in part from the fact that the balanced photodiode detection scheme outlined in FIG. 5 can no longer be used because the quarter wave plate would introduce background light onto the CCD as strong as one-half of the total probe power. Small signal detection in this scenario will be overwhelmed by photon shot noise if a CCD camera is used. To reduce the "ambient" light level on the camera, crossed polarizers are used in which the signal on the CCD falls to zero in the absence of a THz electric field. Such as detection system is optimal for a CCD, but still does not provide as high signal-to-noise as the system in FIG. 5, especially if lock-in detection is used in the latter case.

To overcome this SNR problem, regenerative amplifiers are used (not shown) to boost the optical peak power which non-linearly generates the THz pulse, resulting in a larger THz field. Such a system suffers, however, from numerous disadvantages. Regenerative amplifiers are extremely expensive (~£100K) and tend to be large and bulky. Also, a second pump laser to drive the amplifier is required. Lastly, such systems operate at low repetition rates (50 Hz–250 kHz), resulting in a relative decrease in average power. The bright intracavity sources designed here would overcome all of these disadvantages. The intracavity design could therefore be a major step forward in the realisation of a THz imaging system with sufficiently quick data acquisition at sufficiently high signal to noise ratios to realise THz images at video frame rates (~38 frames/sec), so-called "THz movies".

FIG. 25 shows a further example of the imaging system of FIG. 24. In FIG. 25, the motorised stage (of FIG. 24) is redundant. Instead, the imaging area of the CCD camera 155 is matched to the imaging area of the detection crystal 73. This area is typically several mm². The reference beam 55 is expanded by optics 170 (e.g. telescopic or analogous optics), such that the reference beam has a larger cross sectional area than the THz beam and ideally fills all the pixels in the CCD camera 155. The distribution of the rotated polarisation of the reference beam in the x-y plane (proportional to the THz power transmitted through the sample 65 in the x-y plane) is transferred to the pixels of the CCD camera, resulting in a THz image of the object appearing on a CCD or a computer screen (not shown) attached to the output of CCD camera 155. The time delay in this system is created by an optical delay line (as described with reference to FIG. 20). This is the only mechanical moving part of the system.

FIG. 26 shows an imaging system for breast cancer detection.

The conventional imaging technologies which have been applied to mammography include 1) X-ray camera, X-ray CT imaging, 2) supersonic echo imaging, and 3) MRI.

1) X-ray camera and X-ray CT imaging have the general advantage of high success in the detection of diseased or abnormal tissue or body parts. However, X-ray imaging has a disadvantage of not being capable of obtaining high contrast and high sensitivity between different soft tissue types and abnormalities in soft tissue. This is particularly important in the breast, a major component of which is fat. Thus abnormalities in the breast, in particular due to breast cancer do not have as good contrast in X-Ray mammography as is desired. X-ray camera and X-ray CT imaging also have the historic disadvantage that side-reaction due to ionization may occur in human body given sufficient exposure.

2) In Supersonic Scan, the quality of images is intensively degraded for the fatty tissues in which the velocity of sound is relatively slower (1476 m/sec) than the cases of muscle and liver (1568 m/sec and 1570 m/sec, respectively). 3) In MRI, The image is degraded by heterogeneous resonant signals due to chemical shift of fat (about 3.3 ppm from proton signal of $H_2O$). In the case of breast images, a very uniform magnetic field is required for example 1 to 2 ppm in order to measure the images by suppressing the signal attributed to fat. However, it is quite difficult to obtain such uniform magnetic field in breast region, because of different magnetizations between air and the organism, and also because of complicated internal breast structure.

In Mammography Using a Terahertz Radiation

A breast is sandwiched by two THz transparent plates (which are made of materials which are transparent to the Terahertz pulse, including high quality z-cut quartz or semiconductor materials such as high resistivity Si, GaAs, ZnSe and ZnTe or polymers such as polyethylene, polypropylene PMMA and poly acrironitoryl, TPX) and is pressed to become as thin as possible. THz radiation with a plurality of frequencies in the range from 50 GHz to 84 THz is irradiated onto the surface of the pressed breast, the breast can be irradiated from the top, underneath or from the sides.

THz radiation which penetrates through breast is sensed by a THz detector and recorded electro-optically using free space electro-optic sampling photoconductive sampling, or other techniques.

THz signals are collected in 2D to reproduce a 2D image of the pressed breast in some appropriate level of spatial resolution which will be typically less than 1 or 2 mm. The 2D data can be collected by scanning the incident THz beam across the breast.

By using one or a combination of the contrast mechanisms noted on pages 11 and 12 above, a 2D image of the breast can be constructed. In addition, other incarnations of the THz mammograph allow THz images based on THz radiation reflected or scattered from the breast surface and inside the breast to be constructed.

The utility of the THz mammography stems in part from the fact that soft tissues such as fat are relatively transparent to THz radiation compared to other tissue types. Moreover, fat has a markedly different spectrum in the THz range compared to other tissue types. As noted above, breast contains concentrated fat which prevents the conventional X-ray, Supersonic and MRI imaging technology from distinguishing breast cancer with high sensitive contrast. THz radiation can easily penetrate through the fatty part. Also, it is well known that the breast cancer frequently causes lime deposits (calcium carbonate is deposited around cancerous region), and THz absorption or reflectance is changed by lime, due to specific absorption and also due to exclusion of water from that region. Also THz frequency domain imaging can easily distinguish lime areas because of existence of the specific absorption or reflection characteristics of time.

FIG. 26 shows an imaging system for breast cancer detection. A THz imaging beam 501 is generated by irradiating a generator crystal 503 with visible light 505 in the same way as previously described. (Many different generation techniques could be used instead of using an optically non linear crystal (as previously described). For example, surface field effect or current surge techniques.) The THz radiation is then reflected off axis parabolic mirror 507 to the output port 509. The THz radiation 501 is then directed towards the sample. The radiation carrying the imaging information is then fed into the detection system via input port 511. The radiation carrying the imaging information 513 is then combined with a reference beam 515 using an off-axis parabolic mirror 517. The detection mechanism uses the AC pockels effect which is described in detail in reference to FIG. 19.

FIG. 27 shows a further variation on the system of FIG. 26. However, instead of the detection mechanism based on the AC pockels effects a CCD camera 521 is used. The CCD camera is advantageous because the THz beam does not have to be focused to a fine spot in order to extract the imaging information. Focusing of the THz beam for detection can cause imaging information to be lost under certain circumstances. Another major advantage of the CCD camera is that a larger portion of the object (e.g. breast) can be imaged without moving the stepper motor described below, which leads to a reduction of acquisition time.

FIG. 28 is a schematic overview of a breast screening apparatus that can use the generation or detection systems of FIGS. 26 and 27. The output port 509 and the input port 511 are shown. These ports correspond to the output and input ports of FIGS. 26 and 27. The imaging radiation 501 is reflected through plate 523 onto sample 525. The radiation passes through base plate 527 and is then reflected to input port 511. The generator 531 and the detector 533 are located within a movable platform 535. Scanning means 537 are provided which can move the platform 535 such that the whole of the sample can be irradiated and hence imaged.

FIG. 29 shows a detail of the sample receiving area. As shown in FIG. 26 the sample is sandwiched between plates 523 and 527. Plate 523 is movable in relation to plate 527. To image the sample, plate 523 is moved towards plate 527. The sample receiving area is designed for transmission measurements.

FIG. 30 shows a further variation of the coupling optics shown in the previous figures. Here, polyethylene or resistivity Si plane or convex lenses 561 and 563 are used to focus the beam onto the sample 525. Details of the types of lenses have been hereinbefore described with reference to FIGS. 21 and 22.

FIG. 31 shows a further variation on the coupling optics. Here, the off-axis parabolic mirrors are positioned so that the beam diameter of the sample is frequency independence. These optics are described in more detail with reference to FIG. 21.

FIG. 32 shows mammography apparatus where the reflected THz beam 601 is directed into input port 511.

FIG. 33 again shows a reflection geometry arrangement for breast screening. The reflected beam is passed through a series of off-axis parabolic mirrors arranged in a configuration similar to that described in relation to FIG. 21 before being directed into the input port 511.

Further, the radiation from the output port 509 is also passed through a series of off-axis parabolic mirrors in an arrangement similar to that of FIG. 21.

FIG. 34 shows a further variation on the system of FIG. 26. Here, there are two input ports 611 and 613. The input ports can be used to collect either both transmitted radiation, both reflected radiation or reflected and transmitted information individually.

FIG. 35 shows a variation on the system of FIG. 34 with two input ports 611 and 613. The radiation for both input ports is fed into separate detection mechanisms, both of which comprise CCD cameras 615 and 617.

FIG. 36 shows an imaging system with both transmitted THz 701 and reflected THz 703 are collected.

FIG. 37 shows a system for use in THz in the detection of osteoporosis.

Bone may be weakened or rarefied by diseases such as osteoporosis or metastatic cancer. In these cases, there is a change in the density and/or composition of the bone in the effected area, which leads to the bone becoming brittle or weak. Because bone is partially transparent to THz and because both absorption and the refractive index depend on the density and/or composition. Contrast mechanisms such as those previously described on pages 11 and 12 of the specification can be used to both a THz image of the diseases portion and investigate the bone spectroscopically.

Osteoporosis also results in the thinning of the bone.

The osteoporosis apparatus shown in FIG. 37 are similar to those of the breast imaging apparatus described in relation to FIGS. 26 to 36. The sample 701 is placed on a flat stage 703. A polyethylene or other THz transparent material plate 705 is lowered to keep the sample 701 in place. The THz is directed onto the bone and collected in any of the manners described with reference to the breast scanning apparatus (FIGS. 26 to 36).

FIG. 38a shows a visible light image of bones. FIG. 38b shows the corresponding THz image of the bone.

FIG. 39 shows both visible and THz images taken of a tooth. Appropriate analysis of the time of light of THz light through the tooth allows the enamel layer on the outside of the tooth to be separated from the inner region where the enamel and dentine are both present. Time of flight information can be used to assess the thickness and quality of the enamel and dentine of the tooth. The extra option of the absorption of THz light inside the tooth can be used to identify a cavity inside the tooth. Such images can identify pulp stones and the rate of blood flow into the cavity and inspection through resin-based tooth fillings.

FIG. 40 shows THz imaging penetrating through blood. THz in the range (300 GHz to 3 THz) can penetrate through at least 90 microns of blood, the sample used was dried blood. However, this technique can also be used to penetrate liquid water. Data for this blood measurement is shown in FIG. 40a. Either the time of the frequency domain information can be used to allow identification of increased blood flow in certain areas and establish the certain probability of the presence of a tumour.

THz imaging can also be used to detect the presence of skin tumours. FIG. 41 shows a part of the detected THz electric field in the time domain. The sample used to produce these traces is healthy human skin. The three traces are taken from different points on the skin. It can be seen that there is fairly good reproducibility between the traces.

FIG. 42 shows a plot of the power spectrum (obtained by a Fourier transform of the time data) against the THz frequency. The upper trace is a reference trace, obtained by measuring the signal in the absence of the sample. This is taken in the absence of the sample. The three lower parts show the data through healthy skin. As explained for FIG. 41, the three traces correspond to different parts of the sample. There is good repeatability between measurements.

FIG. 43 shows a plot of the transmittance the signal through the skin divided by the reference signal for the data of FIG. 42.

FIG. 44 shows a plot of the absorption (i.e. the reciprocal of the transmission) for both healthy and tumourous skin for frequencies in the THz range. The four upper traces correspond to the signal measured in the tumourous region. The lower trace corresponds to the healthy skin. There is a difference between the tumourous traces. However, it can be clearly seen that the tumour can be easily distinguished from the healthy skin.

FIG. 45a shows a visible image of a tumour. FIG. 45b shows the corresponding THz image of the same sample. To obtain the THz image, the sample has been subdivided into a plurality of pixels. The magnitude of the minimum of the E-field (i.e. the directly measured magnitude of the THz signal) has been plotted at each pixel. It can be seen that the tumourous region (in the centre of the image) has a far higher absorption than that of the healthy skin or the region of the sample. This image can be used to determine the lateral extent of the tumour.

FIG. 46 shows a further image of the tumourous sample. This uses the time of flight of the THz pulse through the sample in order to determine the density and thickness of the tumour into the skin. In this particular figure, the time and position of the e-field minima has been plotted for each pixel.

Figure 45:
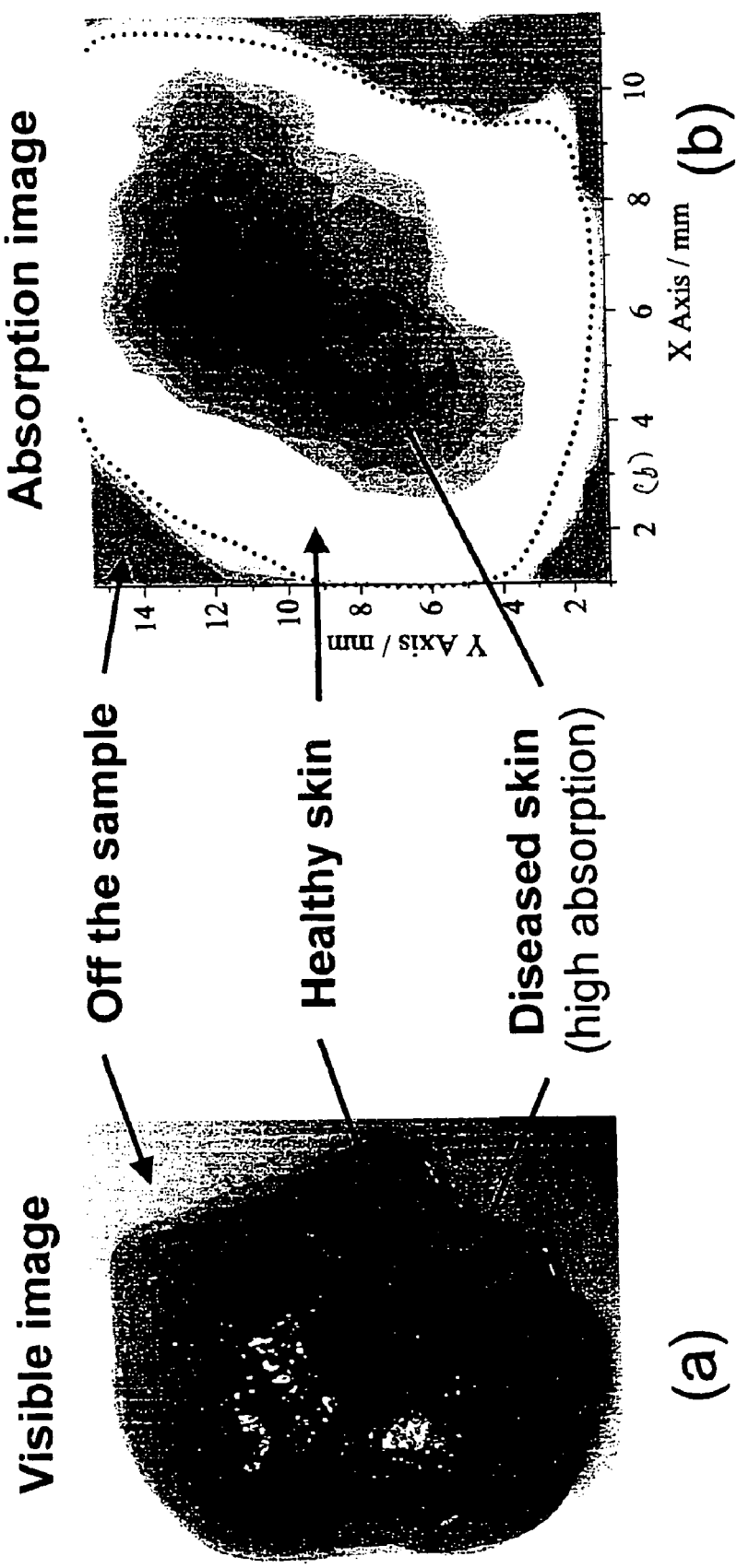

Combining the straight absorption image of FIG. 45 with the time of flight image of FIG. 46 allows a 3D picture of the tumour to be built up.

As previously mentioned, THz frequencies can be used to determine the composition of liquid. FIG. 47 shows the absorption coefficient measured at different THz frequencies for a well known moisturiser, Oil of Olay (registered trade mark), a non-branded moisturiser which will be referred to as "M" and water. Water absorbs radiation in the THz region. Therefore, the water trace has the highest absorption coefficient, M has a medium composition and Olay has the lowest absorption. FIG. 48 shows a plot of THz fields (arbitrary units—which is closely related to the absorption and transmission of the sample) in the time domain. Looking at the maxima of the trace at 2.5 picoseconds, pure Olay is the largest trace. Pure water has the lowest field peak because water is more strongly absorbed than pure Olay. The traces in between are for samples with the following contents: 80% Olay, 20% water; 60% Olay, 40% water; 40% Olay and 60% water; and 20% Olay and 80% water. The pulse size of the mixture decreases as more water is added to the Olay.

FIG. 49 shows a plot of the average absorption coefficient against the percentage of Olay by volume taken from FIG. 48. Comparing this with the average absorption coefficient of M allows the percentage of Olay within the Aloe to be calculated. The finding was that M is equivalent to a mixture of 55% Olay and 43% water.

What is claimed is:

1. A method of imaging a sample, the method comprising:
   a) irradiating the sample to be imaged with pulsed electro-magnetic radiation with a plurality of frequencies in the range of 50 GHz to 84 THz;
   b) subdividing an area of the sample which is to be imaged into a two dimensional array of pixels, and detecting radiation from each pixel over a plurality of frequencies; and
   c) generating an image of the area of the sample from the radiation detected in step (b) using a frequency or a selection of frequencies from the plurality of frequencies in the pulsed electro-magnetic radiation.

2. The method of claim 1, wherein the sample to be imaged in irradiated with pulsed electro-magnetic radiation with a plurality of frequencies in the range from 100 GHz to 20 THz.

3. The process of claim 2, wherein the sample to be imaged in irradiated with pulsed electro-magnetic radiation with a plurality of frequencies in the range from 500 GHz to 10 THz.

4. The method of claim 1, wherein a single image in generated using a selected frequency range.

5. The method of claim 4, wherein the selected frequency range is less than a third of the frequency range of the pulsed electro-magnetic radiation which irradiates the sample.

6. The method of claim 1, wherein a plurality of images in generated from a corresponding plurality of different frequencies.

7. The method of claim 1, wherein, in step (b), the radiation is detected in the time domain and in Fourier transformed to obtain frequency dependent data.

8. The method of claim 1, wherein a fraction of the input pulsed radiation does not irradiate the area of the sample, which is to be imaged, and is detected as a reference signal.

9. The method of claim 1, wherein the method further comprises the step of detecting a reference signal when the area of the sample to be imaged is absent from the path of the pulsed electro-magnetic radiation.

10. The method of claim 8, wherein step (c) comprises the steps of deriving frequency dependent image data from the detected radiation and plotting the frequency dependent image data for each pixel to obtain an image of the sample.

11. The method of claim 8, wherein step (c) comprises the steps of calculating the Power Spectrum for the radiation detected in step (b) and calculating the Power Spectrum of the reference signal.

12. The method of claim 11, wherein the frequency dependent image data is calculated by subtracting the Power Spectrum of the reference signal from the Power Spectrum of the radiation detected in step (b).

13. The method of claim 10, wherein the frequency dependent image data is calculated by dividing the Power Spectrum of the radiation detected in step (b) by the Power Spectrum of the reference signal.

14. The method of claim 10, wherein the frequency dependent image data is calculated by deriving the frequency dependent absorption coefficient from a Fourier transform of the radiation detected in step (b) and a Fourier transform of the reference signal.

15. The method of claim 10, wherein the frequency dependent image data is calculated by deriving the frequency dependent refractive index from a Fourier transform of the radiation detected in step (b) and a Fourier transform of the reference signal.

16. The method of claim 10, wherein the frequency dependent image data is derived for two or more frequencies.

17. The method of claim 16, wherein the frequency dependent image data for the two frequencies is added, subtracted, multiplied and divided for each pixel.

18. The method of claim 10, wherein the frequency dependent image data is obtained for a narrow range of frequencies and the image data is integrated over this narrow range.

19. The method of claim 10, wherein the frequency dependent image data is processed by subdividing the data into a plurality of bands, wherein each band represent a range of magnitudes of the image data for a single frequency or narrow frequency range and each band is assigned a single value or color.

20. The method of claim 19, wherein the bands are not of equal widths in magnitude.

21. The method of claim 19, wherein the image data is derived for more than one frequency and image data for two or more frequencies is combined according to a predetermined rule.

22. The method of claim 21, wherein there are two bands assigned the values '0' and '1' and the predetermined rule is a BOOLEAN algebraic rule.

23. The method of claim 1, the method further comprising the step of displaying a sequence of images generated in step (c) for a plurality of different frequencies.

24. The method of claim 23, wherein the image generated in step (c) is scanable through a continuum of frequencies.

25. The method of claim 23, wherein the image generated in step (c) can be stepped through a plurality of discrete frequencies.

* * * * *